United States Patent
Frank et al.

(10) Patent No.: US 8,735,426 B2
(45) Date of Patent: *May 27, 2014

(54) VANILLOID RECEPTOR LIGANDS, PHARMACEUTICAL COMPOSITIONS CONTAINING THEM, PROCESS FOR MAKING THEM AND USE THEREOF FOR TREATING PAIN AND OTHER CONDITIONS

(75) Inventors: Robert Frank, Aachen (DE); Gregor Bahrenberg, Aachen (DE); Thomas Christoph, Aachen (DE); Klaus Schiene, Juechen (DE); Jean De Vry, Stolberg (DE); Derek Saunders, Aachen (DE); Bernd Sundermann, Friedrichsdorf (DE); Jeewoo Lee, Ansan-Si (KR)

(73) Assignee: Gruenenthal GmbH, Aachen (DE)

( * ) Notice: Subject to any disclaimer, the term of this patent is extended or adjusted under 35 U.S.C. 154(b) by 1367 days.

This patent is subject to a terminal disclaimer.

(21) Appl. No.: 12/081,224

(22) Filed: Apr. 11, 2008

(65) Prior Publication Data

US 2008/0275044 A1 Nov. 6, 2008

(30) Foreign Application Priority Data

Apr. 13, 2007 (DE) .................. 10 2007 017 879

(51) Int. Cl.
*A61K 31/4545* (2006.01)
*C07D 401/02* (2006.01)

(52) U.S. Cl.
USPC ............ 514/318; 514/316; 546/193; 546/194

(58) Field of Classification Search
USPC .................. 514/316, 357; 546/193, 194, 329
See application file for complete search history.

(56) References Cited

U.S. PATENT DOCUMENTS

| 3,306,909 A | 2/1967 | Uloth |
| 3,786,049 A | 1/1974 | Palomo-Coll et al. |

FOREIGN PATENT DOCUMENTS

| DE | 19 66 974 A1 | 1/1976 |
| WO | WO 2005/003084 A1 | 1/2005 |
| WO | WO 2007/045462 A2 | 4/2007 |
| WO | WO 2007/045462 A3 | 4/2007 |

OTHER PUBLICATIONS

Cooke et al. :Preparation of fungicidal . . . CA123:174247 (2001).*
South et al. "Preparation of . . . " CA 135:257039 (2001).*
Dorward "sude reactuins in organic . . . " p. ix (2005).*
Lima et al. "Bioisosterism: a useful . . . " Current Med. Chem, 12, p. 23-49 (2005).*
Exhibit 1 (2012).*
Dorwald "side reactions . . . " p. ix, 1-15 (2005).*
Yoon et al. "Chain-branched acyclic . . . " Bioorg. & Med. Chem. Lett. v.13, p. 1549-1552 (2003).*
International Search Report dated Dec. 1, 2008 with English translation (Four (4) pages).
International Preliminary Report on Patentability dated Nov. 10, 2009 with English translation (Twelve (12) pages).
Cheng et al., "Relationship Between the Inhibition Constant ($K_1$) and the Concentration of Inhibitor Which Causes 50 Per Cent Inhibition ($I_{50}$) of an Enzymatic Reaction," Biochemical Pharmacology, 1973, pp. 3099-3108, Pergamon Press, Great Britain.
Coderre et al., "Contribution of central neuroplasticity to pathological pain: review of clinical and experimental evidence," Pain, 1993, pp. 259-285, vol. 52, Elsevier Science Publishers B.V.
Dubuisson et al., "The Formalin Test: A Quantitative Study of the Analgesic Effects of Morphine, Meperidine, and Brain Stem Stimulation in Rats and Cats," Pain, 1977, pp. 161-174, vol. 4, Elsevier/North-Holand Biomedical Press.
Hendershot et al., "Antagonism of the Frequency of Phenylquinone-Induced Writhing in the Mouse by Weak Analgesics and Nonanalgesics," 1958, pp. 237-240, The Biochemical Research Laboratory, The Dow Chemical Company.

* cited by examiner

*Primary Examiner* — Celia Chang
(74) *Attorney, Agent, or Firm* — Crowell & Moring LLP

(57) ABSTRACT

Compounds corresponding to formula I:

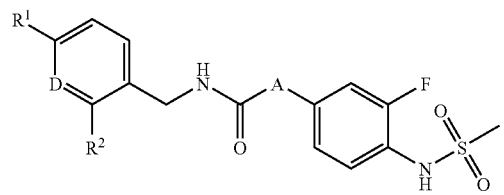

formula I which act as vanilloid receptor ligands, pharmaceutical compositions containing such compounds, a process for the producing such compounds, and the use thereof to treat or inhibit pain and/or various other disorders or conditions.

17 Claims, No Drawings

VANILLOID RECEPTOR LIGANDS, PHARMACEUTICAL COMPOSITIONS CONTAINING THEM, PROCESS FOR MAKING THEM AND USE THEREOF FOR TREATING PAIN AND OTHER CONDITIONS

The present invention relates to novel vanilloid receptor ligands, to processes for the production thereof, to medicinal drugs containing said compounds and to the use of said compounds for the production of medicinal drugs.

The treatment of pain, particularly neuropathic pain, is of great significance in the medical field. There is a global need for effective pain therapies, and an urgent need for action to provide a patient-friendly and targeted treatment of chronic and non-chronic states of pain, this being taken to mean the successful and satisfactory treatment of pain for patients, is documented by the large number of scientific papers which have recently appeared in the field of applied analgetics or in basic research concerning nociception.

A suitable starting point for the treatment of pain, particularly of pain selected from the group consisting of acute pain, chronic pain, neuropathic pain, and visceral pain and more preferably neuropathic pain, is the vanilloid receptor of subtype 1 (VR1/TRPV1), frequently referred to as the capsaicin receptor. This receptor is stimulated, inter alia, by vanilloids such as capsaicin, heat, and protons and plays a central part in the generation of pain. Furthermore, it is significant for a large number of other physiological and pathophysiological processes such as migraine, states of depression, neurodegenerative disorders, cognitive disorders, anxiety, epilepsy, coughing, diarrhea, pruritus, inflammations, disorders of the cardiovascular system, disorders in food intake, medicine addiction, medicine abuse and, in particular, urinary incontinence.

It is thus an object of the invention to provide novel compounds which are particularly suitable for use as pharmacological active substances in medicinal drugs, preferably in medicinal drugs for treatment of disorders or diseases that are at least partially mediated by vanilloid receptors 1 (VR1/TRPV1 receptors).

It has now been found, surprisingly, that the substituted compounds of the general formula I given below show an excellent affinity to the vanilloid receptor of subtype 1 (VR1/TRPV1 receptor) and are therefore particularly suitable for the prophylaxis and/or treatment of disorders or diseases which are at least partially mediated by vanilloid receptors 1 (VR1/TRPV1). The substituted compounds of the general formula I given below also show anti-inflammatory activity.

It is thus an object of the present invention to provide substituted compounds of the general formula I,

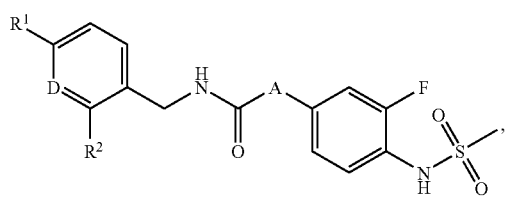

wherein

A stands for a radical selected from the group consisting of

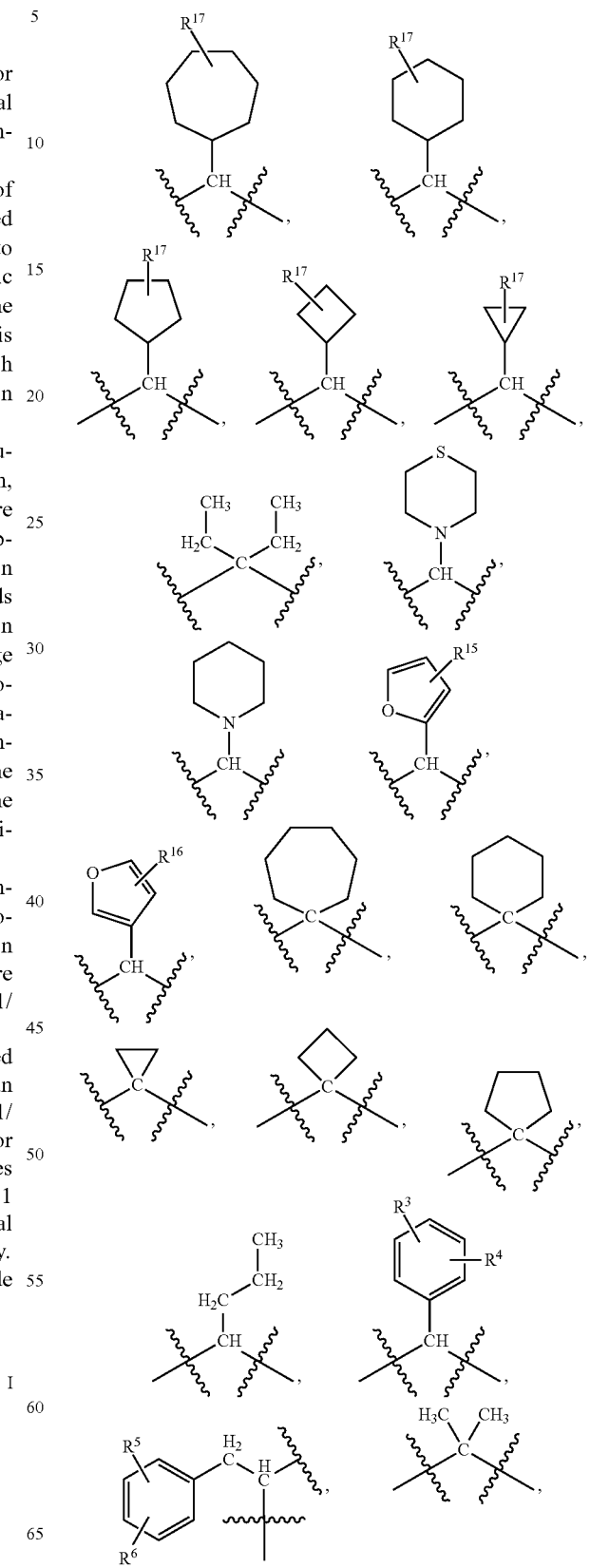

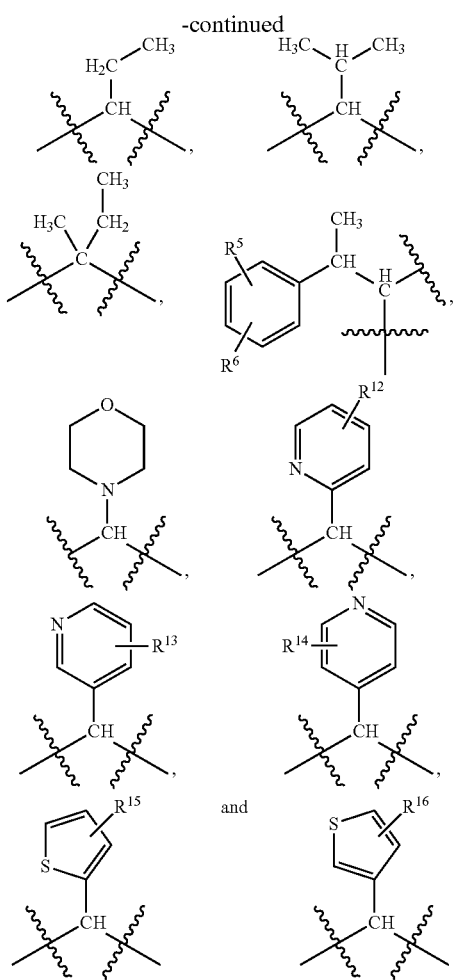

D stands for N or CH;

R$^1$ stands for —SF$_5$; —O—CF$_3$; —O—CFH$_2$; —O—CF$_2$, and H; —CFH$_2$; —CF$_2$H; —CF$_3$; or for or for an unsubstituted or at least monosubstituted tert-butyl radical;

R$^2$ stands for —NHR$^7$; —NR$^8$R$^9$; —OR$^{10}$; —SR$^{11}$;

for an unsaturated or saturated, unsubstituted or at least monosubstituted, three-membered, four-membered, five-membered, six-membered, seven-membered, eight-membered, or nine-membered cycloaliphatic radical optionally exhibiting at least one heteroatom as ring member, each being bonded via a carbon atom in the ring of the cycloaliphatic radical to the basic framework and optionally condensed with a saturated or unsaturated, unsubstituted or at least monosubstituted monocyclic or polycyclic ring system;

or for an unsubstituted or at least monosubstituted five-membered to fourteen-membered aryl radical or heteroaryl radical, which can be condensed with a saturated or unsaturated, unsubstituted or at least monosubstituted monocyclic or polycyclic ring system and/or can be bonded via a linear or branched, unsubstituted or at least monosubstituted C$_{1-6}$ alkylene group or C$_{2-6}$ alkenylene group or C$_{2-6}$-alkynylene group;

R$^3$, R$^4$, R$^5$, and R$^6$ independently stand for H; F; Cl; Br; I; —SF$_5$; —NO$_2$; —CF$_3$; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NH$_2$; —NH—CH$_3$; —NH—C$_2$H$_5$; —N(CH$_3$)$_2$; —N(C$_2$H$_5$)$_2$; methyl; ethyl; isopropyl; n-propyl; n-butyl; tert-butyl; isobutyl, sec-butyl; —O-phenyl; —O—CH$_3$; —O—C$_2$H$_5$; —O—C(CH$_3$)$_3$; —O—CH(CH$_3$)$_2$, or —O—CH$_2$—CH$_2$—CH$_2$—CH$_3$;

R$^7$, R$^8$, R$^9$, R$^{10}$, and R$^{11}$, each independently stand for a linear or branched, saturated or unsaturated, unsubstituted or at least monosubstituted aliphatic C$_{1-10}$ radical;

for an unsaturated or saturated, unsubstituted or at least monosubstituted, three-membered, four-membered, five-membered, six-membered, seven-membered, eight-membered, or nine-membered cycloaliphatic radical optionally containing at least one heteroatom as ring member, which can be condensed with a saturated or unsaturated, unsubstituted or at least monosubstituted monocyclic or polycyclic ring system and/or can be bonded via a linear or branched, unsubstituted or at least monosubstituted C$_{1-6}$ alkylene group or two to six-membered heteroalkylene group;

or for an unsubstituted or at least monosubstituted five-membered to fourteen-membered aryl radical or heteroaryl radical, which can be condensed with a saturated or unsaturated, unsubstituted or at least monosubstituted monocyclic or polycyclic ring system and/or can be bonded via a linear or branched, unsubstituted or at least monosubstituted C$_{1-6}$ alkylene group or two to six-membered heteroalkylene group;

or

R$^8$ and R$^9$ each form, together with the interconnecting nitrogen atom as ring member, a saturated or unsaturated, unsubstituted or at least monosubstituted four-membered, five-membered, six-membered, seven-membered, eight-membered, or nine-membered heterocycloaliphatic radical, optionally containing at least one further heteroatom as ring member, which can be condensed with a saturated or unsaturated, unsubstituted or at least monosubstituted monocyclic or polycyclic ring system;

R$^{2}$, R$^{13}$, R$^{14}$, R$^{15}$, and R$^{16}$, each independently stand for H; F; Cl; Br; I; —SF$_5$; —NO$_2$; —CF$_3$; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NH$_2$; —NH—CH$_3$; —NH—C$_2$H$_5$; —N(CH$_3$)$_2$; —N(C$_2$H$_5$)$_2$; methyl; ethyl; isopropyl; n-propyl; n-butyl; tert-butyl; isobutyl, sec-butyl; —O-phenyl; —O—CH$_3$; —O—C$_2$H$_5$; —O—C(CH$_3$)$_3$; —O—CH(CH$_3$)$_2$ or —O—CH$_2$—CH$_2$—CH$_2$—CH$_3$;

and

R$^{17}$ stands for a linear or branched, saturated or unsaturated, unsubstituted or at least monosubstituted aliphatic C$_{1-10}$ radical;

each optionally in the form of one of the pure stereoisomers thereof, particularly enantiomers or diastereoisomers thereof, the racemates thereof or in the form of a mixture of stereoisomers, particularly the enantiomers and/or diastereoisomers, in an arbitrary mixing ratio, or each in the form of corresponding salts, or each in the form of corresponding solvates;

wherein the aforementioned aliphatic C$_{1-10}$ radicals and tert-butyl radicals can each be optionally substituted by 1, 2, 3, 4, 5, 6, 7, 8, or 9 substituents independently selected from the group consisting of F, Cl, Br, I, —CN, —NO$_2$, —OH, —NH$_2$, —SH, —O(C$_{1-5}$ alkyl), —S(C$_{1-5}$ alkyl), —NH(C$_{1-5}$ alkyl), —N($C_{1-5}$ alkyl)-($C_{1-5}$ alkyl), —C(=O)—O—($C_{1-5}$ alkyl), —O—C(=O)—($C_{1-5}$ alkyl), —O-phenyl, phenyl, —$OCF_3$, and —$SCF_3$;

the aforementioned two to six-membered heteroalkylene groups, $C_{1-6}$ alkylene groups, $C_{2-6}$ alkenylene groups, and $C_{2-6}$ alkynylene groups can each be optionally substituted by 1, 2, 3, 4, 5, 6, 7, 8, or 9 substituents independently selected from the group consisting of F, Cl, Br, I, —CN, —$NO_2$, —OH, —$NH_2$, —SH, —O($C_{1-5}$ alkyl), —S($C_{1-5}$ alkyl), —NH($C_{1-5}$ alkyl), —N($C_{1-5}$ alkyl)-($C_{1-5}$ alkyl), —$OCF_3$, and —$SCF_3$;

the aforementioned heteroalkylene groups each optionally exhibit 1, 2, or 3 heteroatom(s) independently selected from the group consisting of oxygen, sulfur, and nitrogen (NH) as link(s);

the aforementioned (hetero)cycloaliphatic radicals can each be optionally substituted by 1, 2, 3, 4, or 5 substituents independently selected from the group consisting of —($C_{1-6}$ alkylene)-OH, =$CH_2$, —O—($C_{1-5}$ alkylene)oxetanyl, —($C_{1-5}$ alkylene)-O—($C_{1-5}$ alkylene)oxetanyl, —$CH_2$—NH—$C_{1-5}$ alkyl, —$CH_2$—N($C_{1-5}$ alkyl)$_2$, —N[C(=O)—($C_{1-5}$ alkyl)]phenyl, —$CH_2$—O—$C_{1-5}$ alkyl, oxo (=O), thioxo (=S), F, Cl, Br, I, —CN, —$CF_3$, —$SF_5$, —OH, —O—($C_{1-5}$ alkyl), —O—C(=O)—($C_{1-5}$ alkyl), —$NH_2$, —$NO_2$, —O—$CF_3$, —S—$CF_3$, —SH, —S—($C_{1-5}$ alkyl), —$C_{1-5}$ alkyl, —C(=O)—($C_{1-5}$ alkyl), —C(=O)—OH, —C(=O)—O—($C_{1-5}$ alkyl), —NH—($C_{1-5}$ alkyl), —N($C_{1-5}$ alkyl)$_2$, —NH-phenyl, —N($C_{1-5}$ alkyl)phenyl, cyclohexyl, cyclopentyl, (4.5)-dihydroisoxazolyl, thiazolyl, (1,2,5)-thiadiazolyl, thiophenyl, phenethyl, piperidinyl, pyrrolidinyl, —($CH_2$)pyridinyl, pyridinyl, —O-phenyl, —O-benzyl, phenyl, and benzyl, and the cyclic moiety of the radicals oxetanyl, (4,5)-dihydroisoxazolyl, thiazolyl, (1,2,5)-thiadiazolyl, thiophenyl, phenethyl, piperidinyl, pyrrolidinyl, —($CH_2$)pyridinyl, pyridinyl, —O-phenyl, —O-benzyl, phenyl, and benzyl, and the cyclic moiety of the radicals oxetanyl, (4,5)-dihydroisoxazolyl, thiazolyl, (1,2,5)-thiadiazolyl, thiophenyl, phenethyl, —N[C(=O)—$C_{1-5}$ alkyl]phenyl, —NH-phenyl, —N($C_{1-5}$ alkyl)phenyl, —($CH_2$)pyridinyl, pyridinyl, —O-phenyl, —O-benzyl, phenyl, and benzyl can in each case be substituted by 1, 2, 3, 4, or 5 substituents independently selected from the group consisting of F, Cl, Br, —OH, —$CF_3$, —$SF_5$, —CN, —$NO_2$, —$C_{1-5}$ alkyl, —O—($C_{1-5}$ alkyl), —O—$CF_3$, —S—$CF_3$, phenyl, and —O-benzyl, and the aforementioned (hetero)cycloaliphatic radicals can each optionally exhibit 1, 2, or 3 (further) heteroatom(s) independently selected from the group consisting of oxygen, nitrogen, and sulfur;

the rings of the aforementioned monocyclic or polycyclic ring systems can each be optionally substituted by 1, 2, 3, 4, or 5 substituents independently selected from the group consisting of oxo (=O), thioxo (=S), F, Cl, Br, I, —CN, —$CF_3$, —$SF_5$, —OH, —O—($C_{1-15}$ alkyl), —$NH_2$, —$NO_2$, —O—$CF_3$, —S—$CF_3$, —SH, —S—($C_{1-5}$ alkyl), —($C_{1-5}$ alkyl), —C(=O)—($C_{1-15}$ alkyl), —C(=O)—OH, —C(=O)—O—($C_{1-15}$ alkyl), —NH—($C_{1-5}$ alkyl), —N($C_{1-5}$ alkyl)$_2$, —O-phenyl, —O-benzyl, phenyl, and benzyl, and the cyclic moiety of the radicals —O-phenyl, —O-benzyl, phenyl, and benzyl can each be substituted by 1, 2, 3, 4, or 5 substituents independently selected from the group consisting of F, Cl, Br, —OH, —$CF_3$, —$SF_5$, —CN, —$NO_2$, —$C_{1-5}$ alkyl, —O—($C_{1-5}$ alkyl), —O—$CF_3$, —S—$CF_3$, phenyl, and —O-benzyl, and the rings of the aforementioned monocyclic or polycyclic ring systems are each five-membered, six-membered, or seven-membered and can each optionally exhibit 1, 2, 3, 4, or 5 heteroatom(s) as ring member(s), which are independently selected from the group consisting of oxygen, nitrogen, and sulfur;

and the aforementioned aryl radicals or heteroaryl radicals can each be optionally substituted by 1, 2, 3, 4, or 5 substituents independently selected from the group consisting of F, Cl, Br, I, —CN, —$CF_3$, —$SF_5$, —OH, —O—($C_{1-5}$ alkyl), —$NH_2$, —$NO_2$, —O—$CF_3$, —S—$CF_3$, —SH, —S—($C_{1-5}$ alkyl), —($C_{1-5}$ alkyl), —C(=O)—OH, —C(=O)—O—($C_{1-5}$ alkyl), —NH—($C_{1-5}$ alkyl), —N($C_{1-5}$ alkyl)$_2$, —NH—S(=O)$_2$—$C_{1-5}$ alkyl, —NH—C(=O)—O—($C_{1-5}$ alkyl), —C(=O)—H, —C(=O)—($C_{1-5}$ alkyl), —C(=O)—$NH_2$, —C(=O)—NH—($C_{1-5}$ alkyl), —C(=O)—N—($C_{1-5}$ alkyl)$_2$, —O-phenyl, —O-benzyl, phenyl, and benzyl, and the cyclic moiety of the radicals —O-phenyl, —O-benzyl, phenyl, and benzyl can each be substituted by 1, 2, 3, 4, or 5 substituents independently selected from the group consisting of F, Cl, Br, —OH, —$CF_3$, —$SF_5$, —CN, —$NO_2$, —($C_{1-5}$ alkyl), —O—($C_{1-5}$ alkyl), —O—$CF_3$, —S—$CF_3$, phenyl, and —O-benzyl, and the aforementioned heteroaryl radicals each optionally exhibit 1, 2, 3, 4, or 5 heteroatom(s) independently selected from the group consisting of oxygen, nitrogen, and sulfur as ring member(s).

The term "heteroalkylene" designates an alkylene chain in which one or more carbons have each been replaced by a heteroatom independently selected from the group consisting of oxygen, sulfur and nitrogen (NH). Heteroalkylene groups can preferably contain 1, 2, or 3 heteroatom(s) and more preferably one heteroatom, independently selected from the group consisting of oxygen, sulfur and nitrogen (NH), as link(s). Heteroalkylene groups can preferably be two to six-membered and more preferably two or three-membered.

Mention may be made, for example, of heteroalkylene groups such as —$CH_2$—$CH_2$—O—$CH_2$—, —$CH_2$—CH($CH_3$)—O—$CH_2$—, —($CH_2$)—O—, —($CH_2$)$_2$—O—, —($CH_2$)$_3$—O—, —($CH_2$)$_4$—O—, —O—($CH_2$)—, —O—($CH_2$)$_2$—, —O—($CH_2$)$_3$—, —O—($CH_2$)$_4$—, —C($C_2H_5$)—(H)—O—, —O—C($C_2H_5$)—(H)—, —$CH_2$—O—$CH_2$—, —$CH_2$—S—$CH_2$—, —$CH_2$—NH—$CH_2$—, —$CH_2$—NH—, and —$CH_2$—$CH_2$—NH—$CH_2$—$CH_2$.

If one or more of the aforementioned substituents exhibit a linear or branched $C_{1-6}$ alkylene group, these are preferably selected from the group consisting of —($CH_2$)—, —($CH_2$)$_2$—, —C(H)—($CH_3$)—, —($CH_2$)$_3$—, —($CH_2$)$_4$—, —($CH_2$)$_5$—, —C(H)—(C(H)—($CH_3$)$_2$)—, and —C($C_2H_5$)—(H)—.

Saturated or unsaturated $C_{1-10}$ aliphatic radicals can stand for a $C_{1-10}$ alkyl, $C_{2-10}$ alkenyl, or $C_{2-10}$ alkynyl radical. $C_{2-10}$ alkenyl radicals have at least one and preferably 1, 2, 3, or 4 C—C double bonds and $C_{2-10}$ alkynyl radicals at least one and preferably 1, 2, 3, or 4 C—C triple bonds.

Preference is given to $C_{1-10}$-alkyl radicals selected from the group consisting of methyl, ethyl, n-propyl, isopropyl, n-butyl, sec-butyl, isobutyl, tert-butyl, n-pentyl, 3-methylbut-1-yl, 2-pentyl, 3-pentyl, sec-pentyl, neopentyl, 4-methylpent-1-yl, (3,3)-dimethylbut-1-yl, n-hexyl, n-heptyl, 2-heptyl, 3-heptyl, 4-heptyl, n-octyl, n-nonyl, 2-nonyl, 3-nonyl, 4-nonyl, 5-nonyl, and (2,6)-dimethylhept-4-yl, which can be optionally substituted by 1, 2, 3, 4, 5, 6, 7, 8, or 9 substituents independently selected from the group consisting of —O-phenyl, —O—C(=O)—$CH_3$, —O—C(=O)—$C_2H_5$, —O—C(=O)—CH($CH_3$)$_2$, —O—C(=O)—C($CH_3$)$_3$, —C(=O)—O—$CH_3$, —C(=O)—O—$C_2H_5$, —C(=O)—O—CH($CH_3$)$_2$, —C(=O)—O—C($CH_3$)$_3$, F, Cl, Br, I, —CN, —$NO_2$, —OH, —$NH_2$, —SH, —O—$CH_3$, —O—$C_2H_5$, —O—CH($CH_3$)$_2$, —O—C($CH_3$)$_3$, —S—$CH_3$, —S—$C_2H_5$, —S—CH(CH$_3$)$_2$, —S—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)—(C$_2$H$_5$), —OCF$_3$, and —SCF$_3$.

In another preferred embodiment, C$_{2-10}$ alkenyl radicals are selected from the group consisting of vinyl, 1-propenyl, 2-propenyl, 1-butenyl, 2-butenyl, 3-butenyl, 2-methylpropen-1-yl, 3-methylbut-2-en-1-yl, (3,3)-dimethylbut-1-enyl, 2-methylbutene-2-yl, 1-pentenyl, 2-pentenyl, 3-pentenyl, 4-pentenyl, 1-hexenyl, 1-heptenyl, and 1-octenyl, which can be optionally substituted by 1, 2, or 3 substituents independently selected from the group consisting of F, Cl, Br, I, —CN, —NO$_2$, —OH, —NH$_2$, —SH, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)—(C$_2$H$_5$), —OCF$_3$, and —SCF$_3$.

Preference is also given to C$_{2-10}$ alkynyl radicals selected from the group consisting of (3,3)-dimethylbut-1-ynyl, 4-methylpent-1-ynyl, 1-hexynyl, ethynyl, 1-propynyl, 2-propynyl, 1-butynyl, 2-butynyl, 3-butynyl, 1-pentynyl, 2-pentynyl, 3-pentynyl, and 4-pentynyl, which can be optionally substituted by 1, 2, or 3 substituents independently selected from the group consisting of F, Cl, Br, I, —CN, —NO$_2$, —OH, —NH$_2$, —SH, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)—(C$_2$H$_5$), —OCF$_3$, and —SCF$_3$.

Particularly preferred optionally substituted C$_{1-10}$ aliphatic radicals are selected from the group consisting of methyl, —CF$_3$, —CHF$_2$, —CH$_2$F, —CF$_2$Cl, —CCl$_2$F, —CCl$_3$, —CBr$_3$, —CH$_2$—CN, —CH$_2$—O—CH$_3$, —CH$_2$—O—CF$_3$, —CH$_2$—SF$_3$, —CH$_2$—NH$_2$, —CH$_2$—OH, —CH$_2$—SH, —CH$_2$—NH—CH$_3$, —CH$_2$—N(CH$_3$)$_2$, —CH$_2$—N(C$_2$H$_5$)$_2$, —CH$_2$—N(CH$_3$)(C$_2$H$_5$), ethyl, —CF$_2$—CH$_3$, —CHF—CF$_2$Cl, —CF$_2$—CFCl$_2$, —CFCl$_2$—CF$_2$Cl, —CFCl—CFCl$_2$, —CH$_2$—CH$_2$—NH$_2$, —CH$_2$—CH$_2$—OH, —CH$_2$—CH$_2$—SH, —CH$_2$—CH$_2$—NH—CH$_3$, —CH$_2$—CH$_2$—N(CH$_3$)$_2$, —CH$_2$—CH$_2$—N(C$_2$H$_5$)$_2$, —CH$_2$—CH$_2$—N(CH$_3$)(C$_2$H$_5$), —CH$_2$—CF$_3$, —C$_2$F$_5$, —CH$_2$—CCl$_3$, —CH$_2$—CBr$_3$, —CH$_2$—CH$_2$—CN, n-propyl, —CH$_2$—CH$_2$—CH$_2$—OH, —CH$_2$—CH$_2$—CH$_2$—SH, —CH$_2$—CH$_2$—CH$_2$—NH$_2$, —CH$_2$—CH$_2$—CH$_2$—NH—CH$_3$, —CH$_2$—CH$_2$—CH$_2$—N(CH$_3$)$_2$, —CH$_2$—CH$_2$—CH$_2$—N(C$_2$H$_5$)$_2$, —CH$_2$—CH$_2$—CH$_2$—N(CH$_3$)(C$_2$H$_5$), —CH$_2$—CH$_2$—O—CH$_3$, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, —CH$_2$—CH$_2$—CH$_2$—CF$_3$, —CH$_2$—CH$_2$—CH$_2$—CH$_2$—CF$_3$, —CH$_2$—O—C(=O)—CH$_3$, —CH$_2$—O—C(=O)—C$_2$H$_5$, —CH$_2$—O—C(=O)—CH(CH$_3$)$_2$, —CH$_2$—O—C(=O)—C(CH$_3$)$_3$, —CH$_2$—C(=O)—O—CH$_3$, —CH$_2$—C(=O)—O—C$_2$H$_5$, —CH$_2$—C(=O)—O—C(CH$_3$)$_3$, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—CH$_2$—O—CH$_3$, sec-butyl, isobutyl, tert-butyl, n-pentyl, sec-pentyl, neopentyl, n-hexyl, vinyl, 1-propenyl, 2-propenyl, 1-butenyl, 2-butenyl, 3-butenyl, 2-methylbutene-2-yl, (1,1,2)-trifluoro-1-butenyl, 1-pentenyl, 2-pentenyl, 3-pentenyl, 4-pentenyl, —CF=CF$_2$, —CCl=CCl$_2$, —CH$_2$—CF=CF$_2$, —CH$_2$—CCl=CCl$_2$, —C≡C—I, —C≡C—F, and —C≡C—Cl.

If one or more of the aforementioned substituents stand for a (hetero)cycloaliphatic radical, which can be optionally condensed with a saturated or unsaturated, unsubstituted or at least monosubstituted monocyclic or polycyclic ring system, these can preferably be selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, (1,2,3,6)-tetrahydropyridinyl, azepanyl, azocanyl, diazepanyl, dithiolanyl, (1,3,4,5)-tetrahydropyrido[4,3-b]indolyl, (3,4)-dihydro-1H-isoquinolinyl, (1,3,4,9)-tetrahydro[b]carbolinyl, and (1,3)-thiazolidinyl.

As examples of suitable (hetero)cycloaliphatic radicals which can be unsubstituted or monosubstituted or polysubstituted and are condensed with a monocyclic or bicyclic ring system, there may be mentioned (4,5,6,7)-tetrahydroisoxazolo[5,4-c]pyridinyl, (2,3)-dihydro-1H-indenyl, 3-azabicyclo[3.1.1]heptyl, 3-acabicyclo[3.2.1]octyl, 6-azabicyclo[3.3.1]heptyl, 8-acabicyclo[3.2.1]octyl, isoindolyl, indolyl, (1,2,3,4)-tetrahydroquinolinyl, (1,2,3,4)-tetrahydroisoquinolinyl, (2,3)-dihydro-1H-isoindolyl, (1,2,3,4)-tetrahydronaphthyl, (2,3)-dihydrobenzo[1,4]dioxinyl, benzo[1,3]dioxolyl, (1,4)-benzodioxanyl, (2,3)-dihydrothieno[3,4-b][1,4]dioxinyl, (3,4)-dihydro-2H-benzo[1,4]oxazinyl, octahydro-1H-isoindolyl, and octahydropyrrolo[3,4-c]pyrrolyl.

(Hetero)cycloaliphatic radicals can form, within the scope of the present invention, a spirocyclic radical with another (hetero)cycloaliphatic radical via a carbon atom common to both rings.

As examples of suitable spirocyclic radicals there may be mentioned a 6-azaspiro[2.5]octyl radical, 8-azaspiro[4.5]decyl radical, and a 1-oxa-2,8-diazaspiro[4.5]dec-2-enyl radical.

More preferably, the (hetero)cycloaliphatic radicals can each be optionally substituted by 1, 2, 3, 4, or 5 substituents independently selected from the group consisting of oxo (=O), thioxo (=S), F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)—(C$_2$H$_5$), —CH$_2$—OH, —CH$_2$—CH$_2$—OH, =CH$_2$, —CH$_2$—O—CH$_2$-oxetanyl, —O—CH$_2$-oxetanyl, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]phenyl, —N—[C(=O)—CH$_3$]phenyl, —CH$_2$—O—CH$_3$, —CH$_2$—O—CH$_2$—CH$_3$, —NH-phenyl, —N(CH$_3$)phenyl, —N(C$_2$H$_5$)phenyl, —N(C$_2$H$_5$)phenyl, —O—CH$_2$—CH$_2$—CH$_2$—CH$_3$, (4.5)-dihydroisoxazolyl, thiazolyl, (1,2,5)-thiadiazolyl, thiophenyl, phenethyl, cyclohexyl, cyclopentyl, piperidinyl, pyrrolidinyl, —O—C(=O)—CH$_3$, —O—C(=O)—C$_2$H$_5$, —O—C(=O)—C(CH$_3$)$_3$, —(CH$_2$)pyridinyl, pyridinyl, —O-phenyl, —O-benzyl, phenyl, and benzyl, and the cyclic moiety of the radicals oxetanyl, (4.5)-dihydroisoxazolyl, thiazolyl, (1,2,5)-thiadiazolyl, thiophenyl, phenethyl, —N—[C(=O)—C$_2$H$_5$]phenyl, —N—[C(=O)—CH$_3$]phenyl, —NH-phenyl, —N(CH$_3$)phenyl, —N(C$_2$H$_5$)phenyl, —(CH$_2$)pyridinyl, pyridinyl, —O-phenyl, —O-benzyl, phenyl, and benzyl can in each case be substituted by 1, 2, 3, 4, or 5 substituents independently selected from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH₃, —O—C₂H₅, —O—CH(CH₃)₂, —O—C(CH₃)₃, —O—CF₃, —S—CF₃, phenyl, and —O-benzyl.

If one or more of the aforementioned substituents stand for an aryl radical, this can preferably be selected from the group consisting of phenyl and naphthyl (1-naphthyl and 2-naphthyl).

If one or more of the aforementioned substituents stand for a heteroaryl radical, this can preferably be selected from the group consisting of tetrazolyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzoxazolyl, benzisoxazolyl, thiazolyl, oxazolyl, isoxazolyl, pyridazinyl, pyrazinyl, pyrimidinyl, indazolyl, quinoxalinyl, quinolinyl, and isoquinolinyl.

As examples of suitable aryl and heteroaryl radicals, which can be unsubstituted or monosubstituted or polysubstituted and are condensed with a monocyclic or bicyclic ring system, there may be mentioned isoindolyl, indolyl, (1,2,3,4)-tetrahydroquinolinyl, (1,2,3,4)-tetrahydroisoquinolinyl, (2,3)-dihydro-1H-isoindolyl, (1,2,3,4)-tetrahydronaphthyl, (2,3)-dihydrobenzo[1.4]dioxinyl, (2,3)-dihydrothieno[3,4-b][1.4]dioxinyl, benzo[1.3]dioxolyl, and (1,4)-benzodioxanyl.

More preferably, the aryl radicals or heteroaryl radicals can each be optionally substituted by 1, 2, 3, 4, or 5 substituents independently selected from the group consisting of F, Cl, Br, I, —CN, —CF₃, —SF₅, —OH, —O—CH₃, —O—C₂H₅, —O—CH(CH₃)₂, —O—C(CH₃)₃, —NH₂, —NO₂, —O—CF₃, —S—CF₃, —SH, —S—CH₃, —S—C₂H₅, —S—CH(CH₃)₂, —S—C(CH₃)₃, methyl, ethyl, n-propyl, isopropyl, n-butyl, sec-butyl, isobutyl, tert-butyl, n-pentyl, —C(=O)—OH, —C(=O)—O—CH₃, —C(=O)—O—C₂H₅, —C(=O)—O—CH(CH₃)₂, —C(=O)—O—C(CH₃)₃, —NH—CH₃, —NH—C₂H₅, —NH—C(CH₃)₃, —N(CH₃)₂, —N(C₂H₅)₂, —N(CH₃)(C₂H₅), —NH—S(=O)₂—CH₃, —NH—S(=O₂)—C₂H₅, —NH—S(=O)₂—CH(CH₃)₂, —NH—C(=O)—O—CH₃, —NH—C(=O)—O—C₂H₅, —NH—C(=O)—O—C(CH₃)₃, —C(=O)—H, —C(=O)—CH₃, —C(=O)—C₂H₅, —C(=O)—CH(CH₃)₂, —C(=O)—C(CH₃)₃, —C(=O)—NH₂, —C(=O)—NH—CH₃, —C(=O)—NH—C₂H₅, —C(=O)—N(CH₃)₂, —C(=O)—N(C₂H₅)₂, —O-phenyl, —O-benzyl, phenyl and benzyl, and the cyclic moiety of the radicals —O-phenyl, —O-benzyl, phenyl, and benzyl can in each case be substituted by 1, 2, 3, 4, or 5 substituents independently selected from the group consisting of F, Cl, Br, —OH, —CF₃, —SF₅, —CN, —NO₂, methyl, ethyl, n-propyl, isopropyl, n-butyl, sec-butyl, isobutyl, tert-butyl, —O—CH₃, —O—C₂H₅, —O—CH(CH₃)₂, —O—C(CH₃)₃, —O—CF₃, —S—CF₃, phenyl, and —O-benzyl.

If a polycyclic ring system such as a bicyclic ring system is present, the different rings can independently exhibit a different degree of saturation, i.e. be saturated or unsaturated. A polycyclic ring system is preferably a bicyclic ring system.

As examples of aryl radicals condensed with a monocyclic or polycyclic ring system mention may be made of (1,3)-benzodioxolyl and (1,4)-benzodioxanyl.

If one or more of the aforementioned substituents have a monocyclic or polycyclic ring system, this can preferably be substituted by 1, 2, 3, 4, or 5 substituents independently selected from the group consisting of oxo (=O), thioxo (=S), F, Cl, Br, I, —CN, —CF₃, —SF₅, —OH, —O—CH₃, —O—C₂H₅, —O—CH(CH₃)₂, —O—C(CH₃)₃, —NH₂, —NO₂, —O—CF₃, —S—CF₃, —SH, —S—CH₃, —S—C₂H₅, —S—CH(CH₃)₂, —S—C(CH₃)₃, methyl, ethyl, n-propyl, isopropyl, n-butyl, sec-butyl, isobutyl, tert-Butyl, n-pentyl, —C(=O)—OH, —C(=O)—O—CH₃, —C(=O)—O—C₂H₅, —C(=O)—O—CH(CH₃)₂, —C(=O)—O—C(CH₃)₃, —NH—CH₃, —NH—C₂H₅, —NH—C(CH₃)₃, —N(CH₃)₂, —N(C₂H₅)₂, —N(CH₃)(C₂H₅), —NH—C(=O)—O—CH₃, —NH—C(=O)—O—C₂H₅, —NH—C(=O)—O—C(CH₃)₃, —C(=O)—H, —C(=O)—CH₃, —C(=O)—C₂H₅, —C(=O)—CH(CH₃)₂, —C(=O)—C(CH₃)₃, —C(=O)—NH₂, —C(=O)—NH—CH₃, —C(=O)—NH—C₂H₅, —C(=O)—N(CH₃)₂, —C(=O)—N(C₂H₅)₂, —O-phenyl, —O-benzyl, phenyl and benzyl, and the cyclic moiety of the radicals —O-phenyl, —O-benzyl, phenyl, and benzyl can in each case be substituted by 1, 2, 3, 4, or 5 substituents independently selected from the group consisting of F, Cl, Br, —OH, —CF₃, —SF₅, —CN, —NO₂, methyl, ethyl, n-propyl, isopropyl, n-butyl, sec-butyl, isobutyl, tert-butyl, —O—CH₃, —O—C₂H₅, —O—CH(CH₃)₂, —O—C(CH₃)₃, —O—CF₃, —S—CF₃, phenyl, and —O-benzyl.

Preference is given to C₂₋₆ alkenylene groups such as —CH=CH— and —CH₂—CH=CH—.

Preference is given to C₂₋₃ alkynylene groups such as —C≡C— and —CH₂—C≡C—.

Preference is given to compounds of the general formulas Ic, Id, Ie, and If,

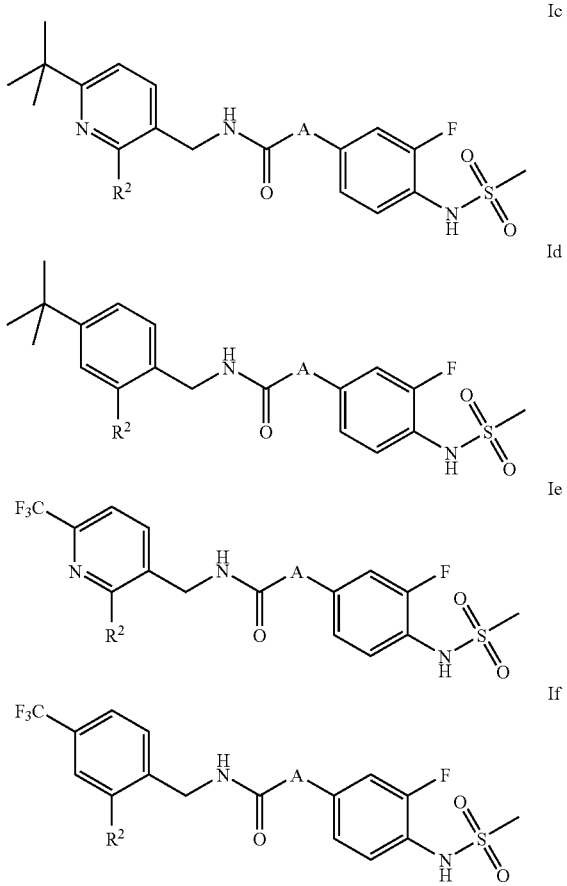

in which
R² and A have the aforementioned meanings;
each optionally in the form of one of the pure stereoisomers thereof, particularly enantiomers or diastereoisomers thereof, the racemates thereof or in the form of a mixture of stereoisomers, particularly the enantiomers and/or diastereoisomers, in an arbitrary mixing ratio, or each in the form of corresponding salts, or each in the form of corresponding solvates.

Preference is given to compounds of the above general formula I, Ic, Id, Ie, and If
in which
A stands for a radical selected from the group consisting of;

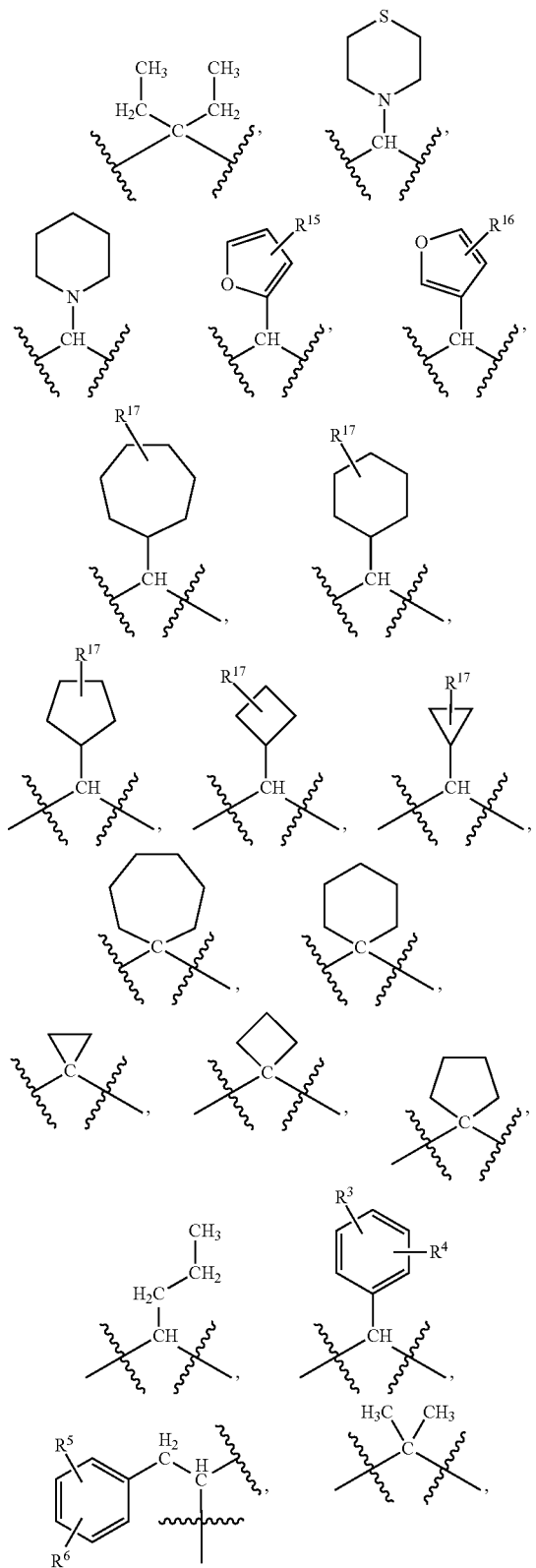

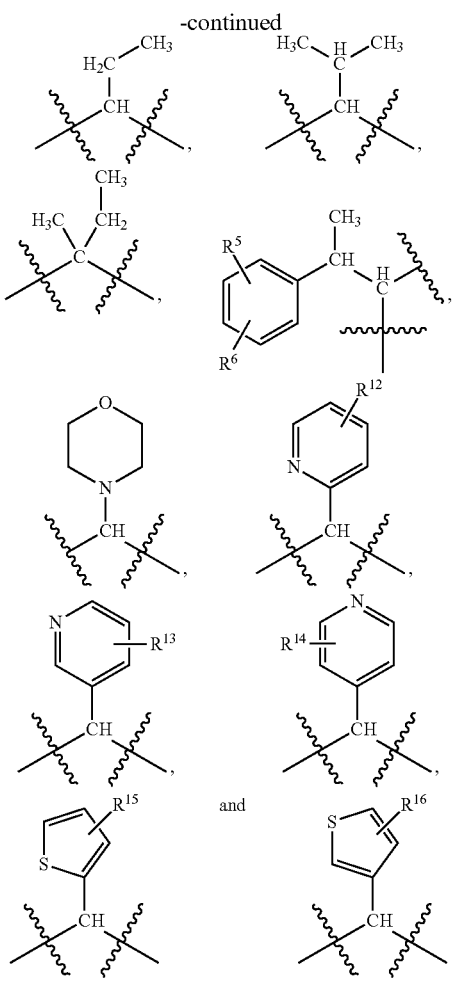

D stands for N or CH;
R¹ stands for —SF₅; —O—CF₃; —O—CFH₂; —O—CF₂H; —CFH₂; —CF₂H; —CF₃; or for a tert-butyl radical, each of which can be unsubstituted or substituted by 1, 2, 3, 4, 5, 6, 7, 8, or 9 substituents independently selected from the group consisting of F, Cl, Br, I, —CN, —NO₂, —OH, —NH₂, —SH, —O—CH₃, —O—C₂H₅, —O—CH(CH₃)₂, —NH—CH₃, and —NH—C₂H₅;

R² stands for —NHR⁷; —NR⁸R⁹; —OR¹⁰; —SR¹¹;
for a radical selected from the group consisting of cyclopropyl, cyclobutyl, cyclopentyl, cyclohexyl, cycloheptyl, cyclohexenyl, pyrrolidinyl, piperidinyl, morpholinyl, piperazinyl, azepanyl, diazepanyl, azocanyl, and thiomorpholinyl, each of which is bonded via a carbon atom of the rings of the aforementioned residues to the basic framework and can be unsubstituted or optionally substituted by 1, 2, 3, 4, or 5 substituents independently selected from the group consisting of —C(=O)—O—CH₃, —C(=O)—O—C₂H₅, —C(=O)—O—C(CH₃)₃, —C(=O)—CH₃, —C(=O)—C₂H₅, —C(=O)—C(CH₃)₃, —CN, —CH₂—N(CH₃)₂, —CH₂—N(C₂H₅)₂, —CH₂—NH—CH₃, —CH₂—NH—C₂H₅, —N—[C(=O)—C₂H₅]phenyl, —N—[C(=O)—CH₃]phenyl, oxo (=O), thioxo (=S), methyl, ethyl, n-propyl, isopropyl, n-butyl, sec-butyl, isobutyl, tert-butyl, and n-pentyl;
or for a radical selected from the group consisting of (1,3)-benzodioxolyl, (1,4)-benzodioxanyl, indolyl, tetrazolyl, (2,3)-dihydrothieno[3,4-b][1,4]dioxinyl, benzo[b]furanyl, phenyl, naphthyl, oxazolyl, thiazolyl, imidazolyl, pyrimidinyl, thiophenyl, furanyl, and pyridinyl, each of which can be unsubstituted or optionally substituted by 1, 2, 3, 4, or 5 substituents independently selected from the group consisting of F, Cl, Br, I, —CN, —$CF_3$, —$SF_5$, —OH, —O—$CH_3$, —O—$C_2H_5$, —$NH_2$, —$N(CH_3)_2$, —$N(C_2H_5)_2$, —NH—S(=O)$_2$—$CH_3$, —NH—S(=$O_2$)—$C_2H_5$, —NH—S(=O)$_2$—$CH(CH_3)_2$, —$NO_2$, —O—$CF_3$, —S—$CF_3$, —SH, —S—$CH_3$, —S—$C_2H_5$, —S—$CH(CH_3)_2$, —S—$C(CH_3)_3$, methyl, ethyl, n-propyl, isopropyl, n-butyl, sec-butyl, isobutyl, and tert-butyl;

$R^3$, $R^4$, $R^5$, and $R^6$ each independently
  stand for H; F; Cl; Br; I; —$SF_5$; —$NO_2$; —$CF_3$; —CN; —$NH_2$; —OH; —SH; methyl; ethyl; isopropyl; n-propyl; n-butyl; tert-butyl; sec-butyl; isobutyl, —O-phenyl; —O—$CH_3$; —O—$C_2H_5$; —O—$C(CH_3)_3$; —O—$CH(CH_3)_2$, or —O—$CH_2$—$CH_2$—$CH_2$—$CH_3$;

$R^7$, $R^8$, $R^9$, $R^{10}$, and $R^{11}$ each independently
  stand for a radical selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethylhept-4-yl, 3-methylbutyl, n-hexyl, (3,3)-dimethylbutyl, —$CH_2$—$CH_2$—O—$CH_3$, —$CH_2$—$CH_2$—O—$C_2H_5$, —$CH_2$—$CH_2$—$CH_2$—O—$CH_3$, ethenyl, propenyl, 2-butenyl, 3-butenyl, 2-pentenyl, and 3-pentenyl;

for a radical selected from the group consisting of 2,3-dihydro-1H-indenyl, cyclopropyl, oxetanyl, cyclobutyl, cyclopentyl, cyclohexyl, cycloheptyl, pyrrolidinyl, piperidinyl, morpholinyl, piperazinyl, azepanyl, diazepanyl, azocanyl, and thiomorpholinyl, each of which can be bonded via a —$CH_2$—O—, —$CH_2$—$CH_2$—O—, —$CH_2$—$CH_2$—O—$CH_2$—, —$CH_2$—$CH(CH_3)$—O—$CH_2$—, —$(CH_2)$—, —$(CH_2)_2$—, or —$(CH_2)_3$ group and/or each can be unsubstituted or optionally substituted by 1, 2, 3, 4, or 5 substituents independently selected from the group consisting of methyl, ethyl, n-propyl, isopropyl, n-butyl, sec-butyl, isobutyl, tert-butyl, —C(=O)—O—$CH_3$, —C(=O)—O—$C_2H_5$, —C(=O)—O—$CH(CH_3)_2$, and —C(=O)—O—$C(CH_3)_3$;

or for a radical selected from the group consisting of —$(CH_2)$-pyridinyl, —$(CH_2)_2$-pyridinyl, benzyl, phenethyl, phenyl, naphthyl, oxazolyl, thiazolyl, imidazolyl, pyrimidinyl, thiophenyl, furanyl, pyrrolyl, und pyridinyl, and the radical can in each case be unsubstituted or optionally substituted by 1, 2, 3, 4, or 5 substituents independently selected from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, —S—$CH(CH_3)_2$, —S—$C(CH_3)_3$, methyl, ethyl, n-propyl, isopropyl, n-butyl, sec-butyl, isobutyl, and tert-butyl;
or
$R^8$ and $R^9$
  each form, together with the interconnecting nitrogen atom as ring member, a radical selected from the group consisting of 3-azabicyclo[3.1.1]heptyl, 6-azaspiro[2.5]octyl, 3-acabicyclo[3.2.1]octyl, 6-azabicyclo[3.3.1]heptyl, 8-acabicyclo[3.2.1]octyl, 1-oxa-2,8-diazaspiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, piperazinyl, morpholinyl, azepanyl, diazepanyl, and thiomorpholinyl, each of which can be unsubstituted or optionally substituted by 1, 2, 3, 4, or 5 substituents independently selected from the group consisting of —$CH_2$—O—$CH_2$-oxetanyl, —O—$CH_2$-oxetanyl, —$CH_2$—OH, —$CH_2$—$CH_2$—OH, =$CH_2$, (4,5)-dihydroisoxazolyl, thiazolyl, (1,2,5)-thiadiazolyl, thiophenyl, phenethyl, —CN, —$CH_2$—$N(CH_3)_2$, —$CH_2$—$N(C_2H_5)_2$, —$CH_2$—NH—$CH_3$, —$CH_2$—NH—$C_2H_5$, —N—[C(=O)—$C_2H_5$]-phenyl, —N—[C(=O)—$CH_3$]-phenyl, —$CH_2$—O—$CH_3$, —$CH_2$—O—$CH_2$—$CH_3$, oxo (=O), thioxo (=S), F, Cl, Br, I, —CN, —$CF_3$, —$SF_5$, —OH, —O—$CH_3$, —O—$C_2H_5$, —O—$CH(CH_3)_2$, —O—$C(CH_3)_3$, —$NH_2$, —$NO_2$, —O—$CF_3$, —S—$CF_3$, —SH, —S—$CH_3$, —S—$C_2H_5$, —S—$CH(CH_3)_2$, —S—$C(CH_3)_3$, methyl, ethyl, n-propyl, isopropyl, n-butyl, sec-butyl, isobutyl, tert-butyl, n-pentyl, —C(=O)—$CH_3$, —C(=O)—$C_2H_5$, —C(=O)—$CH(CH_3)_2$, —C(=O)—$C(CH_3)_3$, —C(=O)—OH, —C(=O)—O—$CH_3$, —C(=O)—O—$C_2H_5$, —C(=O)—O—$CH(CH_3)_2$, —C(=O)—O—$C(CH_3)_3$, —NH—$CH_3$, —NH—$C_2H_5$, —NH—$C(CH_3)_3$, —$N(CH_3)_2$, —$N(C_2H_5)_2$, —$N(CH_3)(C_2H_5)$, —NH-phenyl, —$N(CH_3)$phenyl, —$N(C_2H_5)$phenyl, —$N(C_2H_5)$phenyl, —O—$CH_2$—$CH_2$—$CH_2$—$CH_3$, cyclohexyl, cyclopentyl, piperidinyl, pyrrolidinyl, —O—C(=O)—$CH_3$, —O—C(=O)—$C_2H_5$, —O—C(=O)—$C(CH_3)_3$, —$(CH_2)$pyridinyl, pyridinyl, —O-phenyl, —O-benzyl, phenyl, and benzyl, and the cyclic moiety of the radicals oxetanyl, (4,5)-dihydroisoxazolyl, thiazolyl, (1,2,5)-thiadiazolyl, thiophenyl, phenethyl, —N—[C(=O)—$C_2H_5$]phenyl, —N—[C(=O)—$CH_3$]phenyl, —NH-phenyl, —$N(CH_3)$phenyl, —$N(C_2H_5)$phenyl, —$(CH_2)$pyridinyl, pyridinyl, —O-phenyl, —O-benzyl, phenyl, and benzyl can in each case be substituted by 1, 2, 3, 4, or 5 substituents independently selected from the group consisting of —$CF_3$, F, Cl, Br, —OH, —$CF_3$, —$SF_5$, —CN, —$NO_2$, methyl, ethyl, n-propyl, isopropyl, n-butyl, sec-butyl, isobutyl, tert-butyl, —O—$CH_3$, —O—$C_2H_5$, —O—$CH(CH_3)_2$, —O—$C(CH_3)_3$, —O—$CF_3$, —S—$CF_3$, phenyl, and —O-benzyl;

$R^{12}$, $R^{13}$, $R^{14}$, $R^{15}$, and $R^{16}$ each independently
  stand for H; F; Cl; Br; I; —$SF_5$; —$NO_2$; —$CF_3$; and —CN; —$NH_2$; —OH; —SH; methyl; ethyl; isopropyl; n-propyl; n-butyl; and tert-butyl; isobutyl, sec-butyl; —O-phenyl; —O—$CH_3$; —O—$C_2H_5$; —O—$C(CH_3)_3$; —O—$CH(CH_3)_2$; —O—$CH_2$; or —$CH_2$—$CH_2$—$CH_3$;
and
$R^{17}$ stands for hydrogen or for a radical selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethylhept-4-yl, 3-methylbutyl, n-hexyl, and (3,3)-dimethylbutyl;

in each case optionally in the form of one of the pure stereoisomers thereof, particularly enantiomers or diastereoisomers, or the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Special preference is given to compounds of the general formula Ia,

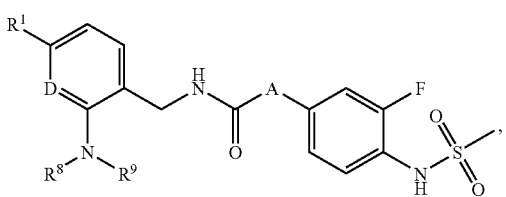

in which
A has the aforementioned meaning;
D stands for N or CH;

R¹ stands for —SF₅; —O—CF₃; —O—CFH₂; —O—CF₂H; —CFH₂; —CF₂H; —CF₃; or for a tert-butyl radical;

R³, R⁴, R⁵, and R⁶ each independently
stand for H; F; Cl; Br; —NO₂; —CF₃; —CN; —OH; methyl; ethyl; isopropyl; n-propyl; n-butyl; tert-butyl; isobutyl, sec-butyl; —O-phenyl; —O—CH₃; or —O—C₂H₅;

R⁸ and R⁹ each independently
stand for a radical selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethylhept-4-yl, 3-methylbutyl, n-hexyl, (3,3)-dimethylbutyl, —CH₂—CH₂—O—CH₃, —CH₂—CH₂—O—C₂H₅, —CH₂—CH₂—CH₂—O—CH₃, ethenyl, propenyl, 2-butenyl, 3-butenyl, 2-pentenyl, and 3-pentenyl;

for a radical selected from the group consisting of 2,3-dihydro-1H-indenyl, cyclopropyl, oxetanyl, cyclobutyl, cyclopentyl, cyclohexyl, cycloheptyl, pyrrolidinyl, piperidinyl, morpholinyl, piperazinyl, azepanyl, diazepanyl, azocanyl, and thiomorpholinyl, each of which can be unsubstituted or optionally substituted by 1, 2, 3, 4, or 5 substituents independently selected from the group consisting of methyl, ethyl, n-propyl, isopropyl, n-butyl, sec-butyl, tert-butyl, isobutyl, —C(=O)—O—CH₃, —C(=O)—O—C₂H₅, —C(=O)—O—CH(CH₃)₂, and —C(=O)—O—C(CH₃)₃;

or
R⁸ and R⁹
each form, together with the interconnecting nitrogen atom as ring member, a radical selected from the group consisting of 3-azabicyclo[3.1.1]heptyl, 6-azaspiro[2.5]octyl, 3-acabicyclo[3.2.1]octyl, 6-azabicyclo[3.3.1]heptyl, 8-acabicyclo[3.2.1]octyl, 1-oxa-2,8-diazaspiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, piperazinyl, morpholinyl, azepanyl, diazepanyl, and thiomorpholinyl, each of which is unsubstituted or optionally substituted by 1, 2, 3, 4, or 5 substituents independently selected from the group consisting of phenethyl, —CH₂—N(CH₃)₂, —CH₂—N(C₂H₅)₂, —CH₂—NH—CH₃, —CH₂—NH—C₂H₅, —N—[C(=O)—C₂H₅]-phenyl, —N—[C(=O)—CH₃]phenyl, —CH₂—O—CH₃, —CH₂—O—CH₂—CH₃, oxo (=O), thioxo (=S), —OH, —O—CH₃, —O—C₂H₅, —O—CH(CH₃)₂, —O—C(CH₃)₃, —NH₂, methyl, ethyl, n-propyl, isopropyl, n-butyl, sec-butyl, isobutyl, tert-butyl, n-pentyl, —C(=O)—CH₃, —C(=O)—C₂H₅, —C(=O)—CH(CH₃)₂, —C(=O)—C(CH₃)₃, —C(=O)—OH, —C(=O)—O—CH₃, —C(=O)—O—C₂H₅, —C(=O)—O—CH(CH₃)₂, —C(=O)—O—C(CH₃)₃, —NH—CH₃, —NH—C₂H₅, —NH—C(CH₃)₃, —N(CH₃)₂, —N(C₂H₅)₂, —N(CH₃)(C₂H₅), phenyl and benzyl, and the cyclic moiety of the radicals phenethyl, —N—[C(=O)—C₂H₅]phenyl, —N—[C(=O)—CH₃]phenyl, phenyl, and benzyl can in each case be substituted by 1, 2, 3, 4, or 5 substituents independently selected from the group consisting of F, Cl, Br, —CF₃, methyl, ethyl, n-propyl, isopropyl, n-butyl, sec-butyl, isobutyl, tert-butyl, —O—CH₃, and —O—C₂H₅;

R¹², R¹³, R¹⁴, R¹⁵, and R¹⁶ each independently
stand for H; F; Cl; Br or —CF₃;
and
R¹⁷ stands for hydrogen or for a radical selected from the group consisting of methyl, ethyl, n-propyl, isopropyl, n-butyl, sec-butyl, isobutyl, and tert-butyl;

each optionally in the form of one of the pure stereoisomers thereof, particularly enantiomers or diastereoisomers thereof, the racemates thereof or in the form of a mixture of stereoisomers, particularly the enantiomers and/or diastereoisomers, in an arbitrary mixing ratio, or each in the form of corresponding salts, or each in the form of corresponding solvates.

Special preference is given to compounds of the general formula Ia1, Ia2, Ia3, and Ia4,

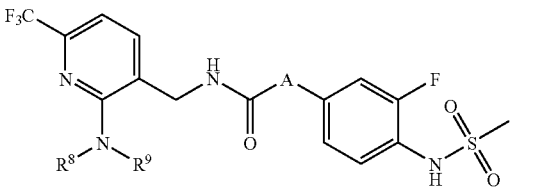

Ia1

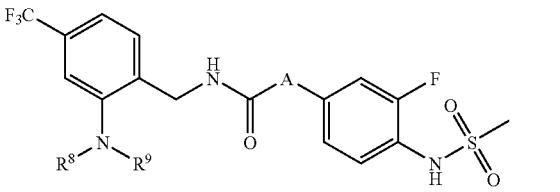

Ia2

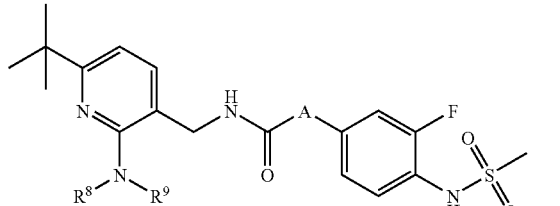

Ia3

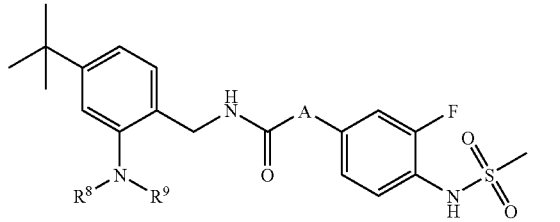

Ia4 in which, in each case,
A has the aforementioned meaning;
R³, R⁴, R⁵, and R⁶ each independently
stand for H; F; Cl; Br; —NO₂; —CF₃; —CN; —OH; methyl; ethyl; isopropyl; n-propyl; n-butyl; tert-butyl; sec-butyl; isobutyl, —O-phenyl; —O—CH₃ or —O—C₂H₅;
R⁸ and R⁹ each independently
stand for a radical selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2.6)-dimethylhept-4-yl, 3-methylbutyl, n-hexyl, (3.3)-dimethylbutyl, —CH₂—CH₂—O—CH₃, —CH₂—CH₂—O—C₂H₅, —CH₂—CH₂—CH₂—O—CH₃, ethenyl, propenyl, 2-butenyl, 3-butenyl, 2-pentenyl, and 3-pentenyl;
for a radical selected from the group consisting of 2,3-dihydro-1H-indenyl, cyclopropyl, oxetanyl, cyclobutyl, cyclopentyl, cyclohexyl, cycloheptyl, pyrrolidinyl, piperidinyl, morpholinyl, piperazinyl, azepanyl, diazepanyl, azocanyl, and thiomorpholinyl, each of which can be unsubstituted or optionally substituted by 1, 2, 3, 4, or 5 substituents independently selected from the group consisting of methyl, ethyl, n-propyl, isopropyl, n-butyl, sec-butyl, tert-butyl, isobutyl, —C(=O)—O—CH$_3$, —C(=O)—O—C$_2$H$_5$, —C(=O)—O—CH(CH$_3$)$_2$, and —C(=O)—O—C(CH$_3$)$_3$;

or

R$^8$ and R$^9$ each form, together with the interconnecting nitrogen atom as ring member, a radical selected from the group consisting of 3-azabicyclo[3.1.1]heptyl, 6-azaspiro[2.5]octyl, 3-acabicyclo[3.2.1]octyl, 6-azabicyclo[3.3.1]heptyl, 8-acabicyclo[3.2.1]octyl, 1-oxa-2,8-diazaspiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, piperazinyl, morpholinyl, azepanyl, diazepanyl, and thiomorpholinyl, each of which is unsubstituted or optionally substituted by 1, 2, 3, 4, or 5 substituents independently selected from the group consisting of phenethyl, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]phenyl, —N—[C(=O)—CH$_3$]-phenyl, —CH$_2$—O—CH$_3$, —CH$_2$—O—CH$_2$—CH$_3$, oxo (=O), thioxo (=S), —OH, —O—CH$_3$, —O—C$_2$H$_5$, —O—CH(CH$_3$)$_2$, —O—C(CH$_3$)$_3$, —NH$_2$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), phenyl and benzyl, and the cyclic moiety of the radicals phenethyl, —N—[C(=O)—C$_2$H$_5$]phenyl, —N—[C(=O)—CH$_3$]phenyl, phenyl, and benzyl can in each case be substituted by 1, 2, 3, 4, or 5 substituents independently selected from the group consisting of F, Cl, Br, —CF$_3$, methyl, ethyl, n-propyl, isopropyl, n-butyl, sec-butyl, isobutyl, tert-butyl, —O—CH$_3$, and —O—C$_2$H$_5$;

R$^{12}$, R$^{13}$, R$^{14}$, R$^{15}$, and R$^{16}$ each independently stand for H; F; Cl; Br or —CF$_3$;

and

R$^{17}$ stands for hydrogen or for a radical selected from the group consisting of methyl, ethyl, n-propyl, isopropyl, n-butyl, sec-butyl, isobutyl, and tert-butyl;

each optionally in the form of one of the pure stereoisomers thereof, particularly enantiomers or diastereoisomers thereof, the racemates thereof or in the form of a mixture of stereoisomers, particularly the enantiomers and/or diastereoisomers, in an arbitrary mixing ratio, or each in the form of corresponding salts, or each in the form of corresponding solvates.

Very special preference is given to compounds of the general formula Ia,

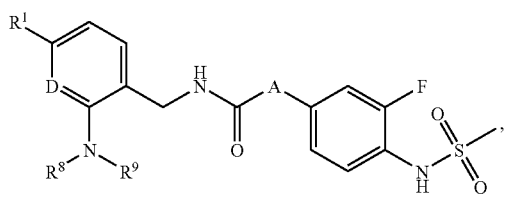

Ia in which

A has the aforementioned meaning;

D stands for N or CH;

R$^1$ stands for —SF$_5$; —O—CF$_3$; —CF$_3$; or for a tert-butyl radical;

R$^3$, R$^4$, R$^5$, and R$^6$ each independently stand for H; F; Cl; Br; —NO$_2$; —CF$_3$; —CN; —OH; methyl; ethyl; isopropyl; n-propyl; n-butyl; tert-butyl; sec-butyl; isobutyl, —O-phenyl; —O—CH$_3$ or —O—C$_2$H$_5$;

R$^8$ and R$^9$ each form, together with the interconnecting nitrogen atom as ring member, a radical selected from the group consisting of azocanyl, pyrrolidinyl, piperidinyl, piperazinyl, morpholinyl, azepanyl, diazepanyl, and thiomorpholinyl, each of which can be unsubstituted or optionally substituted by 1, 2, 3, 4, or 5 substituents independently selected from the group consisting of methyl, ethyl, n-propyl, isopropyl, n-butyl, sec-butyl, isobutyl, tert-butyl, and n-pentyl;

R$^{12}$, R$^{13}$, R$^{14}$, R$^{15}$, and R$^{16}$ each stand for H;

and

R$^{17}$ stands for hydrogen or for a radical selected from the group consisting of methyl, ethyl, n-propyl, isopropyl, n-butyl, sec-butyl, isobutyl, and tert-butyl;

each optionally in the form of one of the pure stereoisomers thereof, particularly enantiomers or diastereoisomers thereof, the racemates thereof or in the form of a mixture of stereoisomers, particularly the enantiomers and/or diastereoisomers, in an arbitrary mixing ratio, or each in the form of corresponding salts, or each in the form of corresponding solvates.

Very special preference is given to compounds of the general formula Ia1, Ia2, Ia3, and Ia4,

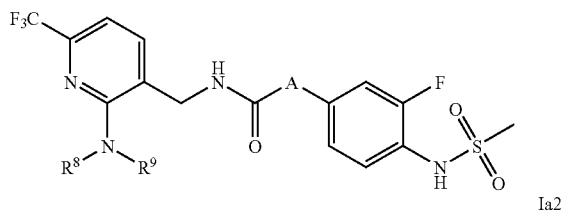

Ia1

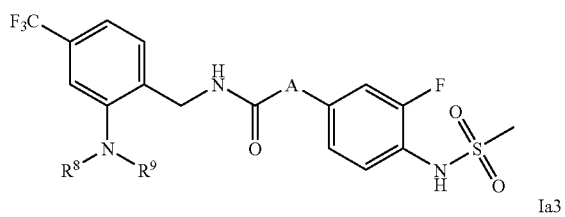

Ia2

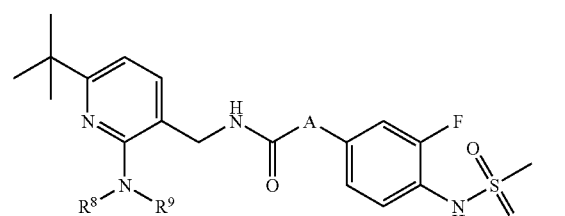

Ia3

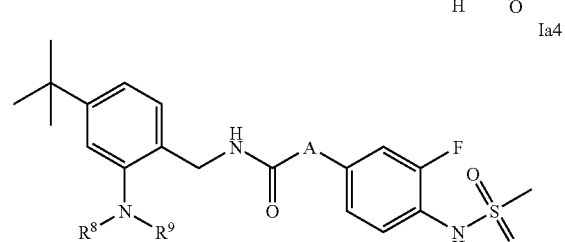

Ia4 in which, in each case,

A has the aforementioned meaning;

$R^3$, $R^4$, $R^5$, and $R^6$ each independently
stand for H; F; Cl; Br; —NO$_2$; —CF$_3$; —CN; —OH; methyl; ethyl; isopropyl; n-propyl; n-butyl; tert-butyl; sec-butyl; isobutyl, —O-phenyl; —O—CH$_3$ or —O—C$_2$H$_5$;

$R^8$ and $R^9$
each form, together with the interconnecting nitrogen atom as ring member, a radical selected from the group consisting of azocanyl, pyrrolidinyl, piperidinyl, piperazinyl, morpholinyl, azepanyl, diazepanyl, and thiomorpholinyl, each of which can be unsubstituted or optionally substituted by 1, 2, 3, 4, or 5 substituents independently selected from the group consisting of methyl, ethyl, n-propyl, isopropyl, n-butyl, sec-butyl, isobutyl, tert-butyl, and n-pentyl;

$R^{12}$, $R^{13}$, $R^{14}$, $R^{15}$, and $R^{16}$ each stand for H; and $R^{17}$ stands for hydrogen or for a radical selected from the group consisting of methyl, ethyl, n-propyl, isopropyl, n-butyl, sec-butyl, isobutyl, and tert-butyl;

each optionally in the form of one of the pure stereoisomers thereof, particularly enantiomers or diastereoisomers thereof, the racemates thereof or in the form of a mixture of stereoisomers, particularly the enantiomers and/or diastereoisomers, in an arbitrary mixing ratio, or each in the form of corresponding salts, or each in the form of corresponding solvates.

Special preference is given to compounds of the general formula Ib,

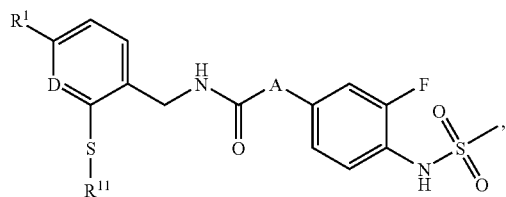

in which

A has the aforementioned meaning;

D stands for N or CH;

$R^1$ stands for —SF$_5$; —O—CF$_3$; —O—CFH$_2$; —O—CF$_2$H; —CFH$_2$; —CF$_2$H; —CF$_3$; or for a tert-butyl radical;

$R^3$, $R^4$, $R^5$, and $R^6$ each independently
stand for H; F; Cl; Br; —NO$_2$; —CF$_3$; —CN; —OH; methyl; ethyl; isopropyl; n-propyl; n-butyl; tert-butyl; sec-butyl; isobutyl, —O-phenyl; —O—CH$_3$ or —O—C$_2$H$_5$;

$R^{11}$ stands for a radical selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethylhept-4-yl, 3-methylbutyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—CH$_2$—O—CH$_3$, ethenyl, propenyl, 2-butenyl, 3-butenyl, 2-pentenyl, and 3-pentenyl;

for a radical selected from the group consisting of 2,3-dihydro-1H-indenyl, cyclopropyl, oxetanyl, cyclobutyl, cyclopentyl, cyclohexyl, cycloheptyl, pyrrolidinyl, piperidinyl, morpholinyl, piperazinyl, azepanyl, diazepanyl, azocanyl, and thiomorpholinyl, each of which can be unsubstituted or optionally substituted by 1, 2, 3, 4, or 5 substituents independently selected from the group consisting of methyl, ethyl, n-propyl, isopropyl, n-butyl, sec-butyl, isobutyl, tert-butyl, —C(=O)—O—CH$_3$, —C(=O)—O—C$_2$H$_5$, —C(=O)—O—CH(CH$_3$)$_2$, and —C(=O)—O—C(CH$_3$)$_3$;

$R^{12}$, $R^{13}$, $R^{14}$, $R^{15}$, and $R^{16}$ each independently stand for H; F; Cl; Br or —CF$_3$;

and $R^{17}$ stands for hydrogen or for a radical selected from the group consisting of methyl, ethyl, n-propyl, isopropyl, n-butyl, sec-butyl, isobutyl, and tert-butyl;

each optionally in the form of one of the pure stereoisomers thereof, particularly enantiomers or diastereoisomers thereof, the racemates thereof or in the form of a mixture of stereoisomers, particularly the enantiomers and/or diastereoisomers, in an arbitrary mixing ratio, or each in the form of corresponding salts, or each in the form of corresponding solvates.

Special preference is given to compounds of the general formulas Ib1, Ib2, Ib3, and Ib4,

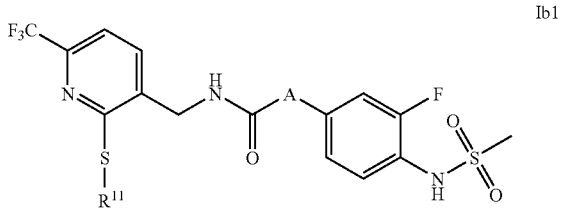

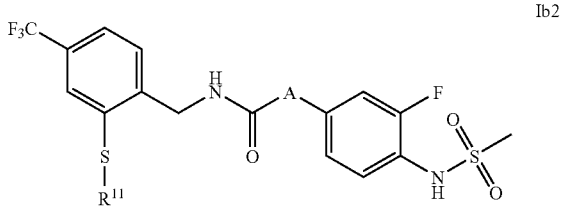

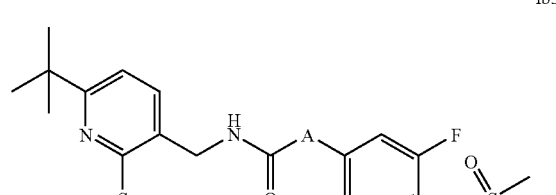

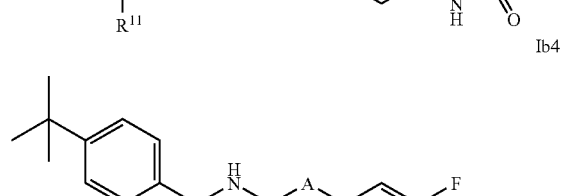

in which, in each case,

A has the aforementioned meaning;

$R^3$, $R^4$, $R^5$, and $R^5$ each independently
stand for H; F; Cl; Br; —NO$_2$; —CF$_3$; —CN; —OH; and methyl; ethyl; isopropyl; n-propyl; n-butyl; tert-butyl; sec-butyl; isobutyl, —O-phenyl; —O—CH$_3$ or —O—C$_2$H$_5$;

$R^{11}$ stands for a radical selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethylhept-4-yl, 3-methylbutyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—CH$_2$—O—CH$_3$, ethenyl, propenyl, 2-butenyl, 3-butenyl, 2-pentenyl, and 3-pentenyl;

for a radical selected from the group consisting of 2,3-dihydro-1H-indenyl, cyclopropyl, oxetanyl, cyclobutyl, cyclopentyl, cyclohexyl, cycloheptyl, pyrrolidinyl, piperidinyl, morpholinyl, piperazinyl, azepanyl, diazepanyl, azocanyl, and thiomorpholinyl, each of which can be unsubstituted or optionally substituted by 1, 2, 3, 4, or 5 substituents independently selected from the group consisting of methyl, ethyl, n-propyl, isopropyl, n-butyl, sec-butyl, isobutyl, tert-butyl, —C(=O)—O—CH$_3$, —C(=O)—O—C$_2$H$_5$, —C(=O)—O—CH(CH$_3$)$_2$, and —C(=O)—O—C(CH$_3$)$_3$;

$R^{12}$, $R^{13}$, $R^{14}$, $R^{15}$, and $R^{16}$ each independently stand for H; F; Cl; Br or —CF$_3$;

and $R^{17}$ stands for hydrogen or for a radical selected from the group consisting of methyl, ethyl, n-propyl, isopropyl, n-butyl, sec-butyl, isobutyl, and tert-butyl;

each optionally in the form of one of the pure stereoisomers thereof, particularly enantiomers or diastereoisomers thereof, the racemates thereof or in the form of a mixture of stereoisomers, particularly the enantiomers and/or diastereoisomers, in an arbitrary mixing ratio, or each in the form of corresponding salts, or each in the form of corresponding solvates.

Very special preference is given to compounds of the general formula Ib,

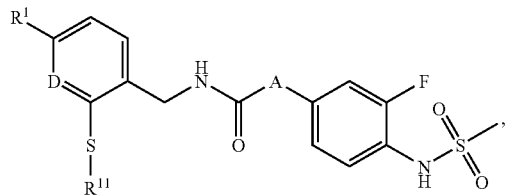

in which

A has the aforementioned meaning;

D stands for N or CH;

$R^1$ stands for —SF$_5$; —O—CF$_3$; —CF$_3$; or for a tert-butyl radical;

$R^3$, $R^4$, $R^5$, and $R^6$ each independently stand for H; F; Cl; Br; —NO$_2$; —CF$_3$; —CN; —OH; methyl; ethyl; isopropyl; n-propyl; n-butyl; tert-butyl; sec-butyl; isobutyl, —O-phenyl; —O—CH$_3$ or —O—C$_2$H$_5$;

$R^{11}$ stands for a radical selected from the group consisting of cyclopropyl, cyclobutyl, cyclopentyl, cyclohexyl, and cycloheptyl, each of which can be unsubstituted or optionally substituted by 1, 2, 3, 4, or 5 substituents independently selected from the group consisting of methyl, ethyl, n-propyl, isopropyl, n-butyl, isobutyl, tert-butyl, and sec-butyl;

$R^{12}$, $R^{13}$, $R^{14}$, $R^{15}$, and $R^{16}$ each stand for H;

and $R^{17}$ stands for hydrogen or for a radical selected from the group consisting of methyl, ethyl, n-propyl, isopropyl, n-butyl, sec-butyl, isobutyl, and tert-butyl;

each optionally in the form of one of the pure stereoisomers thereof, particularly enantiomers or diastereoisomers thereof, the racemates thereof or in the form of a mixture of stereoisomers, particularly the enantiomers and/or diastereoisomers, in an arbitrary mixing ratio, or each in the form of corresponding salts, or each in the form of corresponding solvates.

Very special preference is given to compounds of the general formula Ib1, Ib2, Ib3, and Ib4,

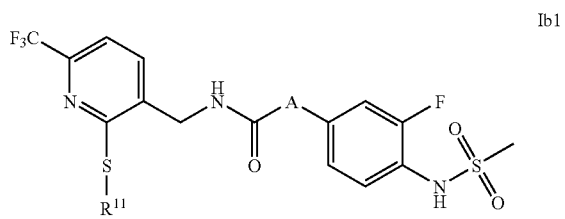

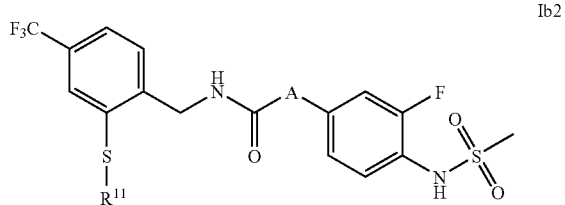

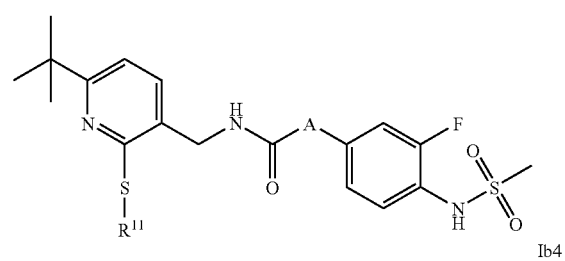

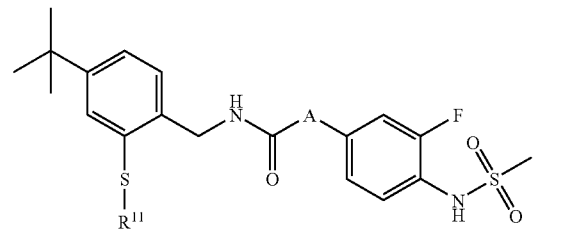

in which, in each case

A has the aforementioned meaning;

$R^3$, $R^4$, $R^5$, and $R^6$ each independently stand for H; F; Cl; Br; —NO$_2$; —CF$_3$; —CN; —OH; and methyl; ethyl; isopropyl; n-propyl; n-butyl; tert-butyl; sec-butyl; isobutyl, —O-phenyl; —O—CH$_3$ or —O—C$_2$H$_5$;

$R^{11}$ stands for a radical selected from the group consisting of cyclopropyl, cyclobutyl, cyclopentyl, cyclohexyl, and cycloheptyl, each of which can be unsubstituted or optionally substituted by 1, 2, 3, 4, or 5 substituents independently selected from the group consisting of methyl, ethyl, n-propyl, isopropyl, n-butyl, sec-butyl, isobutyl, and tert-butyl;

$R^{12}$, $R^{13}$, $R^{14}$, $R^{15}$, and $R^{16}$ each stand for H;
and
$R^{17}$ stands for hydrogen or for a radical selected from the group consisting of methyl, ethyl, n-propyl, isopropyl, n-butyl, sec-butyl, isobutyl, and tert-butyl;
each optionally in the form of one of the pure stereoisomers thereof, particularly enantiomers or diastereoisomers thereof, the racemates thereof or in the form of a mixture of stereoisomers, particularly the enantiomers and/or diastereoisomers, in an arbitrary mixing ratio, or each in the form of corresponding salts, or each in the form of corresponding solvates.

In another preferred embodiment, the present invention relates to compounds of the general formulas A, B, C and D

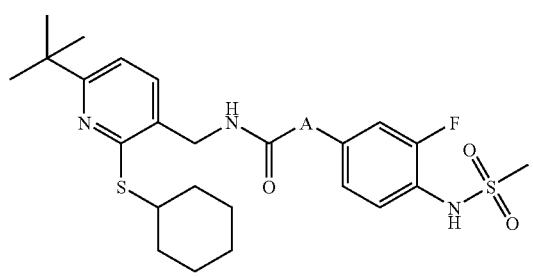

A

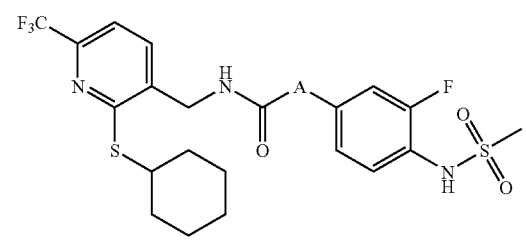

B

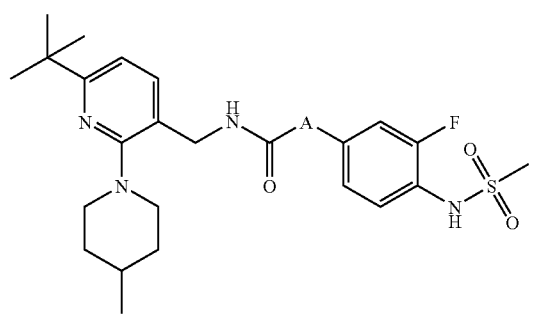

C

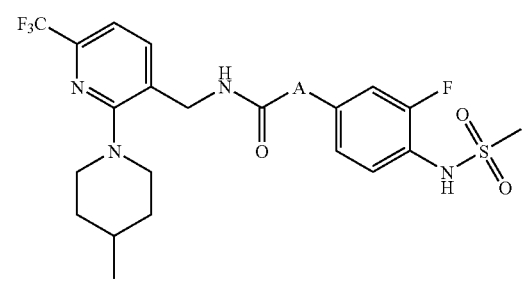

D in which
A is selected from the group consisting of

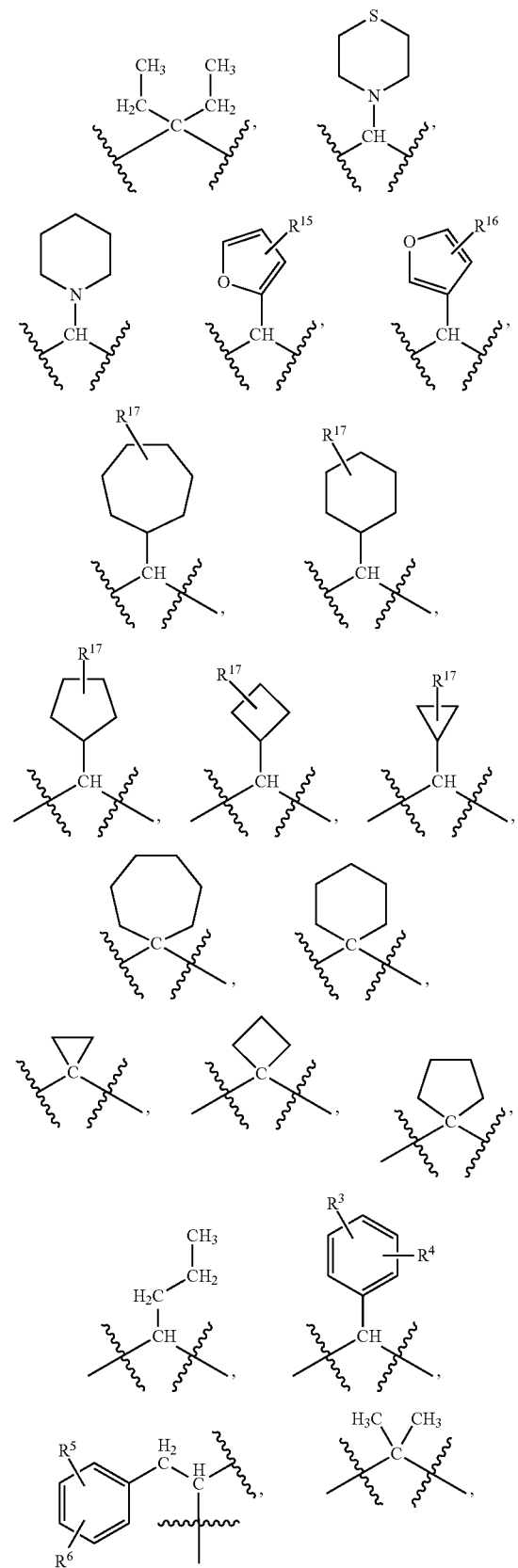

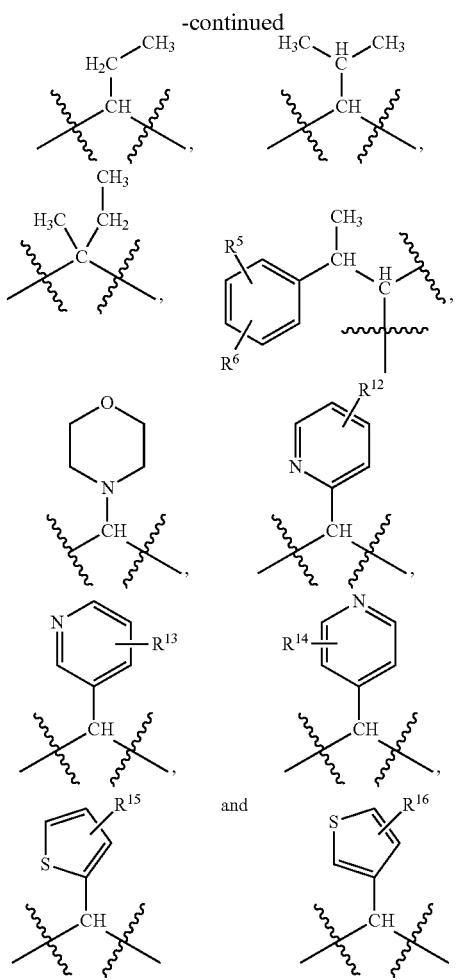

$R^3$, $R^4$, $R^5$, and $R^6$ each independently stand for H; F; Cl; Br; —NO$_2$; —CF$_3$; —CN; —OH; methyl; ethyl; isopropyl; n-propyl; n-butyl; tert-butyl; isobutyl, sec-butyl; —O-phenyl; —O—CH$_3$, or —O—C$_2$H$_5$;

$R^{12}$, $R^{13}$, $R^{14}$, $R^{15}$, and $R^{16}$ each independently stand for H; F; Cl; Br or —CF$_3$; and $R^{17}$ stands for hydrogen or for a radical selected from the group consisting of methyl, ethyl, n-propyl, isopropyl, n-butyl, sec-butyl, isobutyl, and tert-butyl.

Particularly preferred compounds of the general formulas I, Ia1, Ia2, Ia3, Ia4, Ib1, Ib2, Ib3, Ib4, Ic, Id, Ie, If, Ia und Ib are those selected from the group consisting of

[1] 2-Cyclohexyl-2-(3-fluoro-4-(methylsulfonamido)phenyl)-N-((2-(4-methylpiperidin-1-yl)-6-(trifluoromethyl)pyridin-3-yl)methyl)acetamide,

[2] 2-Cyclohexyl-N-((2-(cyclohexylthio)-6-(trifluoromethyl)pyridin-3-yl)methyl)-2-(3-fluoro-4-(methylsulfonamido)phenyl)acetamide,

[3] 2-(3-Fluoro-4-(methylsulfonamido)phenyl)-N-((2-(4-methylpiperidin-1-yl)-6-(trifluoromethyl)pyridin-3-yl)methyl)-2-phenylacetamide,

[4] N-((2-(Cyclohexylthio)-6-(trifluoromethyl)pyridin-3-yl)methyl)-2-(3-fluoro-4-(methylsulfonamido)phenyl)-2-phenylacetamide,

[5] 2-(3-Fluoro-4-(methylsulfonamido)phenyl)-2-methyl-N-((2-(4-methylpiperidin-1-yl)-6-(trifluoromethyl)pyridin-3-yl)methyl)propanamide,

[6] N-((2-(Cyclohexylthio)-6-(trifluoromethyl)pyridin-3-yl)methyl)-2-(3-fluoro-4-(methylsulfonamido)phenyl)-2-methylpropanamide,

[7] 2-(3-Fluoro-4-(methylsulfonamido)phenyl)-2-methyl-N-((2-(4-methylpiperidin-1-yl)-6-(trifluoromethyl)pyridin-3-yl)methyl)butanamide,

[8] N-((2-(Cyclohexylthio)-6-(trifluoromethyl)pyridin-3-yl)methyl)-2-(3-fluoro-4-(methylsulfonamido)phenyl)-2-methylbutanamide,

[9] 1-(3-Fluoro-4-(methylsulfonamido)phenyl)-N-((2-(4-methylpiperidin-1-yl)-6-(trifluoromethyl)pyridin-3-yl)methyl)cyclopropanecarboxamide,

[10] N-((2-(Cyclohexylthio)-6-(trifluoromethyl)pyridin-3-yl)methyl)-1-(3-fluoro-4-(methylsulfonamido)phenyl)cyclopropanecarboxamide,

[11] 1-(3-Fluoro-4-(methylsulfonamido)phenyl)-N-((2-(4-methylpiperidin-1-yl)-6-(trifluoromethyl)pyridin-3-yl)methyl)cyclobutanecarboxamide,

[12] N-((2-(Cyclohexylthio)-6-(trifluoromethyl)pyridin-3-yl)methyl)-1-(3-fluoro-4-(methylsulfonamido)phenyl)cyclobutanecarboxamide,

[13] 1-(3-Fluoro-4-(methylsulfonamido)phenyl)-N-((2-(4-methylpiperidin-1-yl)-6-(trifluoromethyl)pyridin-3-yl)methyl)cyclopentanecarboxamide,

[14] N-((2-(Cyclohexylthio)-6-(trifluoromethyl)pyridin-3-yl)methyl)-1-(3-fluoro-4-(methylsulfonamido)phenyl)cyclopentanecarboxamide,

[15] 1-(3-Fluoro-4-(methylsulfonamido)phenyl)-N-((2-(4-methylpiperidin-1-yl)-6-(trifluoromethyl)pyridin-3-yl)methyl)cyclohexanecarboxamide,

[16] N-((2-(Cyclohexylthio)-6-(trifluoromethyl)pyridin-3-yl)methyl)-1-(3-fluoro-4-(methylsulfonamido)phenyl)cyclohexanecarboxamide,

[17] 2-Cyclopropyl-2-(3-fluoro-4-(methylsulfonamido)phenyl)-N-((2-(4-methylpiperidin-1-yl)-6-(trifluoromethyl)pyridin-3-yl)methyl)acetamide,

[18] N-((2-(Cyclohexylthio)-6-(trifluoromethyl)pyridin-3-yl)methyl)-2-cyclopropyl-2-(3-fluoro-4-(methylsulfonamido)phenyl)acetamide,

[19] 2-Cyclobutyl-2-(3-fluoro-4-(methylsulfonamido)phenyl)-N-((2-(4-methylpiperidin-1-yl)-6-(trifluoromethyl)pyridin-3-yl)methyl)acetamide,

[20] 2-Cyclobutyl-N-((2-(cyclohexylthio)-6-(trifluoromethyl)pyridin-3-yl)methyl)-2-(3-fluoro-4-(methylsulfonamido)phenyl)acetamide,

[21] 2-Cyclopentyl-2-(3-fluoro-4-(methylsulfonamido)phenyl)-N-((2-(4-methylpiperidin-1-yl)-6-(trifluoromethyl)pyridin-3-yl)methyl)acetamide,

[22] N-((2-(Cyclohexylthio)-6-(trifluoromethyl)pyridin-3-yl)methyl)-2-cyclopentyl-2-(3-fluoro-4-(methylsulfonamido)phenyl)acetamide,

[23] 2-(3-Fluoro-4-(methylsulfonamido)phenyl)-N-((2-(4-methylpiperidin-1-yl)-6-(trifluoromethyl)pyridin-3-yl)methyl)-2-morpholinoacetamide,

[24] N-((6-tert-Butyl-2-(4-methylpiperidin-1-yl)pyridin-3-yl)methyl)-2-(3-fluoro-4-(methylsulfonamido)phenyl)-2-phenylacetamide,

[25] 2-(3-Fluoro-4-(methylsulfonamido)phenyl)-N-(2-(4-methylpiperidin-1-yl)-4-(trifluoromethyl)benzyl)-2-phenylacetamide,

[26] N-(4-tert-Butyl-2-(4-methylpiperidin-1-yl)benzyl)-2-(3-fluoro-4-(methylsulfonamido)phenyl)-2-phenylacetamide,

[27] 2-(3-Fluoro-4-(methylsulfonamido)phenyl)-N-((2-(4-methylpiperidin-1-yl)-6-(trifluoromethyl)pyridin-3-yl)methyl)-2-(pyridin-2-yl)acetamide,

[28] 2-(3-Fluoro-4-(methylsulfonamido)phenyl)-N-((2-(4-methylpiperidin-1-yl)-6-(trifluoromethyl)pyridin-3-yl)methyl)-2-(pyridin-3-yl)acetamide,
[29] 2-(3-Fluoro-4-(methylsulfonamido)phenyl)-N-((2-(4-methylpiperidin-1-yl)-6-(trifluoromethyl)pyridin-3-yl)methyl)-2-(pyridin-4-yl)acetamide,
[30] N-((2-(Cyclohexylthio)-6-(trifluoromethyl)pyridin-3-yl)methyl)-2-(3-fluoro-4-(methylsulfonamido)phenyl)-2-(pyridin-2-yl)acetamide,
[31] N-((2-(Cyclohexylthio)-6-(trifluoromethyl)pyridin-3-yl)methyl)-2-(3-fluoro-4-(methylsulfonamido)phenyl)-2-(pyridin-3-yl)acetamide,
[32] N-((2-(Cyclohexylthio)-6-(trifluoromethyl)pyridin-3-yl)methyl)-2-(3-fluoro-4-(methylsulfonamido)phenyl)-2-(pyridin-4-yl)acetamide,
[33] 2-(3-Fluoro-4-(methylsulfonamido)phenyl)-2-(2-fluorophenyl)-N-((2-(4-methylpiperidin-1-yl)-6-(trifluoromethyl)pyridin-3-yl)methyl)acetamide,
[34] 2-(3-Fluoro-4-(methylsulfonamido)phenyl)-2-(3-fluorophenyl)-N-((2-(4-methylpiperidin-1-yl)-6-(trifluoromethyl)pyridin-3-yl)methyl)acetamide,
[35] 2-(3-Fluoro-4-(methylsulfonamido)phenyl)-2-(4-fluorophenyl)-N-((2-(4-methylpiperidin-1-yl)-6-(trifluoromethyl)pyridin-3-yl)methyl)acetamide,
[36] 2-(3-Chlorophenyl)-2-(3-fluoro-4-(methylsulfonamido)phenyl)-N-((2-(4-methylpiperidin-1-yl)-6-(trifluoromethyl)pyridin-3-yl)methyl)acetamide,
[37] 2-(4-Chlorophenyl)-2-(3-fluoro-4-(methylsulfonamido)phenyl)-N-((2-(4-methylpiperidin-1-yl)-6-(trifluoromethyl)pyridin-3-yl)methyl)acetamide,
[38] 2-(3-Bromophenyl)-2-(3-fluoro-4-(methylsulfonamido)phenyl)-N-((2-(4-methylpiperidin-1-yl)-6-(trifluoromethyl)pyridin-3-yl)methyl)acetamide,
[39] 2-(4-Bromophenyl)-2-(3-fluoro-4-(methylsulfonamido)phenyl)-N-((2-(4-methylpiperidin-1-yl)-6-(trifluoromethyl)pyridin-3-yl)methyl)acetamide,
[40] 2-(3-Fluoro-4-(methylsulfonamido)phenyl)-N-((2-(4-methylpiperidin-1-yl)-6-(trifluoromethyl)pyridin-3-yl)methyl)-2-o-tolylacetamide,
[41] 2-(3-Fluoro-4-(methylsulfonamido)phenyl)-N-((2-(4-methylpiperidin-1-yl)-6-(trifluoromethyl)pyridin-3-yl)methyl)-2-m-tolylacetamide,
[42] 2-(3-Fluoro-4-(methylsulfonamido)phenyl)-N-((2-(4-methylpiperidin-1-yl)-6-(trifluoromethyl)pyridin-3-yl)methyl)-2-p-tolylacetamide,
[43] 2-(3-Fluoro-4-(methylsulfonamido)phenyl)-N-((2-(4-methylpiperidin-1-yl)-6-(trifluoromethyl)pyridin-3-yl)methyl)-2-(3-(trifluoromethyl)phenyl)acetamide,
[44] 2-(3-Fluoro-4-(methylsulfonamido)phenyl)-N-((2-(4-methylpiperidin-1-yl)-6-(trifluoromethyl)pyridin-3-yl)methyl)-2-(4-(trifluoromethyl)phenyl)acetamide,
[45] 2-(3-Fluoro-4-(methylsulfonamido)phenyl)-2-(4-hydroxyphenyl)-N-((2-(4-methylpiperidin-1-yl)-6-(trifluoromethyl)pyridin-3-yl)methyl)acetamide,
[46] 2-(3-Fluoro-4-(methylsulfonamido)phenyl)-2-(4-methoxyphenyl)-N-((2-(4-methylpiperidin-1-yl)-6-(trifluoromethyl)pyridin-3-yl)methyl)acetamide,
[47] 2-(3-Fluoro-4-(methylsulfonamido)phenyl)-2-(3-hydroxy-4-methoxyphenyl)-N-((2-(4-methylpiperidin-1-yl)-6-(trifluoromethyl)pyridin-3-yl)methyl)acetamide,
[48] 2-(3-Fluoro-4-(methylsulfonamido)phenyl)-2-(4-hydroxy-3-methoxyphenyl)-N-((2-(4-methylpiperidin-1-yl)-6-(trifluoromethyl)pyridin-3-yl)methyl)acetamide,
[49] 2-(3-Fluoro-4-(methylsulfonamido)phenyl)-N-((2-(4-methylpiperidin-1-yl)-6-(trifluoromethyl)pyridin-3-yl)methyl)-2-(4-phenoxyphenyl)acetamide,
[50] 2-(3-Fluoro-4-(methylsulfonamido)phenyl)-N-((2-(4-methylpiperidin-1-yl)-6-(trifluoromethyl)pyridin-3-yl)methyl)-2-(thiophen-2-yl)acetamide,
[51] 2-(3-Fluoro-4-(methylsulfonamido)phenyl)-N-((2-(4-methylpiperidin-1-yl)-6-(trifluoromethyl)pyridin-3-yl)methyl)-2-(thiophen-3-yl)acetamide,
[52] N-((2-(Cyclohexylthio)-6-(trifluoromethyl)pyridin-3-yl)methyl)-2-(3-fluoro-4-(methylsulfonamido)phenyl)-2-(2-fluorophenyl)acetamide,
[53] N-((2-(Cyclohexylthio)-6-(trifluoromethyl)pyridin-3-yl)methyl)-2-(3-fluoro-4-(methylsulfonamido)phenyl)-2-(3-fluorophenyl)acetamide,
[54] N-((2-(Cyclohexylthio)-6-(trifluoromethyl)pyridin-3-yl)methyl)-2-(3-fluoro-4-(methylsulfonamido)phenyl)-2-(4-fluorophenyl)acetamide,
[55] 2-(3-Chlorophenyl)-N-((2-(cyclohexylthio)-6-(trifluoromethyl)pyridin-3-yl)methyl)-2-(3-fluoro-4-(methylsulfonamido)phenyl)acetamide,
[56] 2-(4-Chlorophenyl)-N-((2-(cyclohexylthio)-6-(trifluoromethyl)pyridin-3-yl)methyl)-2-(3-fluoro-4-(methylsulfonamido)phenyl)acetamide,
[57] 2-(3-Bromophenyl)-N-((2-(cyclohexylthio)-6-(trifluoromethyl)pyridin-3-yl)methyl)-2-(3-fluoro-4-(methylsulfonamido)phenyl)acetamide,
[58] 2-(4-Bromophenyl)-N-((2-(cyclohexylthio)-6-(trifluoromethyl)pyridin-3-yl)methyl)-2-(3-fluoro-4-(methylsulfonamido)phenyl)acetamide,
[59] N-((2-(Cyclohexylthio)-6-(trifluoromethyl)pyridin-3-yl)methyl)-2-(3-fluoro-4-(methylsulfonamido)phenyl)-2-o-tolylacetamide,
[60] N-((2-(Cyclohexylthio)-6-(trifluoromethyl)pyridin-3-yl)methyl)-2-(3-fluoro-4-(methylsulfonamido)phenyl)-2-m-tolylacetamide,
[61] N-((2-(Cyclohexylthio)-6-(trifluoromethyl)pyridin-3-yl)methyl)-2-(3-fluoro-4-(methylsulfonamido)phenyl)-2-p-tolylacetamide,
[62] N-((2-(Cyclohexylthio)-6-(trifluoromethyl)pyridin-3-yl)methyl)-2-(3-fluoro-4-(methylsulfonamido)phenyl)-2-(3-(trifluoromethyl)phenyl)acetamide,
[63] N-((2-(Cyclohexylthio)-6-(trifluoromethyl)pyridin-3-yl)methyl)-2-(3-fluoro-4-(methylsulfonamido)phenyl)-2-(4-(trifluoromethyl)phenyl)acetamide,
[64] N-((2-(Cyclohexylthio)-6-(trifluoromethyl)pyridin-3-yl)methyl)-2-(3-fluoro-4-(methylsulfonamido)phenyl)-2-(4-hydroxyphenyl)acetamide,
[65] N-((2-(Cyclohexylthio)-6-(trifluoromethyl)pyridin-3-yl)methyl)-2-(3-fluoro-4-(methylsulfonamido)phenyl)-2-(4-methoxyphenyl)acetamide,
[66] N-((2-(Cyclohexylthio)-6-(trifluoromethyl)pyridin-3-yl)methyl)-2-(3-fluoro-4-(methylsulfonamido)phenyl)-2-(3-hydroxy-4-methoxyphenyl)acetamide,
[67] N-((2-(Cyclohexylthio)-6-(trifluoromethyl)pyridin-3-yl)methyl)-2-(3-fluoro-4-(methylsulfonamido)phenyl)-2-(4-hydroxy-3-methoxyphenyl)acetamide,
[68] N-((2-(Cyclohexylthio)-6-(trifluoromethyl)pyridin-3-yl)methyl)-2-(3-fluoro-4-(methylsulfonamido)phenyl)-2-(4-phenoxyphenyl)acetamide,
[69] 2-(3-Fluoro-4-(methylsulfonamido)phenyl)-N-((2-(4-methylpiperidin-1-yl)-6-(trifluoromethyl)pyridin-3-yl)methyl)-2-(thiophen-2-yl)acetamide,
[70] 2-(3-Fluoro-4-(methylsulfonamido)phenyl)-N-((2-(4-methylpiperidin-1-yl)-6-(trifluoromethyl)pyridin-3-yl)methyl)-2-(thiophen-3-yl)acetamide,
[71] N-((2-(Cyclohexylthio)-6-(trifluoromethyl)pyridin-3-yl)methyl)-2-(3-fluoro-4-(methylsulfonamido)phenyl)-2-(thiophen-2-yl)acetamide,

[72] N-((2-(Cyclohexylthio)-6-(trifluoromethyl)pyridin-3-yl)methyl)-2-(3-fluoro-4-(methylsulfonamido)phenyl)-2-(thiophen-3-yl)acetamide,
[73] 2-(3-Fluoro-4-(methylsulfonamido)phenyl)-N-((2-(4-methylpiperidin-1-yl)-6-(trifluoromethyl)pyridin-3-yl)methyl)-3-phenylpropanamide,
[74] 2-(3-Fluoro-4-(methylsulfonamido)phenyl)-N-((2-(4-methylpiperidin-1-yl)-6-(trifluoromethyl)pyridin-3-yl)methyl)-3-phenylbutanamide,
[75] 2-(3-Fluoro-4-(methylsulfonamido)phenyl)-N-((2-(4-methylpiperidin-1-yl)-6-(trifluoromethyl)pyridin-3-yl)methyl)-3-o-tolylpropanamide,
[76] 2-(3-Fluoro-4-(methylsulfonamido)phenyl)-N-((2-(4-methylpiperidin-1-yl)-6-(trifluoromethyl)pyridin-3-yl)methyl)-3-m-tolylpropanamide,
[77] 2-(3-Fluoro-4-(methylsulfonamido)phenyl)-N-((2-(4-methylpiperidin-1-yl)-6-(trifluoromethyl)pyridin-3-yl)methyl)-3-p-tolylpropanamide,
[78] 2-(3-Fluoro-4-(methylsulfonamido)phenyl)-3-(2-fluorophenyl)-N-((2-(4-methylpiperidin-1-yl)-6-(trifluoromethyl)pyridin-3-yl)methyl)propanamide,
[79] 2-(3-Fluoro-4-(methylsulfonamido)phenyl)-3-(3-fluorophenyl)-N-((2-(4-methylpiperidin-1-yl)-6-(trifluoromethyl)pyridin-3-yl)methyl)propanamide,
[80] 2-(3-Fluoro-4-(methylsulfonamido)phenyl)-3-(4-fluorophenyl)-N-((2-(4-methylpiperidin-1-yl)-6-(trifluoromethyl)pyridin-3-yl)methyl)propanamide,
[81] 2-(3-Fluoro-4-(methylsulfonamido)phenyl)-N-((2-(4-methylpiperidin-1-yl)-6-(trifluoromethyl)pyridin-3-yl)methyl)-3-(3-(trifluoromethyl)phenyl)propanamide,
[82] 2-(3-Fluoro-4-(methylsulfonamido)phenyl)-N-((2-(4-methylpiperidin-1-yl)-6-(trifluoromethyl)pyridin-3-yl)methyl)-3-(4-(trifluoromethyl)phenyl)propanamide,
[83] 2-(3-Fluoro-4-(methylsulfonamido)phenyl)-3-(4-hydroxy-3-methoxyphenyl)-N-((2-(4-methylpiperidin-1-yl)-6-(trifluoromethyl)pyridin-3-yl)methyl)propanamide,
[84] N-((2-(Cyclohexylthio)-6-(trifluoromethyl)pyridin-3-yl)methyl)-2-(3-fluoro-4-(methylsulfonamido)phenyl)-3-(2-fluorophenyl)propanamide,
[85] N-((2-(Cyclohexylthio)-6-(trifluoromethyl)pyridin-3-yl)methyl)-2-(3-fluoro-4-(methylsulfonamido)phenyl)-3-(3-fluorophenyl)propanamide,
[86] N-((2-(Cyclohexylthio)-6-(trifluoromethyl)pyridin-3-yl)methyl)-2-(3-fluoro-4-(methylsulfonamido)phenyl)-3-(4-fluorophenyl)propanamide,
[87] N-((2-(Cyclohexylthio)-6-(trifluoromethyl)pyridin-3-yl)methyl)-2-(3-fluoro-4-(methylsulfonamido)phenyl)-3-(3-(trifluoromethyl)phenyl)propanamide,
[88] N-((2-(Cyclohexylthio)-6-(trifluoromethyl)pyridin-3-yl)methyl)-2-(3-fluoro-4-(methylsulfonamido)phenyl)-3-(4-(trifluoromethyl)phenyl)propanamide und
[89] N-((2-(Cyclohexylthio)-6-(trifluoromethyl)pyridin-3-yl)methyl)-2-(3-fluoro-4-(methylsulfonamido)phenyl)-3-(4-hydroxy-3-methoxyphenyl)propanamide;

in each case optionally in the form of one of the pure stereoisomers thereof, particularly enantiomers or diastereoisomers, or the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Furthermore, compounds of the invention of the general formulas I, Ia, Ia1, and Ia2, Ia3, Ia4, Ib1, Ib2, Ib3, Ib4, Ic, Id, and Ie, If, Ib, A, B, C and D can be preferred which cause a 50% displacement of capsaicin present in a concentration of 100 nM, in the FLIPR assay using CHO-K1 cells transfected with the human VR1 gene and present in a concentration below 2000 nM, preferably below 1000 nM, more preferably below 300 nM, even more preferably below 100 nM, still more preferably below 75 nM, very preferably below 50 nM and most preferably below 10 nM.

In the FLIPR assay, the $Ca^{2+}$ inflow is quantified with the aid of a $Ca^{2+}$-sensitive dye (type Fluo-4, Molecular Probes Europe BV, Leiden, Netherlands) in a Fluorescent Imaging Plate Reader (FLIPR, Molecular Devices, Sunnyvale, USA), as described below.

Preferably, the compound 2-(3-fluoro-4-methanesulfonylaminophenyl)-N-(4-methyl-6'-trifluoromethyl-3,4,5,6-tetrahydro-2H-[1,2']bipyridinyl-3'-ylmethyl)-butyramide optionally in the form of one of the pure stereoisomers thereof, particularly enantiomers or diastereoisomers thereof, the racemates thereof or in the form of a mixture of stereoisomers, particularly the enantiomers and/or diastereoisomers, in an arbitrary mixing ratio, or in the form of corresponding salts, or in the form of corresponding solvates, can be excepted.

The invention further relates to a process for the production of compounds of the above general formulas I, Ia, Ia1, Ia2, Ia3, Ia4, Ib, Ib, Ib, Ib, Ic, Id, Ie, If, Ib, A, B, C and D according to which at least one compound of the general formula II,

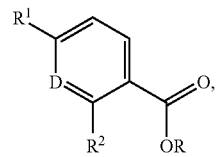

in which $R^1$, $R^2$, and D have the aforementioned meanings and R stands for hydrogen or for a linear or branched $C_{1-6}$ alkyl radical, in a reaction medium, in the presence of at least one reducing agent, preferably in the presence of at least one reducing agent selected from the group consisting of sodium hydride, sodium, potassium hydride, lithium aluminum hydride, sodium tetrahydridoborate, and di(isobutyl)aluminum hydride,
is converted to at least one compound of the general formula III,

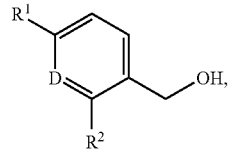

in which $R^1$, $R^2$, and D have the meanings stated above, and this is optionally purified and/or isolated,
and at least one compound of the general formula III is converted, in a reaction medium in the presence of diphenylphosphorylazide or in the presence of $HN_3$, to at least one compound of the general formula IV,

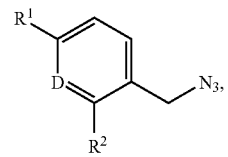

in which $R^1$, $R^2$, and D have the meanings stated above, and this is optionally purified and/or isolated, and at least one compound of the general formula IV is converted, in a reaction medium in the presence of at least one reducing agent, preferably in the presence of at least one reducing agent selected from the group consisting of sodium hydride, potassium hydride, lithium aluminum hydride, sodium tetrahydridoborate, and di(isobutyl)aluminum hydride,
or in a reaction medium in the presence of a catalyst, preferably in the presence of a catalyst based on platinum or palladium, more preferably in the presence of palladium-on-charcoal, and in the presence of hydrogen or in the presence of hydrazine,
or in a reaction medium in the presence of triphenylphosphine to at least one compound of the general formula V,

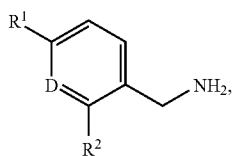

in which $R^1$, $R^2$, and D have the meanings stated above, and this is optionally purified and/or isolated,
or at least one compound of the general formula VI,

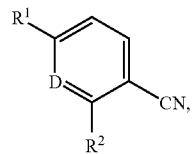

in which $R^1$, $R^2$, and D have the meanings stated above, in a reaction medium
in the presence of at least one catalyst, preferably in the presence of at least one catalyst based on palladium or platinum, more preferably in the presence of palladium-on-charcoal, under a blanket of hydrogen, optionally in the presence of at least one acid, preferably in the presence of hydrochloric acid,
or in the presence of at least one reducing agent selected from the group consisting of $BH_3.S(CH_3)_2$, lithium aluminum hydride, and sodium tetrahydridoborate, optionally in the presence of $NiCl_2$,
is converted to at least one compound of the general formula V, optionally in the form of a corresponding salt, preferably in the form of a corresponding hydrochloride, and this is optionally purified and/or isolated,
and at least one compound of the general formula V is caused to react with at least one compound of the general formula VII,

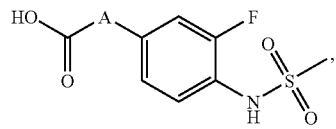

in which A has the aforementioned meaning, in a reaction medium, optionally in the presence of at least one suitable coupling agent, optionally in the presence of at least one base, or with at least one compound of the general formula VIII,

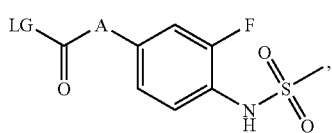

in which A has the aforementioned meaning and LG stands for a leaving group, preferably for or a chlorine radical or bromine atom, in a reaction medium, optionally in the presence of at least one base, to form at least one compound of the general formula I,

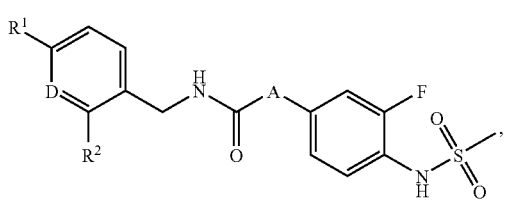

in which $R^1$, $R^2$, D, and A have the meanings stated above, and this is optionally purified and/or isolated.

The reaction of compounds of the above general formula V with carboxylic acids of the above general formula VII to form compounds of the above general formula I is carried out preferably in a reaction medium selected from the group consisting of diethyl ether, tetrahydrofuran, acetonitrile, methanol, ethanol, (1.2)-dichloroethane, dimethylformamide, dichloromethane and appropriate mixtures, optionally in the presence of at least one coupling agent, preferably selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCI), diisoproylcarbodiimide, 1,1'-carbonyl-diimidazole (CDI), N-[(dimethyamino)-1H-1,2,3-triazolo[4,5-b]pyridino-1-ylmethylene]-N-methylmethanaminum hexafluorophosphate N-oxide (HATU), O-(benzotriazol-1-yl)-N,N,N',N'-tetramethyluroniom hexafluorophosphate (HBTU), O-(benzotriazol-1-yl)-N,N,N',N'-tetramethyluronium tetrafluoroborate (TBTU), and 1-hydroxy-7-azabenzotriazole (HOAt), optionally in the presence of at least one organic base, preferably selected from the group consisting of triethylamine, pyridine, dimethylaminopyridine, N-methylmorpholine, and diisopropylethylamine, and preferably at temperatures ranging from −70° C. to 100° C.

Alternatively, the reaction of compounds of the above general formulas V with carboxylic derivatives of the above general formula VIII in which LG stands for a leaving group, preferably for a chlorine radical or bromine atom, to form compounds the above general formulas Ih is carried out in a reaction medium preferably selected from the group consisting of diethyl ether, tetrahydrofuran, acetonitrile, methanol, ethanol, dimethylformamide, dichloromethane and appropriate mixtures, optionally in the presence of an organic or inorganic base, preferably selected from the group consisting of triethylamine, dimethylaminopyridine, pyridine, and diisopropylamine, at temperatures ranging from −70° C. to 100° C.

The compounds of the above formulas II, III, IV, V, VI, and VIII are all commercially available and can be obtained by methods known to the person skilled in the art.

The synthesis of compounds of the general formula VII is described in the publication "4-(Methylsulfonylamino)phenyl analogues as vanilloid antagonist showing excellent analgesic activity and the pharmaceutical compositions comprising the same" by J. W. Lee et al. [WO 2005/003084-A1].

The relevant sections of this reference are included herein by reference and are to be regarded as part of the disclosure.

Compounds of the general formula VII can likewise be obtained as illustrated by the following scheme.

converted to the corresponding ethyl esters of the general formula U. The process is described in U.S. Pat. No. 3,306,909. The relevant sections of this reference are included herein by reference and are to be regarded as part of the disclosure.

In stage 1b, compounds of the general formula S1, in which $R^3$ and $R^4$ have the meanings stated above, are converted, using thionyl chloride, to the corresponding compounds of the general formula T2, which can subsequently be converted to the corresponding ethyl esters of the general formula U. The process is described inter alia in DE 1966974. The relevant sections of this reference are included herein by reference and are to be regarded as part of the disclosure.

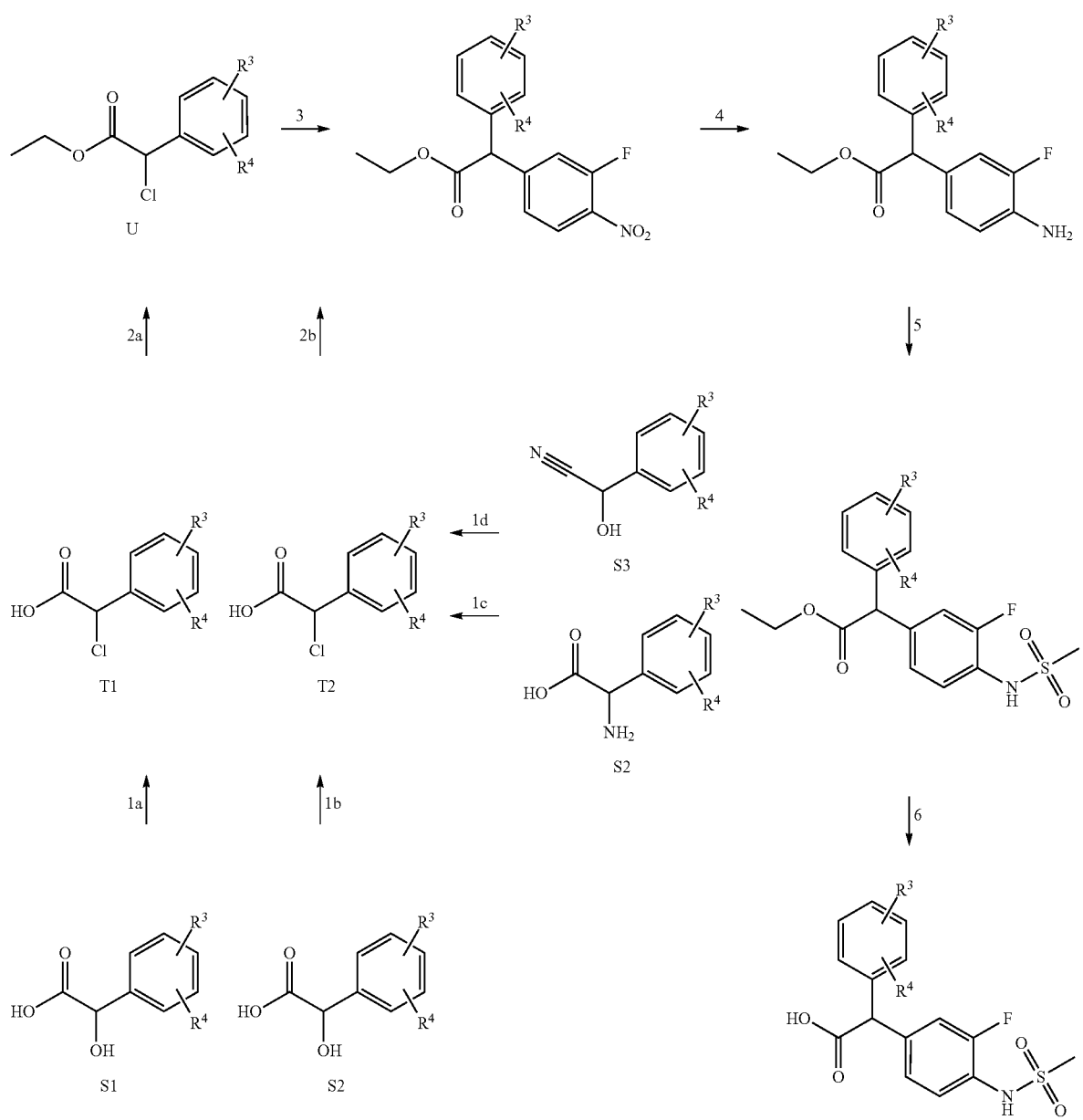

In stage 1a, compounds of the general formula S1, in which $R^3$ and $R^4$ have the meanings stated above, are converted, using phosphorus pentachloride, to the corresponding compounds of the general formula T1, which can subsequently be Compounds of the general formula S2, in which $R^3$ and $R^4$ have the meanings stated above, can be caused to react with $NaNO_2$ and HCl to form the corresponding compounds of the general formula T2, as described in J. CH. SOC. 95, (1909), pages from 780 to 789. The relevant sections of this reference are included herein by reference and are to be regarded as part of the disclosure.

Another possibility of preparing chlorophenylacetic acids of the general formula T2 starting from compounds of the general formula S3, in which $R^3$ and $R^4$ have the meanings stated above is described in Chem. Berichte 14 (1881), page 239. The relevant sections of this reference are included herein by reference and are to be regarded as part of the disclosure.

The esterification of chlorophenylacetic acid of the general formula T2 can be carried out by standard esterification procedures such as are described in J. Prakt. Chem. 99, (1919), page 224; Synthesis 6, (2001), pages 943-946; J. Fluorine Chem. 79, 2, (1996), pages 167-172 and Tetrahedron 52, 44, (1996), pages 13867-13880. The relevant sections of this reference are included herein by reference and are to be regarded as part of the disclosure.

The further conversion in stages 3, 4, 5 and 6 is carried out as described under 6d. Synthesis of 2-(3-fluoro-4-(methylsulfonamido)phenyl)-2-phenylacetic acid.

Compounds of the general formula VII can likewise be obtained as illustrated by the following scheme.

to the corresponding compounds of the general formula W, as described in US 2003/144546. The relevant sections of this reference are included herein by reference and are to be regarded as part of the disclosure.

In stage 1b, compounds of the general formula Y, in which $R^5$ and $R^6$ have the meanings stated above, are converted to the corresponding compounds of the general formula W, as described in Helv. Chim. Acta 66, 4, (1983), pages 1028-1030; J. Am. Chem. Soc. 85, (1963), pages 3394-3396 and Tetrahedron Letters, 28, 17, (1987), pages 1873-1876.

The esterification of chlorophenylpropanoic acid of the general formula W can be carried out by standard esterification procedures such as are described in J. Prakt. Chem. 99, (1919), page 224; synthesis 6, (2001), pages 943-946; J. Fluorine Chem. 79, 2, (1996), pages 167-172 and Tetrahedron 52, 44, (1996), pages 13867-13880.

The relevant sections of this reference are included herein by reference and are to be regarded as part of the disclosure.

Further conversion in stages 3, 4, 5 and 6 is carried out as described under 6d. Synthesis of 2-(3-fluoro-4-(methylsulfonamido)phenyl)-2-phenylacetic acid.

The conversions described above can each be carried out under usual conditions well known to the person skilled in the

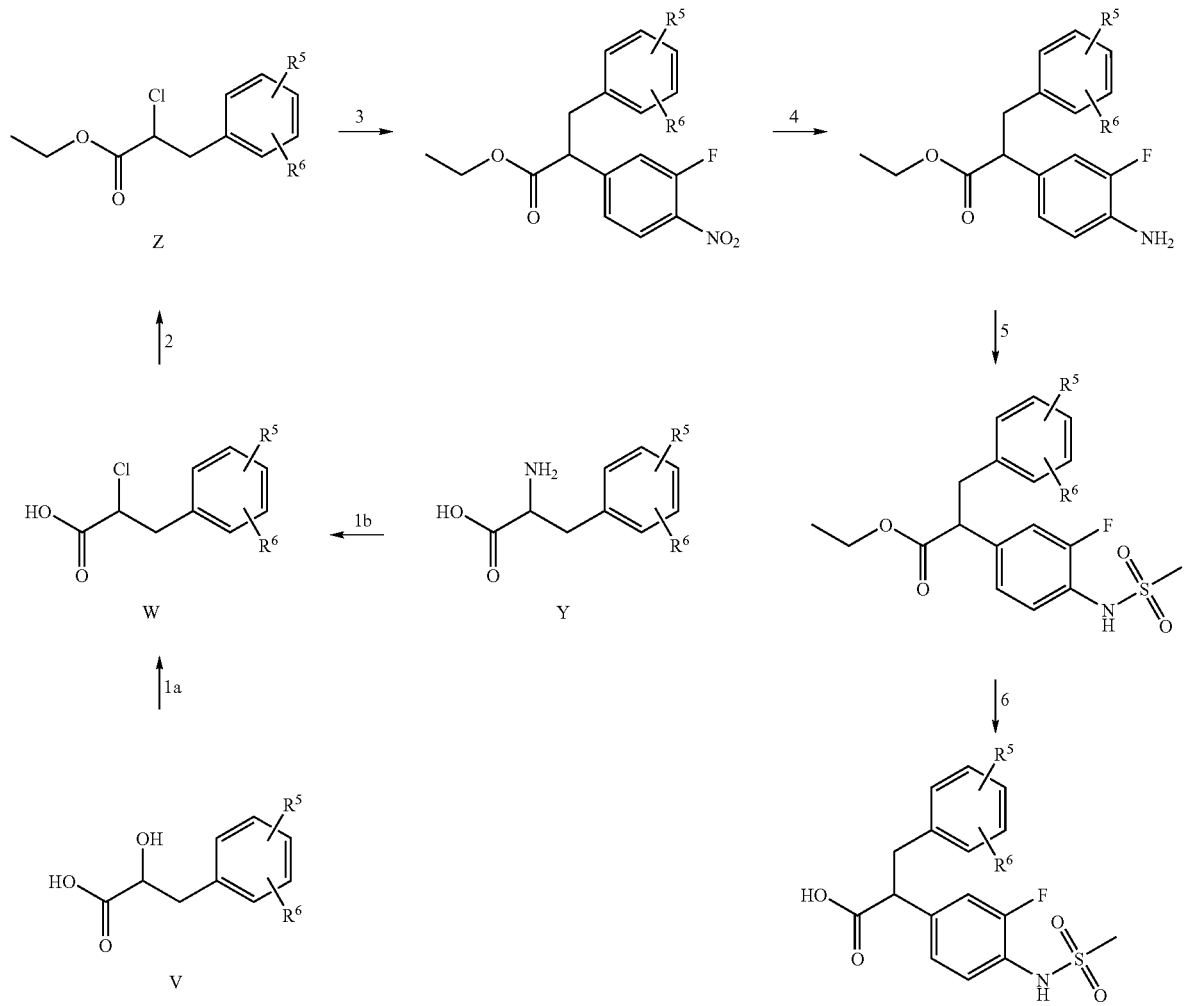

In stage 1a, compounds of the general formula V, in which $R^5$ and $R^6$ have the meanings stated above, can be converted art, for example, in respect of pressure or order of addition of the components. Optionally, the optimal procedure under the respective conditions can be determined by the person skilled in the art using simple preliminary tests. The intermediates and end products obtained by the aforementioned reactions can in each case be isolated and/or purified by conventional methods known to the person skilled in the art, if desired and/or necessary. Suitable clean-up techniques are, for example, extraction processes and chromatographic processes such as column chromatography or preparative chromatography. All of the process steps described above and the purification and/or isolation of intermediate or end products can be carried out partially or completely under a blanket of inert gas, preferably under a blanket of nitrogen.

The substituted compounds of the invention of the aforementioned general formulas I, Ia, Ia1, Ia2, Ia3, Ia4, Ib, Ib, Ib, Ib, Ic, Id, Ie, If, Ib, A, B, C and D—referred to below only as compounds of the general formula I—, and the corresponding stereoisomers can be isolated either in the form of the free bases thereof or the free acids thereof or in the form of corresponding salts, particularly physiologically acceptable salts.

The free bases of the respective substituted compounds of the invention of the aforementioned general formula I and corresponding stereoisomers can, for example by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid, or aspartic acid, be converted to the corresponding salts, preferably physiologically acceptable salts. The free bases of the respective substituted compounds of the aforementioned general formula I and corresponding stereoisomers can be likewise caused to react with the free acid or a salt of a sugar substitute, such as saccharin, cyclamate or acesulfam, to form the corresponding physiologically acceptable salts.

Similarly, the free acids of the substituted compounds of the aforementioned general formula I and corresponding stereoisomers can be caused to react with of a suitable base to form the corresponding physiologically acceptable salts. Mention may be made, for example, of the alkali-metal salts, alkaline earth metal salts, or ammonium salts $[NH_xR_{4-x}]^+$ in which x is equal to 0, 1, 2, 3, or 4 and R stands for a linear or branched $C_{1-4}$ alkyl radical.

The substituted compounds of the invention designated by the aforementioned general formula I and corresponding stereoisomers can optionally, like the corresponding acids, the corresponding bases, or salts of these compounds, be obtained in the form of the solvates thereof, preferably in the form of the hydrates thereof, by conventional methods known to the person skilled in the art.

If the substituted compounds of the invention designated by the aforementioned general formula I are obtained, following production thereof, in the form of a mixture of the stereoisomers thereof, preferably in the form of the racemates thereof or other mixtures of the various enantiomers and/or diastereoisomers thereof, these compounds can be separated and, if desired, isolated by methods known to the person skilled in the art. Mention may be made, for example, of chromatographic separation methods, particularly liquid-chromatographic methods carried out under standard pressure or at elevated pressure, preferably MPLC and HPLC methods, and also methods of fractional crystallization. Particularly individual enantiomers can be separated from each other, e.g., diastereoisomeric salts formed by means of HPLC on chiral stationary phase or by means of crystallization with chiral acids, say, (+)-tartaric acid, (−)-tartaric acid, or (+)-10-camphorsulfonic acid.

The substituted compounds of the invention designated by the aforementioned general formula I and corresponding stereoisomers and in each case the corresponding acids, bases, salts, and solvates are toxicologically safe and are therefore suitable for use as pharmaceutical active substances in medicinal drugs.

The invention therefore further relates to a medicinal drug containing at least one compound of the invention of the above general formula I, each optionally in the form of one of the pure stereoisomers thereof, particularly enantiomers or diastereoisomers thereof, the racemates thereof or in the form of a mixture of stereoisomers, particularly the enantiomers and/or diastereoisomers, in an arbitrary mixing ratio, or each in the form of a corresponding salt, or each in the form of a corresponding solvate, and optionally one or more pharmaceutically compatible adjuvants.

These medicinal drugs of the inventions are particularly suitable for vanilloid receptor 1-(VR1/TRPV1) regulation, preferably vanilloid receptor 1-(VR1/TRPV1) inhibition and/or vanilloid receptor 1-(VR1/TRPV1) stimulation.

In another preferred embodiment, the medicinal drugs of the invention are suitable for prophylaxis and/or treatment of disorders or diseases that are at least partially mediated by vanilloid receptors 1.

Preferably, the medicinal drug of the invention is suitable for treatment and/or prophylaxis of one or more disorders selected from the group consisting of pain selected from the group consisting of acute pain, chronic pain, neuropathic pain and visceral pain; arthralgia; hyperalgesia; allodynia; causalgia; migraine; states of depression; nervous disorders; neurotraumas; neurodegenerative disorders, preferably selected from the group consisting of multiple sclerosis, Morbus Alzheimer, Morbus Parkinson, and Morbus Huntington; cognitive dysfunctions, preferably cognitive deficiency states, more preferably memory defects; epilepsy; respiratory tract diseases, preferably selected from the group consisting of asthma, bronchitis and pneumonia; coughing; urinary incontinence; an overactive bladder (OAB); disorders and/or injuries of the gastrointestinal tract; duodenal ulcers; gastric ulcers; colitis syndrome; apoplectic strokes; eye irritations; cutaneous irritations; neurotic skin conditions; allergic skin diseases; psoriasis; vitiligo; Herpes simplex; inflammations, preferably inflammation of the intestine, the eyes, the bladder, the skin, or the nasal mucosa; diarrhea; pruritus; osteoporosis; arthritis; osteoarthritis; rheumatic disorders; disorders of food intake, preferably selected from the group consisting of bulimia, cachexia, anorexia, and obesity; medicine addiction; medicine abuse; withdrawal phenomena following medicine addiction; tolerance development to pharmaceuticals, particularly to natural or synthetic opioids; drug addiction; drug abuse; withdrawal phenomena following drug addiction; alcohol addiction; alcohol abuse and withdrawal phenomena following alcohol addiction; for diuresis; for antinatriuresis; for affection of the cardiovascular system; for vigilance enhancement; for treatment of wounds and/or burning; for treatment of severed nerves; for libido enhancement; for modulation of movement activity; for anxiolysis; for local anesthesia and/or for inhibition of undesirable side effects, preferably selected from the group consisting of hyperthermia, hypertension, and bronchial constriction, as caused by administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil, and capsavanil.

The medicinal drug of the invention is more preferably suitable for treatment and/or prophylaxis of one or more disorders selected from the group consisting of pain, preferably pain selected from the group consisting of acute pain, chronic pain, neuropathic pain, and visceral pain; arthralgia; migraine; states of depression; neurodegenerative disorders, preferably selected from the group consisting of multiple sclerosis, Morbus Alzheimer, Morbus Parkinson, and Morbus Huntington; cognitive dysfunctions, preferably cognitive deficiency states, more preferably memory defects; inflammation, preferably inflammation of the intestine, the eyes, the bladder, the skin or the nasal mucosa; urinary incontinence; an overactive bladder (OAB); medicine addiction; medicine abuse; withdrawal phenomena following medicine addiction; tolerance development to pharmaceuticals, preferably tolerance development to natural or synthetic opioids; drug addiction; drug abuse; withdrawal phenomena following drug addiction; alcohol addiction; alcohol abuse and withdrawal phenomena following alcohol addiction.

The medicinal drug of the invention is most preferably suitable for treatment and/or prophylaxis of pain, preferably pain selected from the group consisting of acute pain, chronic pain, neuropathic pain, and visceral pain, and/or urinary incontinence.

The invention further relates to the use at least one compound of the invention and optionally one or more pharmaceutically compatible adjuvants for the production of a medicinal drug for vanilloid receptor 1-(VR1/TRPV1) regulation, preferably vanilloid receptor 1-(VR1/TRPV1) inhibition and/or to vanilloid receptor 1-(VR1/TRPV1) stimulation.

Preference is given to the use of at least one substituted compound of the invention and optionally one or more pharmaceutically compatible adjuvants for the production of a medicinal drug for prophylaxis and/or treatment of disorders or diseases which are at least partially mediated by vanilloid receptors 1.

Particular preference is given to the use of at least one compound of the invention and optionally one or more pharmaceutically compatible adjuvants for the production of a medicinal drug for treatment and/or prophylaxis of one or more disorders selected from the group consisting of pain, preferably of pain selected from the group consisting of acute pain, chronic pain, neuropathic pain, visceral pain, and arthralgia.

Particular preference is given to the use at least one compound of the invention and optionally one or more pharmaceutically compatible adjuvants for the production of a medicinal drug for treatment and/or prophylaxis of one or more disorders selected from the group consisting of hyperalgesia; allodynia; causalgia; migraine; states of depression; nervous disorders; neurotraumas; neurodegenerative disorders, preferably selected from the group consisting of multiple sclerosis, Morbus Alzheimer, Morbus Parkinson, and Morbus Huntington; cognitive dysfunctions, preferably cognitive deficiency states, more preferably memory defects; epilepsy; respiratory tract diseases, preferably selected from the group consisting of asthma, bronchitis, and pneumonia; coughing; urinary incontinence; an overactive bladder (OAB); disorders and/or injuries of the gastrointestinal tract; duodenal ulcers; gastric ulcers; colitis syndrome; apoplectic strokes; eye irritations; cutaneous irritations; neurotic skin conditions; allergic skin diseases; psoriasis; vitiligo; Herpes simplex; inflammation, preferably inflammation of the intestine, the eyes, the bladder, the skin, or the nasal mucosa; diarrhea; pruritus; osteoporosis; arthritis; osteoarthritis; rheumatic disorders; disorders of food intake, preferably selected from the group consisting of bulimia, cachexia, anorexia, and obesity; medicine addiction; medicine abuse; withdrawal phenomena following medicine addiction; tolerance development to pharmaceuticals, preferably to natural or synthetic opioids; drug addiction; drug abuse; withdrawal phenomena following drug addiction; alcohol addiction; alcohol abuse and withdrawal phenomena following alcohol addiction; for diuresis; for antinatriuresis; for affection of the cardiovascular system; for vigilance enhancement; for treatment of wounds and/or burning; for treatment of severed nerves; for libido enhancement; for modulation of movement activity; for anxiolysis; for local anesthesia and/or for inhibition of undesirable side effects, preferably selected from the group consisting of hyperthermia, hypertension, and bronchial constriction, as caused by administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil, and capsavanil.

Very high preference is given to the use of at least one substituted compound of the invention and optionally one or more pharmaceutically compatible adjuvants for the production of a medicinal drug for treatment and/or prophylaxis of one or more disorders selected from the group consisting of pain, preferably pain selected from the group consisting of acute pain, chronic pain, neuropathic pain, and visceral pain; arthralgia; migraine; states of depression; neurodegenerative disorders, preferably selected from the group consisting of multiple sclerosis, Morbus Alzheimer, Morbus Parkinson, and Morbus Huntington; cognitive dysfunctions, preferably cognitive deficiency states, more preferably memory defects; inflammation, preferably inflammation of the intestine, the eyes, the bladder, the skin, or the nasal mucosa; urinary incontinence; an overactive bladder (OAB); medicine addiction; medicine abuse; withdrawal phenomena following medicine addiction; tolerance development to pharmaceuticals, preferably tolerance development to natural or synthetic opioids; drug addiction; drug abuse; withdrawal phenomena following drug addiction; alcohol addiction; alcohol abuse and withdrawal phenomena following alcohol addiction.

Even more preference is given to the use of at least one substituted compound of the invention and optionally one or more pharmaceutically compatible adjuvants for the production of a medicinal drug for treatment and/or prophylaxis of pain, preferably selected from the group consisting of acute pain, chronic pain, neuropathic pain, and visceral pain, and/or urinary incontinence.

The medicinal drug of the invention is suitable for administration to adults and children including infants and babies.

The medicinal drug of the invention can exist as a liquid, semisolid, or solid pharmaceutical dosage form, for example, in the form of injection fluids, drops, juices, syrups, sprays, suspensions, tablets, patches, capsules, plasters, suppositories, ointments, creams, lotions, gels, emulsions, or aerosols, or in a multiparticular form, for example, in the form of pellets or granules, optionally compressed to tablets, filled into capsules, or suspended in a liquid, and can be administered as such.

In addition to at least one substituted compound of the above general formula I, optionally in the form of a pure stereoisomer thereof, particularly an enantiomer or diastereoisomer, the racemate thereof or in the form of mixtures of the stereoisomers, particularly the enantiomers or diastereoisomers, in an arbitrary mixing ratio, or optionally in the form of a corresponding salt or each in the form of a corresponding solvate, the medicinal drug of the invention usually contains further physiologically acceptable pharmaceutical adjuvants, which, for example, can be selected from the group consisting of carrier materials, fillers, solvents, diluents, surfactants, dyes, preservatives, blasting agents, slip agents, lubricants, flavors, and binding agents.

The selection of the physiologically acceptable adjuvants and the amount thereof to be used depends on whether the medicinal drug is to be applied orally, subcutaneously, parenterally, intravenously, intraperitoneally, intradermally, intramuscularly, intranasally, buccally, rectally or locally, e.g., to infected parts of the skin, the mucous membrane, or the eyes. Suitable preparations for oral administration are preferably in the form of tablets, dragees, capsules, granules, pellets, drops, juices and syrups, and preparations suitable for parenteral, topical and inhalative administration are solutions, suspensions, readily reconstitutable dry preparations, and sprays. The substituted compounds of the invention used in the medicinal drug of the invention in a depot in dissolved form or in a plaster, optionally with the addition of skin penetration enhancing agents, are suitable percutane administration forms. Formulations for oral or percutane application may be such as to effect delayed release of the respective substituted compound of the invention.

The production of the medicinal drug of the invention is effected by means of conventional agents, devices, methods, and processes known in the prior art, such as are described, for example, in "Remington's Pharmaceutical Sciences", Editor A. R. Gennaro, 17th Edition, Mack Publishing Company, Easton, Pa., 1985, particularly in Section 8, Chapters 76 to 93. The corresponding description is incorporated herein by reference and is to be regarded as part of the disclosure. The amount of the respective substituted compounds of the invention of the above general formula I to be administered to the patients can vary and is dependent, for example, on the weight or age of the patient and also on the method of administration, the indication, and the severity of the disorder. Usually from 0.001 to 100 mg/kg, preferably from 0.05 to 75 mg/kg and more preferably from 0.05 to 50 mg/kg of body weight of the patient of at least one such compound of the invention are administered.

Pharmacological Methods:

I. Functional Investigation on the Vanilloid Receptor 1 (VR1/TRPV1 Receptor)

The agonistic or antagonistic action of the substances to be investigated on the vanilloid receptor 1 (VR1/TRPV1) of the species rat can be determined using the following assay. According to this assay, the $Ca^{2+}$ influx through the receptor channel is quantified with the aid of a $Ca^{2+}$-sensitive dye (Type Fluo-4, Molecular Probes Europe BV, Leiden Netherlands) in a fluorescent imaging plate reader (FLIPR, Molecular Devices, Sunnyvale, USA).

Method:

Complete medium: 50 mL of HAMS F12 Nutrient Mixture (Gibco Invitrogen GmbH, Karlsruhe, Germany) with 10% by volume of FCS (fetal calf serum, Gibco Invitrogen GmbH, Karlsruhe, Germany, heat-inactivated);

2 mM of L-glutamine (Sigma, Munich, Germany);

1% by weight of AA solution (antibiotics/antimycotics solution, PAA, Pasching, Austria)

and 25 ng/mL of Medium NGF (2.5 S, Gibco Invitrogen GmbH, Karlsruhe, Germany)

Cell culture plate: Poly-D-lysine-coated, black 96-well plates with a clear bottom (96-well black/clear plate, BD Biosciences, Heidelberg, Germany) are additionally coated with laminin (Gibco Invitrogen GmbH, Karlsruhe, Germany) by diluting laminin to a concentration of 100 µg/mL with PBS (Ca—Mg-free PBS, Gibco Invitrogen GmbH, Karlsruhe, Germany). Aliquots having a concentration of 100 µg/mL of laminin are taken and stored at −20° C. The aliquots are diluted with PBS in the ratio 1:10 to 10 µg/mL of laminin and in each case 50 µL of the solution is pipetted into a well of the cell culture plate. The cell culture plates are incubated at 37° C. for at least two hours, the supernatant solution is aspirated and the wells are in each case washed twice with PBS. The coated cell culture plates are stored with supernatant PBS and this is removed only directly before the addition of the cells.

Preparation of the Cells:

The vertebral column is removed from decapitated rats and this is laid directly in a cold, i.e. ice bath-surrounded, HBSS buffer (Hank's buffered saline solution, Gibco Invitrogen GmbH, Karlsruhe, Germany) and 1% by volume of an AA solution (antibiotics/antimycotics solution, PAA, Pasching, Austria) is added. The vertebral column is cut in two longitudinally and the vertebral canal is removed together with fascias. Subsequently, the dorsal root ganglia (DRGs) are removed and in turn stored in cold HBSS buffer to which 1% by volume of an AA solution has been added. The DRGs completely freed from blood residues and spinal nerves are in each case transferred to 500 µL of cold collagenase Type 2 (PAA, Pasching, Austria) and incubated at 37° C. for 35 minutes. After addition of 2.5% by volume of trypsin (PAA, Pasching, Austria), the preparation is incubated at 37° C. for a further 10 minutes. On completion of incubation, the enzyme solution is carefully pipetted off and 500 µL of complete medium are added to the DRGs in each case. The DRGs are in each case repeatedly suspended, drawn through No. 1, No. 12 and No. 16 needles by means of a syringe and transferred to 50 mL Falcon tubes and these are filled to 15 mL with complete medium. The contents of each Falcon tube are in each case filtered through a 70 µm Falcon filter insert and centrifuged at 1200 rpm and room temperature for 10 minutes. The resulting pellet is in each case taken up in 250 µL of complete medium and the cell count is determined.

The number of cells in the suspension is adjusted to $3 \times 10^5$ per mL and in each case 150 µL of this suspension are added to a well of the cell culture plates coated as described above. The plates are allowed to stand at 37° C., 5% by volume of $CO_2$ and 95% relative humidity for two to three days in an incubator.

The cells are then loaded with 2 µM Fluo-4 and 0.01% by volume of Pluronic F127 (Molecular Probes Europe BV, Leiden Netherlands) in HBSS buffer (Hank's buffered saline solution, Gibco Invitrogen GmbH, Karlsruhe, Germany) at 37° C. for 30 min, washed 3 times with HBSS buffer and, after a further incubation of 15 minutes at room temperature, employed in the FLIPR assay for $Ca^{2+}$ measurement. The $Ca^{2+}$-dependent fluorescence is measured before and after addition of substances ($\lambda ex=488$ nm, $\lambda em=540$ nm). Quantification is carried out by measuring the highest fluorescence intensity (FC, fluorescence counts) over time.

FLIPR Assay:

The FLIPR protocol consists of 2 substance additions. Initially, the compounds to be tested (10 µM) are pipetted onto the cells and the $Ca^{2+}$ influx is compared with the control (capsaicin 10 µM). Information is gained therefrom in % activation relative to the $Ca^{2+}$ signal after addition of 10 µM of capsaicin (CP). After incubation for 5 minutes, 100 nM of capsaicin are applied and the influx of $Ca^{2+}$ is likewise determined.

Desensitizing agonists and antagonists lead to suppression of the $Ca^{2+}$ influx. The percentage inhibition is calculated in comparison with the maximum inhibition achieved with 10 µM of capsaicin.

Triplicate determinations (n=3) are carried out and these are repeated in at least 3 independent experiments (N=4).

Based on the percentage displacement effected by different concentrations of the compounds of the general formula I to be tested, $IC_{50}$ inhibition concentrations are calculated which cause 50 percent displacement of capsaicin. Conversion using the Cheng Prusoff equation gave $K_i$ values for the test substances (Cheng, Prusoff; Bioch. Pharmacol. 22, 3099-3108, 1973).

II. Functional Investigations on the Vanilloid Receptor (VR1)

The agonistic or antagonistic action of the substances to be examined on the vanilloid receptor (VR1) can alternatively be determined by the following assay. According to this assay the $Ca^{2+}$ influx through the canal is quantified with the aid of a $Ca^{2+}$-sensitive dye (type Fluo-4, Molecular Probes, Europe BV, Leiden, Netherlands) in a fluorescent imaging plate reader (FLIPR, Molecular Devices, Sunnyvale, USA).

Method:

Chinese hamster ovary cells (CHO-K1 cells, European Collection of Cell Cultures (ECACC) UK) are stably transfected with the VR1 gene. For carrying out functional investigations, these cells are plated on poly-D-lysine-coated, black 96-well plates with a clear bottom (BD Biosciences, Heidelberg, Germany) in a density of 25,000 cells/well. The cells are incubated overnight at 37° C. and 5% $CO_2$ in a culture medium (Nutrient Mixture 'am's F12, 10% by volume of FCS (fetal calf serum), 18 µg/ml of L-proline). On the following day the cells are incubated with Fluo-4 (Fluo-4 2 µM, Pluronic F127 0.01 by volume, Molecular Probes in HBSS (Hank's buffered saline solution), Gibco Invitrogen GmbH, Karlsruhe, Germany) for 30 minutes at 37° C. The plates are then washed 3 times with HBSS buffer and, after another incubation over a period of 15 minutes at room temperature, are used in the FLIPR for $Ca^{2+}$ measurement. The $Ca^{2+}$-dependent fluorescence is measured prior to and following the addition of the substances being examined (wavelength $\lambda_{ex}$=488 nm, $\lambda_{em}$=540 nm). Quantification is carried out by measuring the highest fluorescence intensity (PC, fluorescence counts) over time.

FLIPR Assay:

The FLIPR protocol consists of 2 substance additions. First of all, the substances to be tested (10 µM) are pipetted onto the cells and the $Ca^{2+}$ influx is compared with the control (capsaicin 10 µM) (percentage activation based on the $Ca^{2+}$ signal following addition of 10 µM of capsaicin). Following incubation over a period of 5 minutes 100 nM of capsaicin are applied and the influx of $Ca^{2+}$ is likewise determined.

Desensitizing agonists and antagonists led to a suppression of the $Ca^{2+}$ influx. The percentage inhibition compared with the maximum attainable inhibition using 10 µM of capsaicin is calculated.

Based on the percentage displacement effected by different concentrations of the compounds of the general formula I to be tested, $IC_{50}$ inhibition concentrations are calculated which cause 50 percent displacement of capsaicin. Conversion using the Cheng Prusoff equation gave $K_i$ values for the test substances (Cheng, Prusoff; Bioch. Pharmacol. 22, 3099-3108, 1973).

III. Formalin Test on Mice

The investigation for the determination of the antinociceptive action of the compounds of the invention is carried out in the formalin test on male mice (NMRI, of 20 to 30 g body weight, Iffa, Credo, Belgium).

In the formalin test, the first (early) phase (0 to 15 minutes after the formalin injection) and the second (late) phase (15 to 60 minutes after the formalin injection) are distinguished according to D. Dubuisson et al., Pain 1977, 4, 161-174. The early phase, as a direct reaction to the formalin injection, is a model of acute pain, whereas the late phase is regarded as a model of persistent (chronic) pain (T. J. Coderre et al., Pain 1993, 52, 259-285). The appropriate literature references are incorporated herein by reference and are to be regarded as part of the disclosure.

The compounds of the invention are examined in the second phase of the formalin test, in order to obtain information concerning a substance's action on chronic/inflammatory pain.

The point in time of administration of the compounds of the invention before the formalin injection is selected according to the method of administration of the compounds of the invention. Intravenous administration of 10 mg/kg body weight of the test substance is carried out 5 minutes before the formalin injection. This is carried out by a single subcutaneous formalin injection (20 µL, 1% strength aqueous solution) into the dorsal side of the right hind paw so that in the case of free-moving experimental animals a nociceptive reaction is induced which is manifested by marked licking and biting of the relevant paw.

The nociceptive behavior is then continuously registered during an investigation period of three minutes in the second (late) phase of the formalin test (21 to 24 minutes after the formalin injection) by observation of the animals. Quantification of the pain behavior is carried out by summating of the seconds during which the animals show licking and biting of the relevant paw during the investigation period.

In each case, comparison is carried out with control animals, which receive, instead of the compounds of the invention, a vehicle (0.9% strength aqueous sodium chloride solution) prior to formalin administration. Based on the quantification of the pain behavior, the substance's action in the formalin test is determined as the percentage change compared with the corresponding control.

Following injection of the substances having an antinociceptive action in the formalin test, the aforementioned behavioral patterns of the animals, i.e. licking and biting, decrease or cease.

IV. Test for Analgetic Effectiveness in the Writhing Test

Investigation of the compounds of the general formula I of the invention for analgetic effectiveness was carried out based on phenylquinone-induced writhing in mice, modified after I. C. Hendershot and J. Forsaith (1959) J. Pharmacol. Exp. Ther. 125, 237-240. The relevant literature reference is incorporated herein by reference and is to be regarded as part of the disclosure.

For this purpose, male NMRI mice having a weight of from 25 to 30 g were used. Groups of 10 animals per dose of the compound obtained received by intraperitoneal administration, 10 minutes after intravenous administration of the compounds under test, 0.3 mL/mouse of a 0.02% strength aqueous solution of phenylquinone (phenylbenzoquinone, marketed by Sigma, Deisenhofen, Germany and produced by adding to the solution 5% by weight of ethanol and storing it in a water bath at 45° C.). The animals were placed individually in observation cages. With the aid of a pushbutton counter, the number of pain-induced stretching movements (so-called writhing reactions—straightening of the body with stretching of the rear extremities) was counted over a period of from 5 to 20 minutes following the administration of phenylquinone. The control was provided by animals receiving only physiological saline. All of the compounds were tested using the standard dosage of 10 mg/kg.

V. Hypothermia Assay in Mice

Description of the Method:

The hypothermia assay was carried out in male NMRI mice (weight 25-35 gram, Zuechter IFFA CREDO, Brussels, Belgium). The animals were kept under standardized conditions: light/dark rhythm (from 6:00 to 18:00 hours light phase and from 18:00 to 6:00 hours dark phase), room temperature 19-22° C., relative air humidity 35-70%, 15 air changes per hour, air movement <0.2 m/sec. The animals received standard feed (ssniff R/M-Haltung, ssniff Spezialdiaeten GmbH, Soest, Germany) and tap water. Water and feed were withdrawn during the experiment. All animals were used only once during the experiment. The animals had an acclimatization period of at least 5 days.

Acute administration of capsaicin (VR-1 agonist) leads to a drop in the core temperature of the body in rats and mice due to stimulation of heat sensors. Only specifically effective VR-1 receptor antagonists can antagonize the capsaicin-induced hypothermia. By contrast, hypothermia induced by morphine is not antagonized by VR-1 antagonists. This model is therefore suitable for identifying substances with VR-1 antagonistic properties via their effect on body temperature.

Measurement of the core temperature is carried out using a digital thermometer (Thermalert TH-5, physitemp, Clifton N.J., USA). The sensing element is inserted into the rectum of the animals.

To give an individual basic value for each animal, the body temperature is measured twice at an interval of approximately half an hour. One group of animals (n=from 6 to 10) then receives an intraperitoneal (i.p.) application of capsaicin 3 mg/kg and vehicle (control group). Another group of animals receives the substance to be tested (i.v. or p.o.) and additionally capsaicin (3 mg/kg) i.p. The administration of the test substance is carried out i.v. 10 min, or p.o 15 minutes, prior to capsaicin. The body temperature is then measured 7.5/15 and 30 min following capsaicin (i.v.+i.p.) or 15/30/60/90/120 min (p.o.+i.p.) following capsaicin. In addition, one group of animals is treated with the test substance only and one group with vehicle only. The evaluation or representation of the measured values as mean+/−SEM of the absolute values is presented as a graphical representation. The antagonistic action is calculated as the percentage reduction of the capsaicin-induced hypothermia.

VI. Neuropathic Pain in Mice

The investigation on effectiveness on neuropathic pain was examined using the Bennett Model (chronic constriction injury; Bennett and Xie, 1988, Pain 33:87-107).

Three loose ligatures are tied around the right ischiadic nerve of Ketavet/Rompun-anesthetized NMRI mice weighing 16-18 g. The animals develop hypersensitivity of the nervate paw caused by the damaged nerve, which hypersensitivity is quantified, following a recovery phase of one week, over a period of approximately three weeks by means of a cold metal plate (temperature 4° C.) (cold allodynia). The animals are observed on this plate over a period of 2 min, and the withdrawal reactions of the damaged paw are counted. Based on the pre-value prior to administration of substance, the substance's action over a certain period of time is determined at various points in time (e.g., 15, 30, 45, or 60 min following administration) and the resultant area under the curve (AUC) and/or the inhibition of cold allodynia at the individual measuring points was/were expressed as percentage effect relative to the vehicle control (AUC) or to the starting value (individual measuring points). The group size is n=10, the significance of an anti-allodynic action (=p<0.05) is determined with the aid of an analysis of variance with repeated measures and Bonferroni post hoc analysis.

The invention is described below with reference to some examples. These explanations are by way of example only and do not restrict the general inventive concept.

EXAMPLES

The yields of the compounds produced were not optimized.
All temperatures are uncorrected.
The statement "equivalents" denotes mol equivalents, "RT" room temperature, "M" and "N" are concentrations in mol/L, "aq." aqueous, "sat." saturated, "soln. solution, and other abbreviations are:
DMF N,N-dimethylformamide
EDCl N-ethyl-N'-(3-dimethylaminopropyl)carbodiimide hydrochloride
EA ethyl acetate
$H_2O$ water
MeOH methanol The chemicals and solvents used were obtained commercially from the usual suppliers (Acros, Avocado, Aldrich, Bachem, Fluka, Lancaster, Maybridge, Merck, Sigma, TCI, Oakwood etc.) or synthesized by usual methods known to the person skilled in the art.

The stationary phase used for column chromatography was silica gel 60 (0.0-0-0.063 mm) supplied by E. Merck, Darmstadt.

The thin-layer chromatographic analyses were carried out using preformed HPTLC plates, Silica Gel 60 F 254, supplied by E. Merck, Darmstadt.

The mixing ratios of solvents, mobile solvents, or for chromatographic analyses are always stated in vol/vol.

Chemical analysis was carried out by mass spectroscopy and NMR.

1. General Instructions for the Preparation of Amines of the General Formula V-A Preparation of amines of the general formula V-A is Carried Out as Illustrated by the following scheme 1.

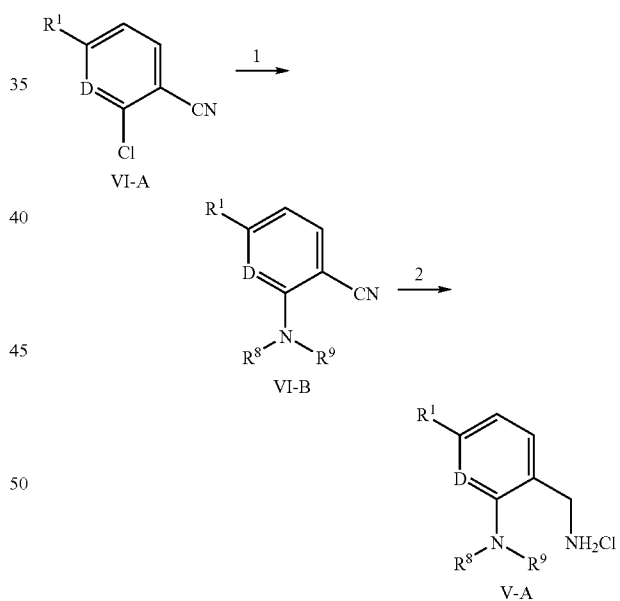

Stage 1: Preparation of Nitrites of the General Formula VI-B
Method A:

Compounds of the general formula VI-A (1 equivalent), in which $R^1$ and D have the meanings stated above and m stands for 0, 1, 2, or 3, are stirred with an amine of the general formula $HNR^8R^9$ (6 equivalents) over a period of 48 hours at RT. To the reaction mixture there is added 1N hydrochloric acid and the mixture is extracted with EA a number of times. The aqueous phase is saturated with NaCl and then again extracted with EA. The combined organic phases are washed with 1N hydrochloric acid and with sat. aq. NaCl solution, dried over $MgSO_4$, and the solvent is removed in vacuo.

Method B:

Compounds of the general formula VI-A (1 equivalent), in which $R^1$ and D have the meanings stated above and m stands for 0, 1, 2, or 3, are stirred with an amine of the general formula $HNR^8R^9$ (2 equivalents) and DBU [1.8-diaza-bicyclo[5.4.0]undec-7-ene] (2 equivalents) in acetonitrile (7 mL per mmol of the compound of formula VI-A) over a period of 12 hours at RT. The reaction mixture is extracted with EA a number of times. The combined organic phases are washed with sat. aq. NaCl solution, dried over $MgSO_4$, and the solvent is removed in vacuo. The residue is purified in each case by column chromatography ($SiO_2$, various mixtures of hexane/EA).

The following compound was produced by method B.

6-(Trifluoromethyl)-2-(4-methylpiperidin-1-yl)pyridine-3-carbonitrile

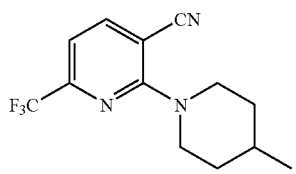 [SMILES: CC1CCN(c2nc(C(F)(F)F)ccc2C#N)CC1]

$^1$H NMR (300 MHz, $CDCl_3$) δ 7.87 (d, 1 h, J=7.8 Hz), 6.95 (d, 1 h, J=7.8 Hz), 4.53 (m, 2H), 3.05 (m, 2H), 1.78 (m, 2H), 1.64 (m, 1H), 1.29 (m, 2H), 1.00 (d, 3H, J=6.6 Hz); IR (PUR) 2926, 2852, 2218, 1590, 1497, 1456, 1324, 1237, 1186, 1147, 1082, of 963 $cm^{-1}$; MS (FAB) m/z 270 (M+H)

Step 2

Method 1

Compounds of the general formula VI-B (5 mmol), in which $R^1$, $R^8$, $R^9$, and D have the meanings stated above and m stands for 0, 1, 2, or 3, palladium-on-charcoal (10%, 500 mg) and conc. hydrochloric acid (3 mL) are dissolved in MeOH (30 mL) and exposed to a hydrogen atmosphere over a period of 6 hours at RT. The reaction mixture is filtered over Celite and the filtrate is concentrated in vacuo. The residue is purified by means of flash chromatography ($SiO_2$, EA).

Method 2:

Compounds of the general formula VI-B (2 mmol), in which $R^1$, $R^8$, $R^9$, and D have the meanings stated above and m stands for 0, 1, 2, or 3, are dissolved in THF (10 mL, 10 mL), and $BH_3 \cdot S(CH_3)_2$ [2.0 M in THF, 3 mL, 3 equivalents] is added. The reaction mixture is heated under reflux over a period of 8 hours, aq. HCl (2N) is added and the reaction mixture is again heated under reflux for 30 minutes. Aq. sodium hydroxide solution (2N) is added to the reaction mixture and the mixture is washed with EA. The combined organic phases are washed with sat. aq. NaCl solution and dried over magnesium sulfate. The solvent is removed in vacuo and the residue is purified by column chromatography ($SiO_2$, various mixtures of dichloromethane and methanol as mobile solvent).

The following compound was obtained by method 2.

(6-(Trifluoromethyl)-2-(4-methylpiperidin-1-yl)pyridin-3-yl)methanamine

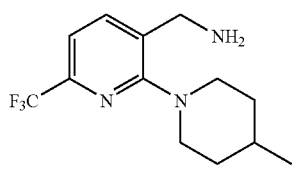 [SMILES: CC1CCN(c2nc(C(F)(F)F)ccc2CN)CC1]

$^1$H NMR (300 MHz, $CDCl_3$) δ 7.89 (d, 1H, J=7.8 Hz), 7.33 (d, 1H, J=7.8 Hz), 3.88 (s, 2H), 3.39 (m, 2H), 2.83 (m, 2H), 1.75 (m, 2H), 1.55 (m, 1H), 1.38 (m, 2H), 1.00 (d, 3H, J=6.6 Hz); MS (FAB) m/z 274 (M+H)

2. General Instructions for the Preparation of Amines of the General Formula V-E The preparation of amines of the general formula V-E is carried out as illustrated in the following scheme 2.

Scheme 2.

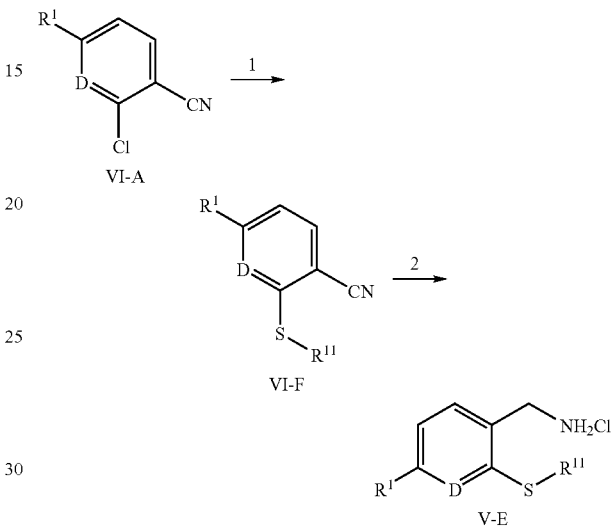

Step 1

Synthesis of 2-(cyclohexylthio)-6-(trifluoromethyl) nicotinonitrile

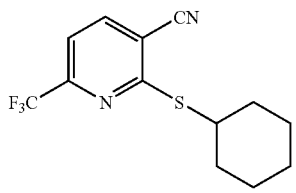 [SMILES: N#Cc1ccc(C(F)(F)F)nc1SC1CCCCC1]

1,3 Equivalents of NaH (4.9 g, 0.124 mol) were dissolved in 50 mL of DMF under a blanket of nitrogen. Following the addition of 1.2 equivalents of cyclohexanethiol (14.2 mL, 0.116 mol), the mixture was stirred at room temperature over a period of 1.5 h. The resulting suspension was cooled to 10° C. and added dropwise to 1 equivalent of 2-chloro-6-(trifluoromethyl)nicotinonitrile (20 g, 0.096 mol) in 50 mL of DMF and stirred over a period of 2 h at room temperature. The reaction mixture was diluted with sat. aq. $NH_4Cl$ solution and with 1 L of water and extracted with EA (3×200 mL). The combined organic phases were washed with sat. aq. NaCl solution, dried over $MgSO_4$ and concentrated in vacuo. Column chromatographic purification (silica gel 100-200 mesh, eluent: 2% EA in hexane) produced 26 g (93.8%) of product.

$^1$H NMR (300 MHz, $CDCl_3$) δ 7.94 (d, 1H, J=7.9 Hz), 7.34 (d, 1H, J=7.9 Hz), 4.00 (m, 1H), 1.90-2.14 (m, 2H), 1.42-1.88 (m, 8H)

IR (neat) 2930, 2854, 2232, 1643, 1573, 1447, 1334, 1245, 1186, 1149, 1107, 851 $cm^{-1}$ MS (FAB) m/z 287 (M+H)

Step 2

Synthesis of (2-(cyclohexylthio)-6-(trifluoromethyl)-pyridin-3-yl)methanamine dihydrochloride The nitrile (26 g, 0.091 mol) was dissolved in 600 mL of THF under a blanket of nitrogen and cooled to 5° C. BH$_3$-DMS (13.78 g, 0.182 mol) was added dropwise and the mixture was boiled under reflux over a period of 20 h. After cooling to 5° C., 100 mL of MeOH was added to the reaction batch and the mixture was stirred at room temperature over a period of 15 minutes. Di-tert-butyldicarbonate (29.7 g, 0.136 mol) was then added and the mixture was stirred at room temperature for 30 min. Following the removal of the solvent in vacuo, the crude product was purified by column chromatography (silica gel 100-200 mesh, eluent: 10% EA in hexane) and 23.4 g (66%) of product were obtained. The crude product was dissolved in 120 mL of sat. HCl/dioxane soln. and the solution was stirred at room temperature over a period of 6 h. Following the removal of the solvent in vacuo, the solid matter was washed with 10% of EA in hexane (2×100 mL) and isolated by filtration.

Yield: 17 g (88.8%)

$^1$H NMR (DMSO-d$_6$, 400 MHz): δ 8.8 (s, 2H), 8.05 (d, 1H), 7.76 (d, 1H), 4.01 (s, 1H), 3.86-3.93 (m, 1H), 2.02-2.08 (m, 2H), 1.71-1.74 (m, 2H), 1.40-1.60 (m, 6H).

3. General Instructions for the Preparation of Amines of the General Formula V-B The preparation of amines of the general formula V-B is carried out as illustrated in the following scheme 3.

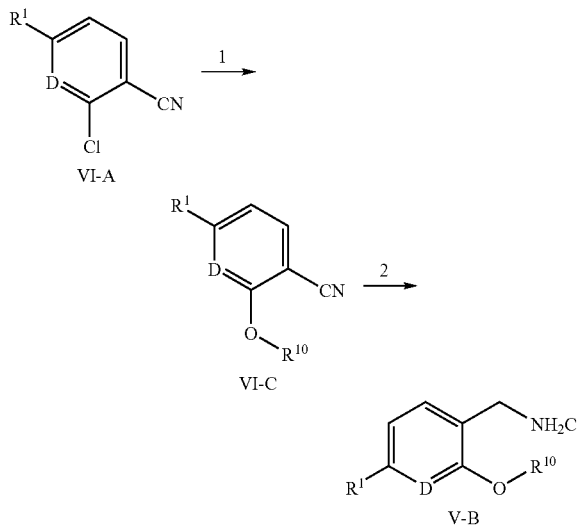

Scheme 3.

Step 1: Preparation of Nitrites of the General Formula VI-C

Compounds of the general formula VI-A (1 equivalent), in which R$^1$ and D have the meanings stated above and m stands for 0, 1, 2, or 3, are stirred with an alcohol of the general formula HO—R$^{10}$ (3.5 equivalents) and DBU [1.8-diaza-bicyclo[5.4.0]undec-7-ene] (3,5 equivalents) in acetonitrile (7 mL per mmol of the compound of formula VI-A) over a period of 12 hours at RT. The reaction mixture is extracted with EA a number of times. The combined organic phases are washed with sat. aq. NaCl soln. dried over MgSO$_4$, and the solvent is removed in vacuo. The residue is purified in each case by column chromatography (SiO$_2$, various mixtures of hexane/EA).

Method 2:

Compounds of the general formula VI-C (2 mmol), in which R$^1$, R$^{10}$, and D have the meanings stated above and m stands for 0, 1, 2, or 3, are dissolved in THF (10 mL, 10 mL) and BH$_3$.S(CH$_3$)$_2$ [2.0 M in THF, 3 mL, 3 equivalent] is added. The reaction mixture is heated under reflux over a period of 8 hours, aq. HCl (2N) is added and the reaction mixture is again heated under reflux for 30 minutes. Aq. sodium hydroxide solution (2N) is added to the reaction mixture and the mixture is washed with EA. The combined organic phases are washed with sat. aq. NaCl solution and dried over magnesium sulfate. The solvent is removed in vacuo and the residue is purified by column chromatography (SiO$_2$, various mixtures of dichloromethane and methanol as mobile solvent).

Method 3:

Compounds of the general formula VI-C (1.5 mmol), in which R$^1$, R$^{10}$, and D have the meanings stated above and m stands for 0, 1, 2, or 3, are dissolved in diethyl ether (3 mL) and a suspension of lithium aluminum hydride (3 mmol) in ether (5 mL) is slowly added dropwise at 0° C. The reaction mixture is heated under reflux over a period of 4 hours and methanol and then 1N aq. NaOH solution are slowly added dropwise at 0° C. The reaction mixture is diluted with methanol and filtered over Celite. The solvent is removed in vacuo and the residue is purified by column chromatography (SiO$_2$, various mixtures of dichloromethane and methanol as mobile solvent).

4. General Instructions for the Preparation of Amines of the General Formula V-C The preparation of amines of the general formula V-C is carried out as illustrated in the following scheme 4.

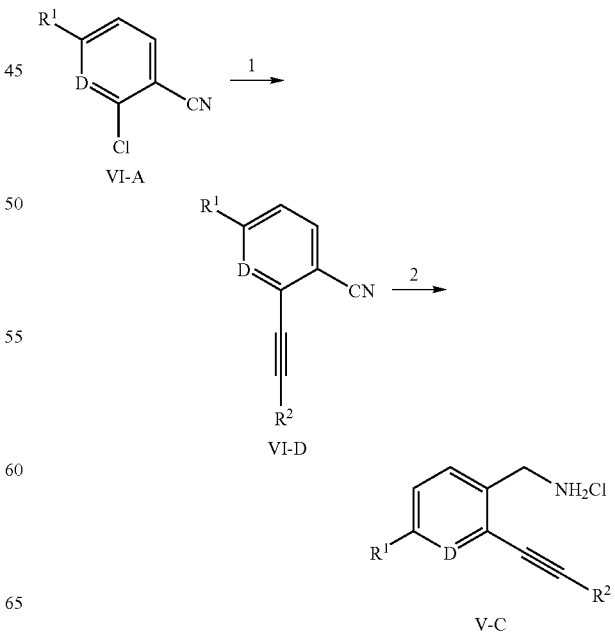

Scheme 4.

Step 1

Preparation of Nitrites of the General Formula VI-D

Compounds of the general formula VI-A (1 equivalent), in which $R^1$ and D have the meanings stated above and m stands for 0, 1, 2, or 3, are dissolved together with bis(triphenylphosphine)palladium dichloride (7 mol %) and copper(I) iodide (14 mol %) in 1-methyl-2-pyrrolidinone (7 mL per mmol of the compound of the general formula VI-A). Following a period of 10 minutes the alkyne of the general formula HC≡C—$R^2$ (3,5 equivalents) and N,N-diisopropylethylamine (2 equivalents) are added and the reaction mixture is stirred over a period of 12 h at a temperature between 90 and 110° C. The reaction mixture is filtered over Celite and extracted with EA a number of times. The combined organic phases are washed with sat. aq. NaCl solution, dried over $MgSO_4$, and the solvent is removed in vacuo. The residue is purified in each case by column chromatography ($SiO_2$, various mixtures of hexane/EA).

5. General Instructions for the Preparation of Amines of the General Formula V-D The preparation of amines of the general formula V-D is carried out as illustrated in the following scheme 5.

Scheme 5.

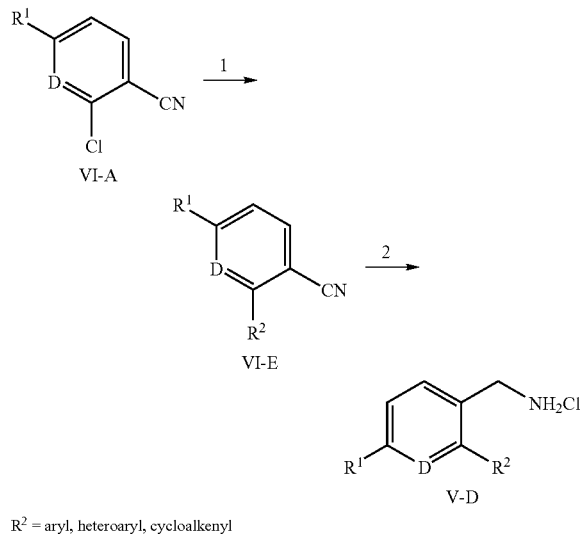

$R^2$ = aryl, heteroaryl, cycloalkenyl

Step 1: Preparation of Nitrites of the General Formula VI-E

Compounds of the general formula VI-A (1 equivalent), in which $R^1$ has the aforementioned meaning and m stands for 0, 1, 2, or 3, are stirred with palladium dichloride (5 mol %) and a compound of the general formula $R^2$—$B(OH)_2$ (2 equivalents), in which $R^2$ stands for aryl, heteroaryl, or cycloalkenyl, in a solvent mixture of toluene/dioxane/2N aq. sodium carbonate solution (20 mL per 1 mmol of compounds of the general formula VI-A). The reaction mixture is heated under reflux over a period of 12 h and filtered over Celite. The combined organic phases are dried over magnesium sulfate and the solvent is removed in vacuo. The residue is purified by column chromatography ($SiO_2$, various solvent mixtures of hexane and EA).

Step 2

Method 1:

Compounds of the general formula VI-E (5 mmol), in which $R^1$ and $R^2$ have the meanings stated above and m stands for 0, 1, 2, or 3, palladium-on-charcoal (10%, 500 mg) and conc. hydrochloric acid (3 mL) are dissolved in MeOH (30 mL) and exposed to a hydrogen atmosphere over a period of 6 hours at RT. The reaction mixture is filtered over Celite and the filtrate is concentrated in vacuo. The residue is purified by means of flash chromatography ($SiO_2$, EA).

Method 2:

Compounds of the general formula VI-E (2 mmol), in which $R^1$ and $R^2$ have the meanings stated above and m stands for 0, 1, 2, or 3, are dissolved in THF (10 mL, 10 mL) and $BH_3 \cdot S(CH_3)_2$ [2.0 M in THF, 3 mL, 3 equivalent] is added. The reaction mixture is heated under reflux over a period of 8 hours, aq. HCl (2N) is added and the reaction mixture is again heated under reflux for 30 minutes. Aq. sodium hydroxide solution (2N) is added to the reaction mixture and the mixture is washed with EA. The combined organic phases are washed with sat. aq. NaCl solution and dried over magnesium sulfate. The solvent is removed in vacuo and the residue is purified by column chromatography ($SiO_2$, various mixtures of dichloromethane and methanol as mobile solvent).

6. General Instructions for the Preparation of Carboxylic Acids of the General Formula VII 6a. General Instructions for the Synthesis of 2-(3-fluoro-4-(methylsulfonamido)-phenyl)-2-methylalkyl acids

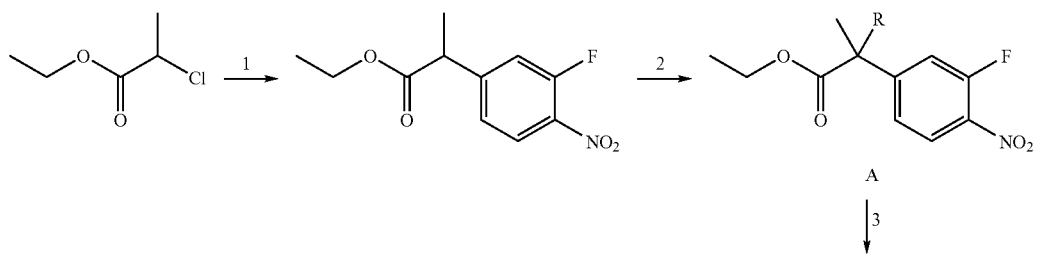

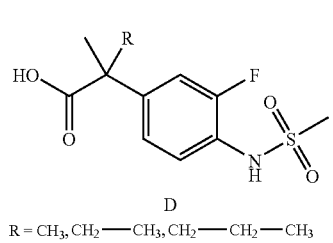 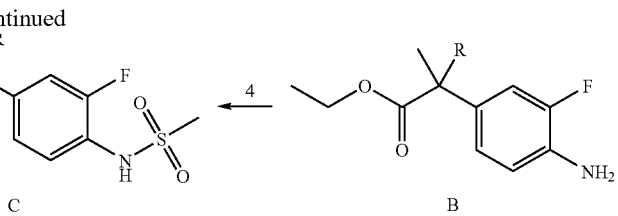

R = CH₃, CH₂—CH₃, CH₂—CH₂—CH₃

Step 1

3 Equivalents of potassium tert-butyloxide are suspended in DMF under a blanket of nitrogen and cooled to −40° C. While maintaining this temperature, a mixture of o-fluoronitrobenzene (1 equivalent) and ethyl 2-chloropropionate (1,2 equivalent) is then added and the mixture is stirred over a period of 10 minutes. The reaction mixture is diluted with acetic acid and water at −40° C. The aqueous phase is then extracted a number of times with 20% strength EA in hexane, and the combined organic phases are washed with water and sat. aq. NaCl solution and dried over MgSO₄. Purification of the concentrated organic phase is effected by column chromatography (silica gel 100-200 mesh, eluent: 10% EA in hexane).

Step 2

To a solution of the resulting nitroester (1 equivalent) and NaH (0.6 equivalents) in DMF there are slowly added dropwise 0.75 equivalents of alkyliodide at 0° C., and the reaction mixture is stirred over a period of approximately 10 minutes. The reaction mixture is then diluted with 1N HCl solution and water and extracted with diethyl ether a number of times. The combined organic phases are washed with water and sat. aq. NaCl solution, dried over MgSO₄, and concentrated in vacuo. Further purification of the crude product may be carried out by column chromatography (silica gel: 100-200 mesh, eluent: 10-20% EA in hexane).

Step 3

A suspension of the compound of the general formula A (1 equivalent) and palladium-on-charcoal (10% of Pd) in EtOH is hydrogenated over a period of 1 h under a blanket of hydrogen. The suspension is isolated by filtration, concentrated in vacuo, and purified by column chromatography (eluent: EA/hexane).

Step 4

The compound of the general formula B (1 equivalent) is used in dichloromethane and pyridine as initial batch and cooled to 0° C. Methanesulfonyl chloride (1.5 equivalents) is added dropwise at 0 GRADC and the reaction mixture is stirred over a period of 2 h at room temperature. After recooling the mixture to 0° C., it is acidified with 4N aq. HCl to pH 3. The organic phase is extracted with dichloromethane a number of times. The combined organic phases are washed with water and sat. aq. NaCl solution, dried over MgSO₄ and concentrated to dryness. Purification by column chromatography (eluent: EA in hexane) gives the desired product.

Step 5

1 Equivalent of the ethyl ester of the general formula C is dissolved in a 2:1 mixture of THF/water and stirred over a period of 15 minutes. To this solution there are added 3 equivalents of LiOH likewise dissolved in a 2:1 mixture of THF/water and the suspension is stirred at 45° C. over a period of 2 h. The aqueous phase is set to pH 1 with 4N aq. HCl with cooling and extracted with dichloromethane a number of times. The combined organic phases are dried over MgSO₄ and concentrated under reduced pressure.

6b. General Instructions for the Synthesis of 1-(3-fluoro-4-(methylsulfonamido)-phenyl)cycloalkylcarboxylic acids

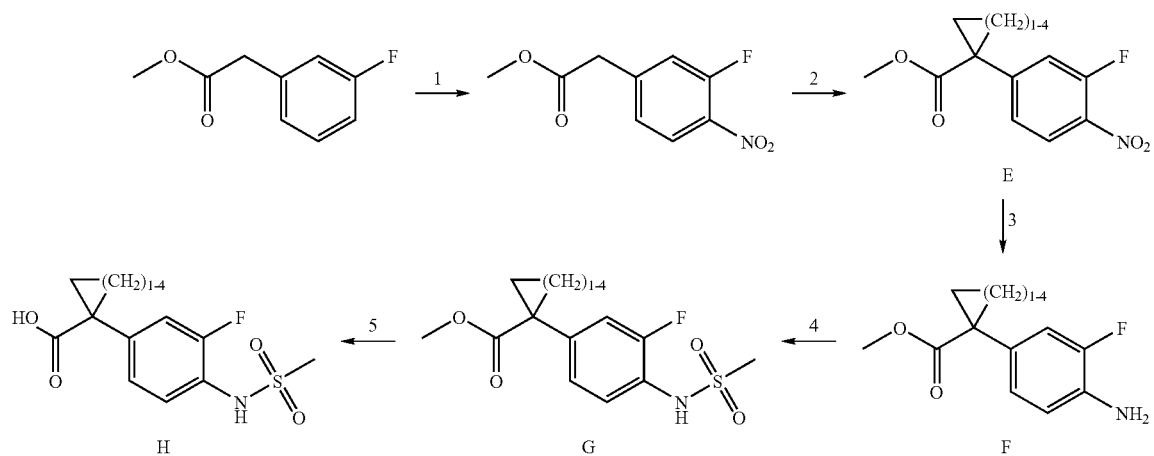

Step 1

A mixture of 3-fluorophenyl acetate (1 equivalent) and sulfuric acid (0.261 equivalents) is added dropwise to a solution of nitric acid (1 equivalent) at 0° C. and the reaction mixture is stirred over a period of 2 h. The reaction mixture is diluted with ice water and extracted with EA a number of times. The combined organic phases are washed with water, concentrated in vacuo and purified by column chromatography (eluent: EA/hexane).

Step 2

NaH (10 equivalents) is slowly added to nitrophenyl acetate (1 equivalent) dissolved in dry THF, the reaction mixture is stirred over a period of 10 minutes and the corresponding dibromoalkyl compound (5 equivalents) is then added. The reaction mixture is heated to room temperature within a period of 30 minutes and diluted with sat. aq. NH$_4$Cl solution. Following aqueous workup, the resulting crude product is purified by flash chromatography (eluent: EA/hexane).

Step 3

A suspension of the compound of the general formula E (1 equivalent) and palladium-on-charcoal (10% of Pd) in EtOH is hydrogenated under a blanket of hydrogen over a period of 1 h. The suspension is isolated by filtration, concentrated in vacuo, and purified by column chromatography (eluent: EA/hexane).

Step 4

The amine compound of the general formula F (1 equivalent) is used in dichloromethane as initial batch, cooled to 0° C., and methanesulfonyl chloride (1.5 equivalents) is added dropwise at 0° C. and the reaction mixture is stirred at room temperature over a period of 2 h. After re-cooling the mixture to 0° C., it is acidified with 4N aq. HCl to pH 3. The organic phase is extracted with dichloromethane a number of times. The combined organic phases are washed with water and sat. aq. NaCl solution, dried over MgSO$_4$ and concentrated to dryness. Purification by column chromatography (eluent: EA in hexane) gives the desired product.

Step 5

1 Equivalent of the ethyl ester is dissolved in a 2:1 mixture of THF/water and the solution is stirred over a period of 15 minutes. To this solution there are added 3 equivalents of LiOH likewise dissolved in a 2:1 mixture of THF/water, and the mixture is stirred over a period of 2 h at 45 C. The aqueous phase is set to pH 1 with aq. 4N HCl with cooling and extracted with dichloromethane a number of times. The combined organic phases are dried over MgSO$_4$ and concentrated under reduced pressure.

6c. General Instructions for the Synthesis of 2-cycloalkyl-2-(3-fluoro-4-(methyl-sulfonamido)phenyl)acetic acids

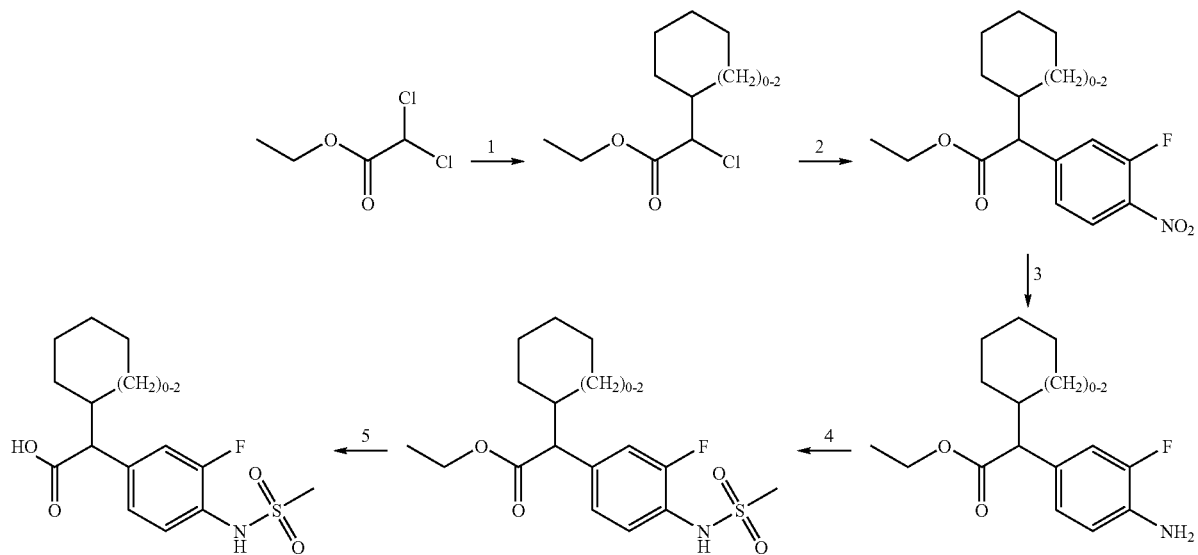

6c 1. Synthesis of 2-cyclohexyl-2-(3-fluoro-4-(methylsulfonamido)phenyl)acetic acid

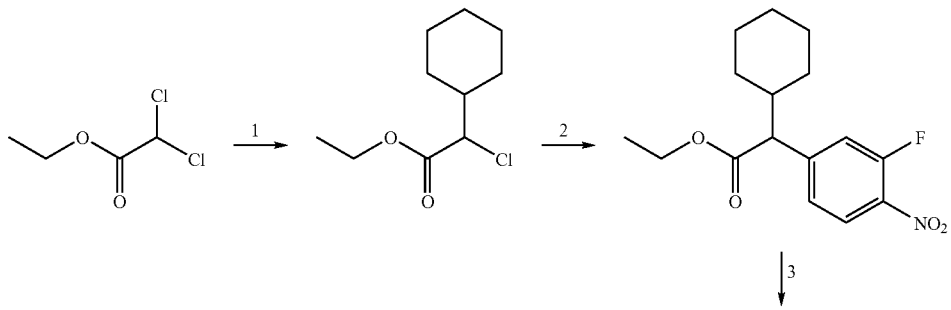

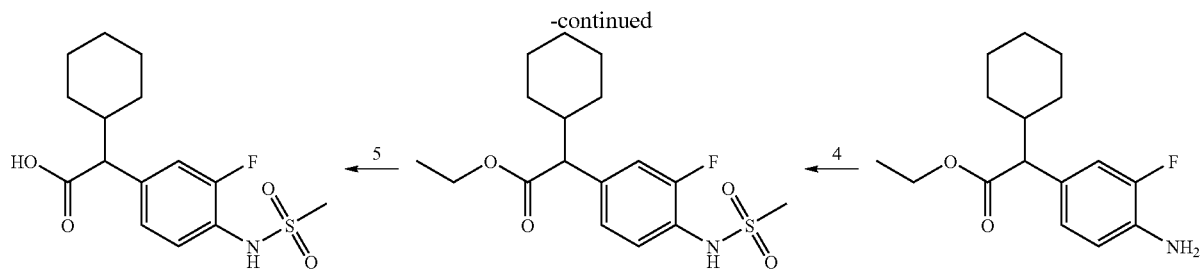

Step 1: Synthesis of ethyl 2-chloro-2-cyclohexylacetate 100 mL of 1M $BH_3$-THF complex (100 mmol) were added to 170 mL of dry THF under a blanket of nitrogen at room temperature. 12.3 mL of cis-1,5-cyclooctadiene (100 mmol) were added dropwise to this mixture within a period of 5 minutes, and the temperature rose to 45° C. The reaction mixture was heated under reflux over a period of 1.5 h, again cooled to 45° C., and 10.1 mL of cyclohexene (100 mmol) were added and stirring was continued for a further 2 h at 45° C. After the reaction mixture had been cooled in an ice bath, 12.2 mL of ethyldichloroacetate (100 mmol) in 50 mL of tert-butanol were added, stirring was continued for a further 15 minutes and 1M potassium tert-butylate (100 mmol, 100 mL) was added dropwise within a further 15 minutes. The reaction mixture was then stirred over a period of 15 minutes, 33 mL of 3M sodium acetate solution (100 mmol) were added and 22.5 mL of 30% strength aq. $H_2O_2$ solution (750 mmol) were added dropwise. The mixture was stirred at room temperature over a period of 30 minutes, then salted out with NaCl, the organic phase dried over $MgSO_4$ and the solvent removed under reduced pressure. Following washing of the residual solid matter with tert-butylmethyl ether, cyclohexane/tert-butylmethyl ether (9:1), tert-butylmethyl ether, and EA, there were obtained 7.6 g (37.4%) of product.

Step 2: Synthesis of ethyl 2-cyclohexyl-2-(3-fluoro-4-nitrophenyl)acetate 8.2 g of potassium tert-butylate were dissolved in 70 mL of DMF and cooled to −45° C. To this, a mixture of ethyl 2-chloro-2-cyclohexylacetate (36.6 mmol, 7.5 g) and 1-fluoro-2-nitrobenzene (36.6 mmol, 3.9 mL) was gently added dropwise and stirring was continued for a further 20 minutes. The reaction mixture was set to pH 4 with 16% strength aq. HCl, diluted with 25 mL of water, and extracted with EA (3×50 mL). After combining the organic phases, they were washed with water and sat. aq. NaCl solution, dried over $MgSO_4$, and concentrated in vacuo. The resulting residue was purified by column chromatography (silica gel: mesh 100-200, eluent: 10% EA in cyclohexane) and yielded 5.5 g (49%) of the desired product.

Step 3: Synthesis of ethyl 2-(4-amino-3-fluorophenyl)-2-cyclohexylacetate

Ethyl 2-cyclohexyl-2-(3-fluoro-4-nitrophenyl)acetate was dissolved in a 1:1 mixture of EtOH and EA (420 mL) and hydrogenation was carried out in an H-cube (1 bar, 25° C., 1 mL/min and 0.25 mol/L). Following removal of the solvent and drying, 5 g of the desired product were obtained (quantitative conversion).

Step 4: Synthesis of ethyl 2-cyclohexyl-2-(3-fluoro-4-(methylsulfonamido)-phenyl)acetate The amino compound ethyl 2-(4-amino-3-fluorophenyl)-2-cyclohexylacetate (5 g, 179 mmol) was dissolved in 15 mL of pyridine, cooled under a blanket of nitrogen to 0° C., and 2 mL of methanesulfonyl chloride (26.8 mmol) were added, and stirring of the reaction mixture was continued at 0° C. over a period of 1 h. To the reaction mixture there were added, with ice cooling, 15 mL of water, and the mixture was set to pH 1 with 16% strength HCl. Following extraction of the mixture with dichloromethane (3×50 mL), the organic phases were combined, dried over $MgSO_4$ and concentrated in vacuo. Purification of the crude product was carried out by column chromatography (silica gel: 100-200 mesh, eluent: 50% EA in cyclohexane) and yielded 5.4 g (85.4%) of product.

Step 5: Synthesis of 2-cyclohexyl-2-(3-fluoro-4-(methylsulfonamido)phenyl)-acetic acid The phenylacetate (15.2 mmol, 5.4 g) was dissolved in a mixture of 30 mL of THF and 15 mL of water, 1.09 g of LiOH (45.7 mmol) were added and the mixture was heated under reflux over a period of 6 h and stirring was continued over a period of 12 h at room temperature. To the reaction mixture there were added 15 mL of water and the phases were separated. The aqueous phase was acidified with HCl and extracted with dichloromethane (3×50 mL) a number of times. The combined organic phases were dried over $MgSO_4$, concentrated, and the residue purified by means of column chromatography (silica gel: 100-200 mesh, eluent: 50% EA in cyclohexane). Yield 1.05 g (21%).

6d. Synthesis of 2-(3-fluoro-4-(methylsulfonamido)phenyl)-2-phenylacetic acid

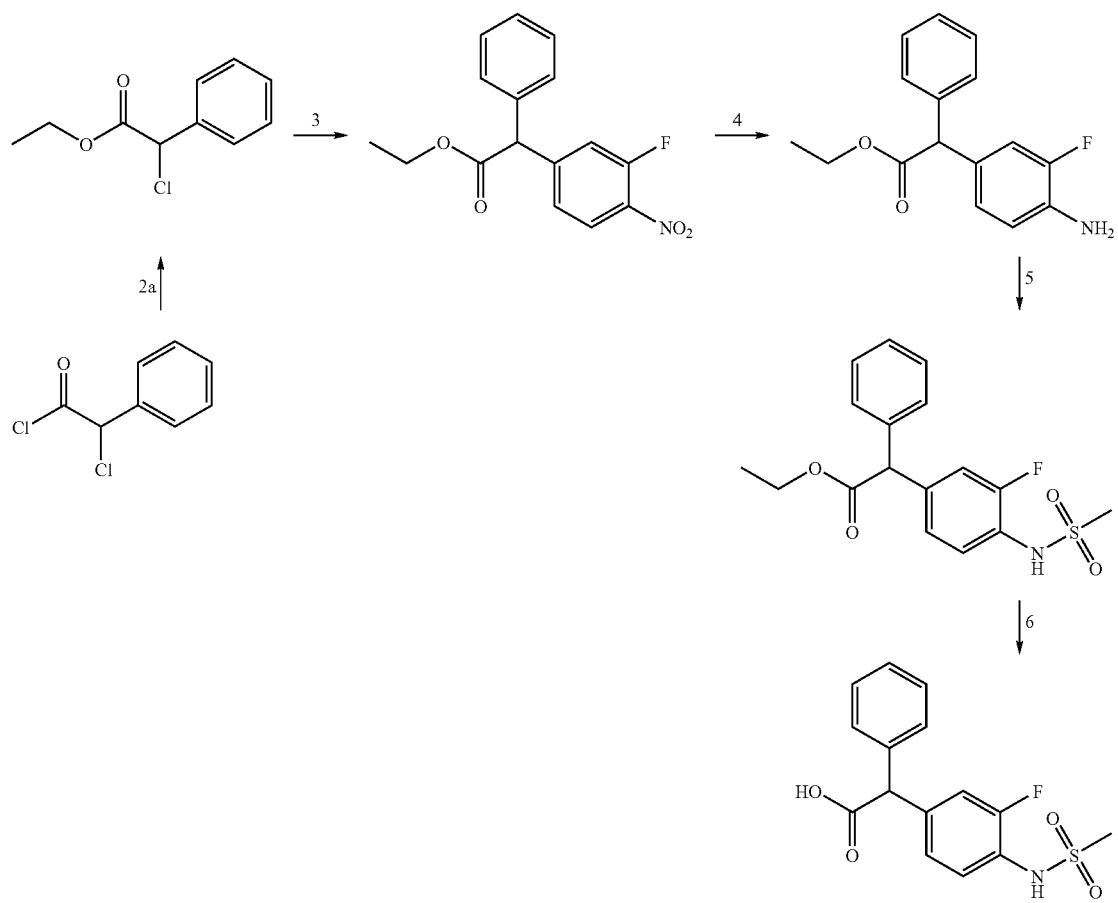

Step 2a: Synthesis of ethyl 2-chloro-2-phenylacetate

To a solution of triethylamine (63.5 mmol, 8.7 mL) in methanol there was added dropwise, at 0° C., α-chlorophenylacetyl chloride (53 mmol, 7.6 mL), and the reaction mixture was then stirred over a period of 3.5 h at room temperature. The reaction mixture was then added to 100 mL of water and extracted with EA (3×100 mL). Following the combination of the organic phases, they were dried over $MgSO_4$ and concentrated in vacuo to give 8.76 g (83.4%) of product.

Step 3: Synthesis of ethyl 2-(3-fluoro-4-nitrophenyl)-2-phenylacetate 9.8 g of potassium tert-butylate were dissolved in 90 mL of DMF and cooled to −45° C. To this, a mixture of ethyl 2-chloro-2-phenylacetate (43.8 mmol, 8.7 g) and 1-fluoro-2-nitrobenzene (43.8 mmol, 4.6 mL) was gently added dropwise and stirring was continued for a further 20 minutes. The reaction mixture was set to pH 4 with aq. 16% strength. HCl, diluted with 25 mL of water, and extracted with EA (3×50 mL). Following combination of the organic phases, they were washed with water and sat. aq. NaCl solution, dried over $MgSO_4$ and concentrated in vacuo. The resulting residue was purified by column chromatography (silica gel: mesh 100-200, eluent: 10% EA in cyclohexane) and yielded 5.9 g (44.9%) of the desired product.

Step 4: Synthesis of ethyl-2-(4-amino-3-fluorophenyl)-2-phenylacetate

Ethyl 2-phenyl-2-(3-fluoro-4-nitrophenyl)acetate was dissolved in a 1:1 mixture of EtOH and EA (465 mL) and hydrogenation was carried out in an H-cube (1 bar, 25° C., 1 mL/min and 0.25 mol/L). Following removal of the solvent and drying, 5.2 g (97.5%) of product were obtained.

Step 5: Synthesis of ethyl 2-phenyl-2-(3-fluoro-4-(methylsulfonamido)-phenyl)acetate The amino compound ethyl 2-(4-amino-3-fluorophenyl)-2-phenylacetate (5.2 g, 19 mmol) was dissolved in 15 mL of pyridine, cooled under a blanket of nitrogen to 0° C., and 2.2 mL of methanesulfonyl chloride (28.5 mmol) were added and the reaction mixture was further stirred at 0° C. over a period of 1 h. To the reaction mixture there were added, with ice cooling, 15 mL of water, and the mixture was set to pH 1 with aq. 16% strength. HCl. Following extraction of the mixture with dichloromethane (3×50 mL), the organic phases were combined, dried over $MgSO_4$ and concentrated in vacuo. Purification of the crude product was carried out by column chromatography (silica gel: 100-200 mesh, eluent: 50% EA in cyclohexane) and yielded 5.8 g (87%) of the desired product.

Step 6: Synthesis of 2-phenyl-2-(3-fluoro-4-(methyl-sulfonamido)-phenyl)acetic acid Ethyl 2-phenyl-2-(3-fluoro-4-(methylsulfonamido)-phenyl)acetate (16.5 mmol, 5.8 g) was dissolved in a mixture of 32 mL of THF and 16 mL of water, 1.18 g of LiOH (49.5 mmol) were added, and the mixture was heated under reflux over a period of 15 h. To the reaction mixture there were added 15 mL of water and the phases were separated. The aqueous phase was acidified with aq. HCl and extracted with dichloromethane (3×50 mL). The combined organic phases were dried over MgSO₄, concentrated, and the residue purified by means of column chromatography (silica gel: 100-200 mesh, eluent: 50% EA in cyclohexane). Yield 3.3 g (61.3%).

6e. Synthesis of (3-Fluoro-4-methanesulfonylamino-phenyl)-o-tolyl-acetic acid

Scheme:

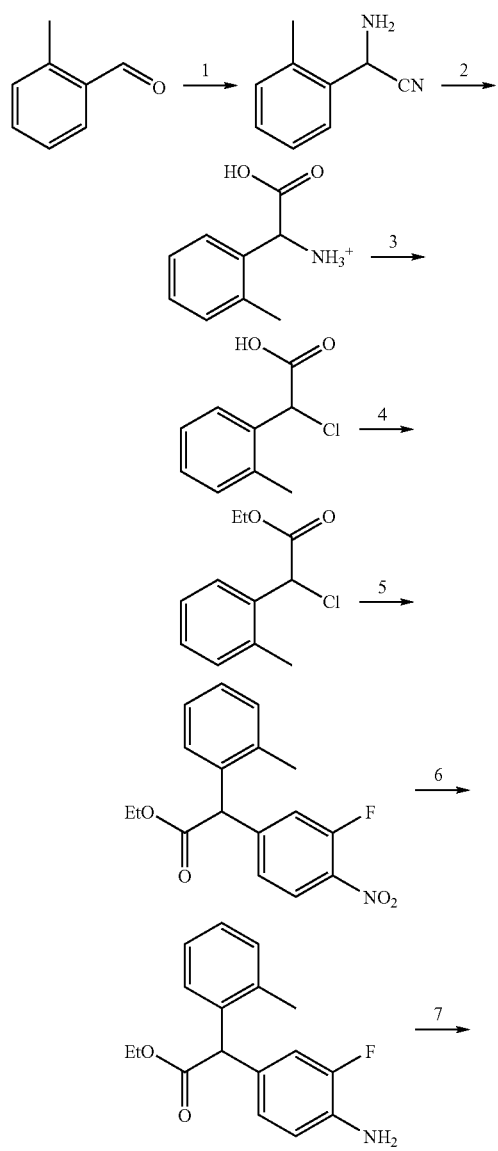

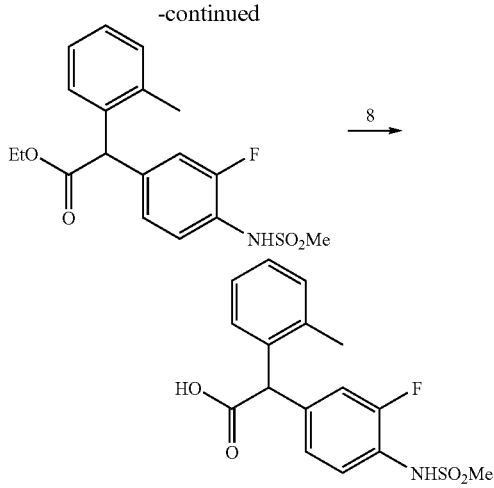

Step 1

Sodium cyanide (6.12 g, 124.8 mmol) was dissolved in water (25 mL) and ammonium chloride (7.35 g, 137.3 mmol) was added to it. Compound 1 (15 g, 124.8 mmol) in methanol (25 mL) was added to the reaction mixture and stirred it at ambient temperature for two days. TLC (5% E.A-Hexane, $R_f$=0.4) showed complete consumption of starting material. Water (100 mL) and benzene (100 mL) was added to the reaction mixture and stirred for 10 minutes. The separated organic layer was dried over anhydrous magnesium sulfate and concentrated under reduced pressure to afford a yellow liquid compound 2. Yield: 17 g (crude).

Step 2

Compound 2 (17 g, crude) was dissolved 6N HCl (110 mL) and refluxed for 20 hours. HCl was removed under reduced pressure. The residue was diluted with ethanol (2×200 mL) and concentrated under reduced pressure. Finally ethyl acetate (250 mL) was added to it and stirred at 70° C. for 1 hour. A solid came out upon cooling and it was filtered through glass-sintered funnel to afford yellow crystalline solid compound 3. Yield: 13 g (crude).

Step 3

Compound 3 (12 g, 59.5 mmol) was dissolved in hydrochloric acid (240 mL) and it was cooled to −5° C. Sodium nitrite solution (7.8 g, 113 mmol) in water (36 mL) was added drop wise over the period of 30 minutes. After complete addition, reaction mixture was stirred at ambient temperature for 3 hours. TLC (in ethyl acetate $R_f$=0.3) showed complete consumption of starting material. The aqueous part was extracted in ethyl acetate (3×250 mL). The organic layer was washed with water (2×200 mL) and finally with brine (200 mL). The washed organic layer was dried over anhydrous magnesium sulfate and concentrated under reduced pressure to afford a yellow solid 4. Yield: 8.5 g (crude).

Step 4

Compound 4 (8 g, 43.5 mmol) was dissolved in benzene (160 mL). Ethanol (80 mL) and sulphuric acid (2 mL) was added to it. The reaction mixture was refluxed for 4 hours. TLC (in 5% E.A-Hexane, $R_f$=0.7) showed complete consumption of starting material. The organic solvent was removed under reduced pressure and the residue was diluted with water (200 mL). The aqueous part was extracted with 20% ethyl acetate in hexane (3×200 mL). The combined organic layer was dried over anhydrous magnesium sulfate and concentrated under reduced pressure to afford a yellow residue, which was purified by column chromatography (silica gel: 100-200 mesh, eluent: 2% ethyl acetate in hexane) to afford a light yellow liquid compound 5. Yield: 6.6 g (72%).

1H NMR (CDCl$_3$, 400 MHz): δ 7.17-7.49 (m, 4H), 5.59 (s, 1H), 4.16-4.30 (m, 2H), 2.42 (s, 3H), 1.24 (t, 3H).

Step 5

To a stirred suspension of potassium tertiary butoxide (7.0 g, 62 mmol) in dimethylformamide (30 mL), a mixture of compound 5 (6.6 g, 31 mmol) and 1-fluoro-2-nitrobenzene (4.38 g, 31 mmol) in dimethylformamide (40 mL) was added at −30° C. The reaction mixture was stirred for 30 minutes at the same temperature. TLC (10% E.A-Hexane, R$_f$=0.6) showed complete consumption of starting material. Reaction mixture was diluted with water (700 mL) and extracted with 20% ethyl acetate in hexane (3×250 mL). Then the organic layer was dried over anhydrous magnesium sulfate. The removal of organic solvent under reduced pressure afforded a yellowish compound, which was purified by column chromatography (silica gel: 100-200 mesh, eluent: 2% ethyl acetate in hexane) to afford a yellow liquid compound 6. Yield: 3.3 g (33.5%)

$^1$H NMR (CDCl$_3$, 400 MHz): δ 7.99 (t, 1H), 7.13-7.25 (m, 5H), 5.22 (s, 1H), 4.20-4.25 (q, 2H), 2.25 (s, 3H), 1.25 (t, 3H).

Step 6

In a 500 mL round bottomed flask compound 6 (3.3 g, 10.4 mmol) dissolved in ethyl acetate (45 mL). Palladium on charcoal (160 mg, 10% Pd) was added under nitrogen atmosphere. It was stirred under atmospheric hydrogen pressure for 12 hours. TLC (20% ethyl acetate in hexane, R$_f$=0.3) showed complete conversion of starting material. The reaction mixture was filtered over celite bed and the bed was washed with ethyl acetate (3×100 mL). The organic layer was concentrated to afford a yellow residue, which was purified through column chromatography (silica gel: 100-200 mesh, eluent: 10% ethyl acetate in hexane) to afford the pure amine compound 7. Yield: 2.4 g (80%).

1H NMR (CDCl$_3$, 400 MHz): δ 7.19-7.27 (m, 4H), 6.89 (d, 1H), 6.82 (d, 1H), 6.72 (t, 1H), 5.07 (s, 1H), 4.19-4.24 (q, 2H), 3.69 (s, 2H), 2.28 (s, 3H), 1.26 (t, 3H).

Step 7

Compound 7 (2.4 g, 8.35 mmol) was dissolved in dichloromethane (40 mL). Pyridine (2 mL, 25 mmol) was added to it. Methane sulphonyl chloride (0.78 mL, 10 mmol) was added drop wise to the reaction mixture at 0° C. and stirred for 16 hours at ambient temperature. TLC (20% ethyl acetate in hexane, R$_f$=0.2) showed complete conversion of starting material. The reaction mixture was diluted with dichloromethane (100 mL) and washed with water (3×70 mL). The organic layer was then dried over anhydrous magnesium sulfate and concentrated to afford a solid compound, which was purified through column chromatography (silica gel: 100-200 mesh, eluent: 15% ethyl acetate in hexane) to afford the pure compound 8. Yield: 2.9 g (95%).

$^1$H NMR (CDCl$_3$, 400 MHz): δ 9.60 (s, 1H), 7.34 (t, 1H), 7.04-7.20 (m, 5H), 5.32 (s, 1H), 4.12-4.19 (m, 2H), 3.02 (s, 3H), 2.21 (s, 3H), 1.16 (t, 3H).

Step 8

Compound 8 (2.9 g, 7.9 mmol), was dissolved in tetrahydrofuran (45 mL). Aqueous lithium hydroxide solution (1M, 24 mL, 24 mmol) was added drop wise at 0° C. to it. The reaction mixture was then stirred at ambient temperature for 16 hours. TLC (30% E.A-Hexane, R$_f$=0.05) showed complete consumption of starting material. The solvent was removed under reduced pressure and residue was diluted with water (80 mL). The aqueous layer was washed with ethyl acetate (150 mL) and aqueous part was acidified with 2N hydrochloric acid up to pH=3-4. The acidified aqueous part was then extracted with ethyl acetate (3×80 mL). The combine organic part was dried over anhydrous magnesium sulfate and concentrated under reduced pressure to afford a white solid compound 9. Yield: 2.2 g (82%).

1H NMR (DMSO-d$_6$, 400 MHz): δ 12.86 (bs, 1H), 9.58 (s, 1H), 7.33 (t, 1H), 7.05-7.23 (m, 6H), 5.22 (s, 1H), 3.01 (s, 3H), 2.22 (s, 3H); Mass (M+1): 338; HPLC purity: 95.73%.

6f. Synthesis of (3-Fluoro-4-methanesulfonylaminophenyl)-m-tolyl-acetic acid

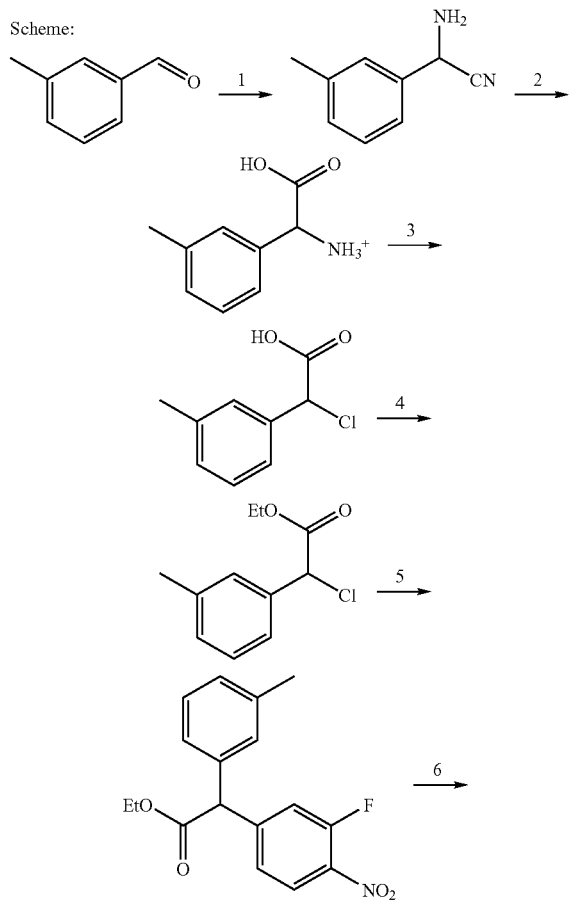

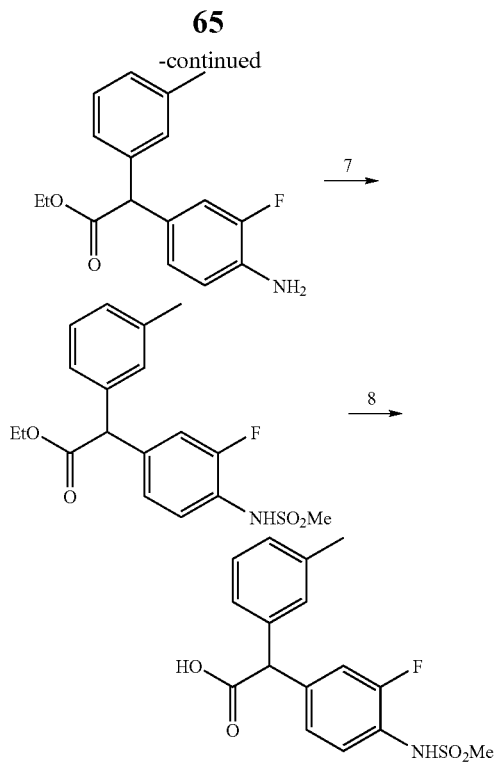

Step 1

Sodium cyanide (6.12 g, 124.8 mmol) was dissolved in water (25 mL) and ammonium chloride (7.35 g, 137.3 mmol) was added to it. Compound 1 (15 g, 124.8 mmol) in methanol (25 mL) was added to the reaction mixture and stirred it at ambient temperature for two days. TLC (5% E.A-Hexane, $R_f$=0.4) showed complete consumption of starting material. Water (100 mL) and benzene (100 mL) was added to the reaction mixture and stirred for 10 minutes. The separated organic layer was dried over anhydrous magnesium sulfate and concentrated under reduced pressure to afford a yellow liquid compound 2. Yield: 17 g (crude).

Step 2

Compound 2 (17 g, crude) was dissolved in 6N HCl (250 mL) and refluxed for 20 hours. HCl was removed under reduced pressure. The residue was diluted with ethanol (2×200 mL) and concentrated under reduced pressure. Finally ethyl acetate (250 mL) was added to it and stirred at 70° C. for 1 hour. A solid came out upon cooling and it was filtered through glass-sintered funnel to afford yellow crystalline solid compound 3. Yield: 13 g (crude).

Step 3

Compound 3 (12 g, 60 mmol) was dissolved in hydrochloric acid (240 mL) and it was cooled to −5° C. Sodium nitrite solution (7.8 g, 113.6 mmol) in water (36 mL) was added drop wise over the period of 30 minutes. After complete addition, reaction mixture was stirred at ambient temperature for 3 hours. TLC (in ethyl acetate $R_f$=0.3) showed complete consumption of starting material. The aqueous part was extracted in ethyl acetate (3×200 mL). The organic layer was washed with water (2×100 mL) and finally with brine (200 mL). The washed organic layer was dried over anhydrous magnesium sulfate and concentrated under reduced pressure to afford a yellow solid 4. Yield: 8.5 g (crude).

Step 4

Compound 4 (8.5 g, 46.2 mmol) was dissolved in benzene (170 mL). Ethanol (85 mL) and sulphuric acid (2 mL) was added to it. The reaction mixture was refluxed for 4 hours. TLC (in 5% E.A-Hexane, $R_f$=0.7) showed complete consumption of starting material. The organic solvent was removed under reduced pressure and the residue was diluted with water (200 mL). The aqueous part was extracted with 20% ethyl acetate in hexane (3×200 mL). The combined organic layer was dried over anhydrous magnesium sulfate and concentrated under reduced pressure to afford a yellow residue, which was purified by column chromatography (silica gel: 100-200 mesh, eluent: 2% ethyl acetate in hexane) to afford a light yellow liquid compound 5. Yield: 6.2 g (63%).

Step 5

To a stirred suspension of potassium tert-butoxide (6.54 g, 58.3 mmol) in dimethylformamide (40 mL), a mixture of compound 5 (6.2 g, 29.15 mmol) and 1-fluoro-2-nitrobenzene (4.12 g, 29.15 mmol) in dimethylformamide (30 mL) was added at −30° C. The reaction mixture was stirred for 30 minutes at the same temperature. TLC (10% E.A-Hexane, $R_f$=0.6) showed complete consumption of starting material. Reaction mixture was diluted with water (700 mL) and extracted with 20% ethyl acetate in hexane (3×200 mL). Then the organic layer was dried over anhydrous magnesium sulfate. The removal of organic solvent under reduced pressure afforded a yellowish compound, which was purified by column chromatography (silica gel: 100-200 mesh, eluent: 2% ethyl acetate in hexane) to afford a yellow liquid compound 6. Yield: 5 g (54%).

1H NMR (CDCl$_3$, 400 MHz): δ 8.00 (t, 1H), 7.06-7.28 (m, 6H), 4.98 (s, 1H), 4.18-4.26 (m, 2H), 2.33 (s, 1H), 1.25 (t, 3H).

Step 6

In a 500 mL round bottomed flask compound 6 (5 g, 15.75 mmol) was dissolved in ethyl acetate (75 mL). Palladium on charcoal (250 mg, 10% Pd) was added under nitrogen atmosphere. It was stirred under atmospheric hydrogen pressure for 12 hours. TLC (20% ethyl acetate in hexane, $R_f$=0.3) showed complete conversion of starting material. The reaction mixture was filtered over celite bed and the bed was washed with ethyl acetate (3×100 mL). The organic layer was concentrated to afford a yellow residue, which was purified through column chromatography (silica gel: 100-200 mesh, eluent: 10% ethyl acetate in hexane) to afford the pure amine compound 7. Yield: 3.8 g (84%).

1H NMR (CDCl$_3$, 400 MHz): δ 7.19 (t, 1H), 7.07 (t, 3H), 6.96 (d, 1H), 6.86 (d, 1H), 6.69 (t, 1H), 4.83 (s, 1H), 4.15-4.21 (q, 2H), 3.66 (s, 2H), 2.31 (s, 3H), 1.24 (t, 3H).

Step 7

Compound 7 (3.8 g, 13.22 mmol) was dissolved in dichloromethane (60 mL). Pyridine (3.4 mL, 39.66 mmol) was added to it. Methane sulphonyl chloride (1.8 g, 15.87 mmol) was added drop wise to the reaction mixture at 0° C. and stirred for 16 hours at ambient temperature. TLC (20% ethyl acetate in hexane, $R_f$=0.2) showed complete conversion of starting material. The reaction mixture was diluted with dichloromethane (200 mL) and washed with water (3×200 mL). The organic layer was then dried over anhydrous magnesium sulfate and concentrated to afford a solid compound, which was purified through column chromatography (silica gel: 100-200 mesh, eluent: 15% ethyl acetate in hexane) to afford the pure compound 8. Yield: 4.5 g (93%).

$^1$H NMR (CDCl$_3$, 400 MHz): δ 9.59 (s, 1H), 7.34 (t, 1H), 7.21-7.25 (m, 2H), 7.07-7.16 (m, 4H), 5.17 (s, 1H), 4.11-4.16 (q, 2H), 3.01 (s, 3H), 2.27 (s, 3H), 1.17 (t, 3H).

Step 8

Compound 8 (4.5 g, 12.3 mmol), was dissolved in tetrahydrofuran (70 mL). Aqueous lithium hydroxide solution (1M, 37 mL, 37 mmol) was added drop wise at 0° C. to it. The reaction mixture was then stirred at ambient temperature for 16 hours. TLC (30% E.A-Hexane, $R_f$=0.05) showed complete consumption of starting material. The solvent was removed under reduced pressure and residue was diluted with water (150 mL). The aqueous layer was washed with ethyl acetate (150 mL) and aqueous part was acidified with 2N hydrochloric acid up to pH=3-4. The acidified aqueous part was then extracted with ethyl acetate (3×100 mL). The combine organic part was dried over anhydrous magnesium sulfate and concentrated under reduced pressure to afford a white solid compound 9. Yield: 3.9 g (80%).

1H NMR (DMSO-d$_6$, 400 MHz): δ 12.81 (bs, 1H), 9.55 (s, 1H), 7.32 (t, 1H), 7.06-7.24 (m, 5H), 5.04 (s, 1H), 3.00 (s, 3H), 2.28 (s, 3H); Mass (M+1): 338; HPLC purity: 98.37%.

6.g. Synthesis of (3-Fluoro-4-methanesulfonylamino-phenyl)-(3-fluoro-phenyl)-acetic acid

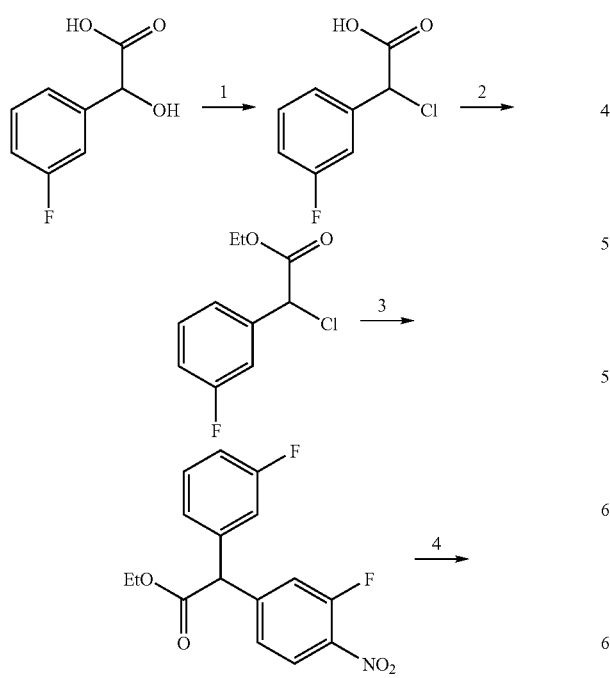

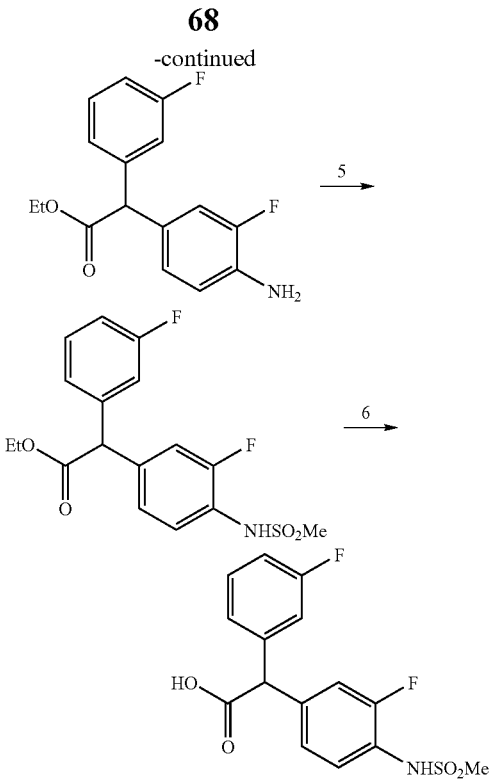

Step 1

Compound 1 (12 g, 70.5 mmol), was dissolved in tetrahydrofuran (120 mL). Thionyl chloride (10 g, 84.6 mmol) was added to it. Catalytic amount of DMF (1 mL) was added to the reaction mixture. The reaction mixture was stirred at ambient temperature for overnight. The organic solvent was removed under reduced pressure; the residue was diluted with water (200 mL) and extracted with dichloromethane (2×200 mL). The combined organic layer was dried over anhydrous magnesium sulfate and concentrated under reduced pressure to afford compound 2. Yield: 12 g (crude).

Step 2

Compound 2 (12 g, crude) was dissolved in benzene (240 mL). Ethanol (120 mL) and sulphuric acid (2 mL) was added to it. The reaction mixture was refluxed for 4 hours using Dean stark apparatus. TLC (5% E.A-Hexane, $R_f$=0.7) showed complete consumption of starting material. The organic solvent was removed under reduced pressure and the residue was diluted with water (200 mL). The aqueous part was extracted with 20% ethyl acetate in hexane (3×200 mL). The combined organic layer was dried over anhydrous magnesium sulfate and concentrated under reduced pressure to afford a yellow residue, which was purified by column chromatography (silica gel: 100-200 mesh, eluent: 2% ethyl acetate in hexane) to afford a light yellow liquid compound 3. Yield: 8.2 g (59.5%).

Step 3

To a stirred suspension of potassium tertiary butoxide (8.5 g, 75.75 mmol) in dimethylformamide (50 mL), a mixture of compound 3 (8.2 g, 38 mmol) and 1-fluoro-2-nitrobenzene (5.34 g, 38 mmol) in dimethylformamide (30 mL) was added at −30° C. The reaction mixture was stirred for 30 minutes at the same temperature. TLC (10% E.A-Hexane, $R_f$=0.6) showed complete consumption of starting material. Reaction mixture was diluted with water (800 mL) and extracted with 20% ethyl acetate in hexane (3×200 mL). Then the organic layer was dried over anhydrous magnesium sulfate. The removal of organic solvent under reduced pressure afforded a brown liquid compound, which was purified by column chromatography (silica gel: 100-200 mesh, eluent: 2% ethyl acetate in hexane) to afford a light brown liquid compound 4. Yield: 3.2 g (26%)

Step 4

In a 250 mL round bottomed flask compound 4 (3.2 g, 10 mmol) was dissolved in ethyl acetate (50 mL). Palladium on charcoal (150 mg, 10% Pd) was added under nitrogen atmosphere. It was stirred under atmospheric hydrogen pressure for 12 hours. TLC (20% ethyl acetate in hexane, $R_f$=0.3) showed complete conversion of starting material. The reaction mixture was filtered over celite bed and the bed was washed with ethyl acetate (3×50 mL). The organic layer was concentrated to afford a yellow residue, which was purified through column chromatography (silica gel: 100-200 mesh, eluent: 10% ethyl acetate in hexane) to afford the pure amine compound 5. Yield: 2.3 g (79%).

Step 5

Compound 5 (2.3 g, 7.8 mmol) was dissolved in dichloromethane (35 mL). Pyridine (1.9 mL, 23.4 mmol) was added to it. Methane sulphonyl chloride (1.1 g, 9.4 mmol) was added drop wise to the reaction mixture at 0° C. and stirred for 16 hours at ambient temperature. TLC (20% ethyl acetate in hexane, $R_f$=0.2) showed complete consumption of starting material. The reaction mixture was diluted with dichloromethane (100 mL) and washed with water (3×50 mL). The organic layer was then dried over anhydrous magnesium sulfate and concentrated to afford a solid compound, which was purified through column chromatography (silica gel: 100-200 mesh, eluent: 15% ethyl acetate in hexane) to afford the pure compound 6. Yield: 2.8 g (96%).

$^1$H NMR (CDCl$_3$, 400 MHz): δ 7.55 (t, 1H), 7.30-7.35 (q, 1H), 6.98-7.18 (m, 5H), 6.50 (s, 1H), 4.21-4.27 (q, 2H), 3.04 (s, 3H), 1.28 (t, 3H).

Step 6

Compound 6 (2.8 g, 7.5 mmol), was dissolved in tetrahydrofuran (30 mL). Aqueous lithium hydroxide solution (1M, 23 mL, 23 mmol) was added drop wise at 0° C. to it. The reaction mixture was then stirred at ambient temperature for 16 hours. TLC (30% E.A-Hexane, $R_f$=0.05) showed complete consumption of starting material. The solvent was removed under reduced pressure and residue was diluted with water (70 mL). The aqueous layer was washed with ethyl acetate (70 mL) and aqueous part was acidified with 2N hydrochloric acid up to pH=3-4. The acidified aqueous part was then extracted with ethyl acetate (3×150 mL). The combine organic part was dried over anhydrous magnesium sulfate and concentrated under reduced pressure to afford a white solid compound 7. Yield: 1.8 g (70%).

1H NMR (DMSO-d$_6$, 400 MHz): δ 12.99 (bs, 1H), 9.58 (s, 1H), 7.08-7.41 (m, 7H), 5.16 (s, 1H), 3.01 (s, 3H); Mass (M+1): 342; HPLC purity: 96.99%.

6.h. Synthesis of 2-(3-Fluoro-4-methanesulfony-lamino-phenyl)-3-phenyl-propionic acid

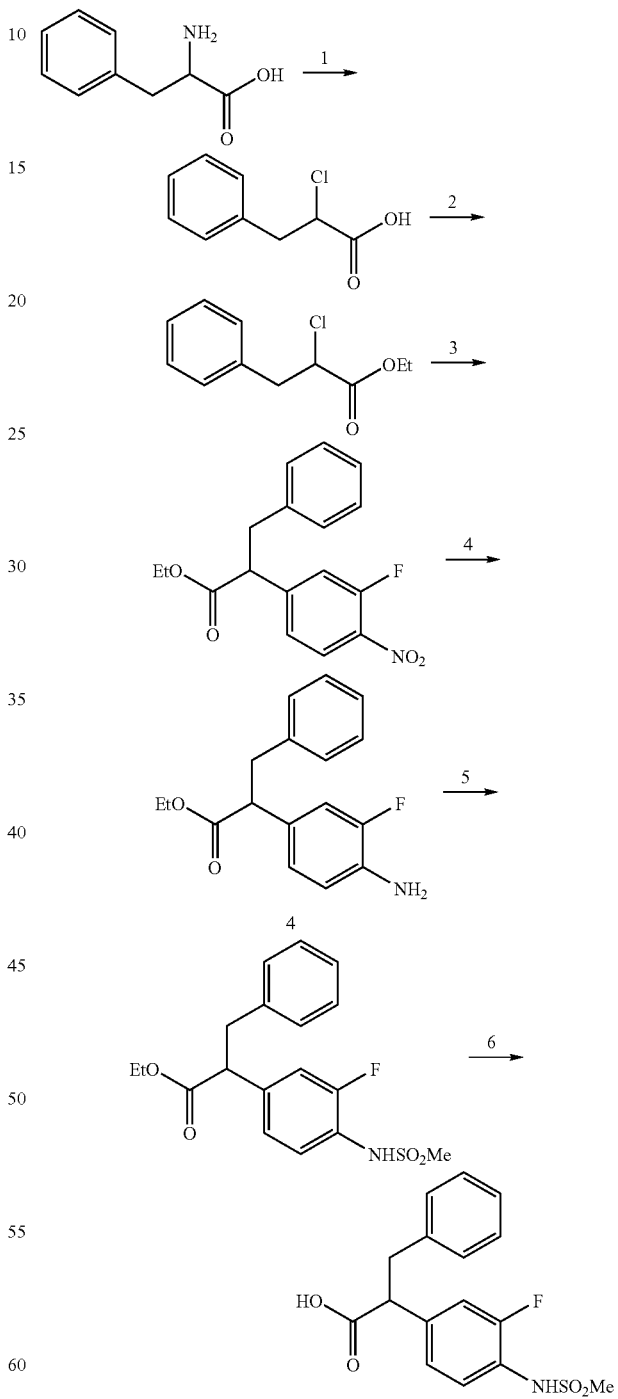

Step 1

Compound 1 (10 g, 60.5 mmol) was dissolved in concentrated hydrochloric acid (200 mL) and was cooled to −5° C.

Sodium nitrite solution (7.9 g, 115 mmol) in water (30 mL) was added drop wise over the period of 30 minutes. After complete addition reaction mixture was stirred at ambient temperature for 2 hours. TLC (in 50% E.A-Hexane, $R_f$=0.4) showed complete consumption of starting material. The aqueous part was extracted in ethyl acetate (3×200 mL). The overall organic layer was washed with water (2×200 mL) and finally with brine (200 mL). The washed organic layer was dried over anhydrous magnesium sulfate and concentrated under reduced pressure to afford a yellow liquid 2. Yield: 12 g (crude).

Step 2

Compound 2 (12 g, 65 mmol) dissolved in benzene (240 mL). Ethanol (120 mL) and sulphuric acid (2 mL) was added to it. The reaction mixture was refluxed for 4 hours using Deanstark apparatus. TLC (20% ethyl acetate in hexane, $R_f$=0.6) showed complete consumption of starting material. The organic solvent was concentrated under reduced pressure and the residue was diluted with water (200 mL). The aqueous layer was extracted with 30% ethyl acetate in hexane (3×200 mL). The overall organic layer was dried over anhydrous magnesium sulfate and concentrated under reduced pressure to get a yellowish residue, which was purified by column chromatography (silica gel: 100-200 mesh; eluent: 2% ethyl acetate in hexane) to afford a light yellow liquid compound 3. Yield: 10 g (87%).
$^1$H NMR (CDCl$_3$, 400 MHz): δ 7.23-7.35 (m, 5H), 4.81 (q, 1H), 4.11 (q, 2H), 3.10-3.34 (m, 2H), 1.14 (t, 3H).

Step 3

To a stirred suspension of potassium tert-butoxide (14.3 g, 127 mmol) in dimethylformamide (90 mL), a mixture of compound 3 (13.5 g, 63.5 mmol) and 1-fluoro 2-nitrobenzene (7.12 g, 63.5 mmol) in DMF (50 mL) was added at −30° C. The reaction mixture was stirred for 30 minute at the same temperature. TLC (10% E.A-Hexane, $R_f$=0.4) showed complete consumption of starting material. Reaction mixture was diluted with water (1.5 L) and extracted with 20% ethyl acetate in hexane (3×250 mL). Then the organic layer was dried over anhydrous magnesium sulfate. The removal of organic solvent under reduced pressure afforded a yellowish compound, which was purified by column chromatography (silica gel: 100-200 mesh, eluent: 2% ethyl acetate in hexane) to afford a light brown solid 4. Yield: 14.5 g (72%).
$^1$H NMR (CDCl$_3$, 400 MHz): δ 6.64-7.24 (m, 8H), 3.96 (q, 2H), 3.77 (t, 1H), 3.18 (q, 1H), 2.90 (q, 1H), 1.02 (t, 3H).

Step 4

In a 500 mL round bottomed flask compound 4 (14.5 g, 45.7 mmol) was dissolved in ethyl acetate (300 mL). Palladium on charcoal (0.7 g, 10% Pd) was added under nitrogen atmosphere. It was stirred under atmospheric hydrogen pressure for 12 hours. TLC (20% ethyl acetate in hexane, $R_f$=0.4) showed complete conversion of starting material. Reaction mixture was filtered over celite bed and washed with ethyl acetate (3×150 mL). The organic layer was concentrated to afford a yellowish residue, which was purified through column chromatography (silica gel: 100-200 mesh, eluent: 10% ethyl acetate in hexane) to afford the pure amine compound 5. Yield: 12.5 g (95%).

$^1$H NMR (CDCl$_3$, 400 MHz): δ 6.64-7.24 (m, 8H), 5.06 (s, 2H), 3.96 (q, 2H), 3.77 (t, 1H), 3.18 (q, 1H), 2.90 (q, 1H), 1.02 (t, 3H).

Step 5

Compound 5 (12.5 g, 43.5 mmol) was dissolved in dichloromethane (190 mL). Pyridine (10.5 mL, 130.5 mmol) was added to it. Methane sulphonyl chloride (6 g, 47.85 mmol) was added drop wise to the reaction mixture at 0-5° C. and stirred for 16 hours at ambient temperature. TLC (20% ethyl acetate in hexane, $R_f$=0.2) showed complete conversion of starting material. Reaction mixture was diluted with dichloromethane (200 mL) and washed with water (3×200 mL). The organic layer was then dried over anhydrous magnesium sulfate and concentrated to afford a solid compound, which was purified through column chromatography (silica gel: 100-200 mesh, eluent: 20% ethyl acetate in hexane) to afford the pure compound 6. Yield: 13.5 g (85%).
$^1$H NMR (CDCl$_3$, 400 MHz): δ 9.57 (s, 1H), 7.14-7.34 (m, 8H), 3.94-4.04 (m, 3H), 3.25 (q, 1H), 2.97-3.02 (m, 4H), 1.03 (t, 3H).

Step 6

Compound 6 (4 g, 11 mmol), was dissolved in tetrahydrofuran (60 mL). Lithium hydroxide solution (1M, 33 mL, 33 mmol) was added drop wise at 10-15° C. to it. The reaction mixture was then stirred at ambient temperature for 16 hours. TLC (in 30% E.A-Hexane, $R_f$=0.05) showed complete consumption of starting material. The solvent was removed under reduced pressure and residue was diluted with water (150 mL). The aqueous layer was washed with ethyl acetate (150 mL) and aqueous part was acidified with 2N aqueous hydrochloric acid solution up to pH=3-4. The acidified aqueous part was then extracted with ethyl acetate (3×150 mL). The organic layer was dried over anhydrous magnesium sulfate and concentrated under reduced pressure afforded a white solid compound 7. Yield: 3 g (81%).
$^1$H NMR (CDCl$_3$, 400 MHz): δ 12.53 (s, 1H), 9.56 (s, 1H), 7.15-7.33 (m, 8H), 3.91 (t, 1H), 3.26 (q, 1H), 3.00 (s, 3H), 2.96 (t, 1H). MS m/z (M+1): 338; HPLC purity 98.27%.

7. General Instructions for the Reaction of Amines of the General Formulas V with Carboxylic Acids of the General Formula VII The acid of the general formula VII (1 equivalent), the amine of the general formulas V (1.2 equivalents) and EDCl (1.2 equivalents) are stirred in DMF (10 mmol of acid in 20 mL) over a period of 12 hours at RT, and water is then added. The reaction mixture is extracted with EA a number of times, the aqueous phase is saturated with NaCl and then again extracted with EA. The combined organic phases are washed with 1N hydrochloric acid and sat. aq. NaCl soln., dried over MgSO$_4$, and the solvent is removed in vacuo. The residue is purified by means of flash chromatography (SiO$_2$, EA/hexane 1:2).

The following illustrative compounds 1-8, 13-16, 21, 22, 34, 35, 40-42, 60, 61, 77, 86 were obtained in accordance with the aforementioned general instructions.

The other illustrative compounds 9-12, 17-20, 23-33, 36-39, 43-59, 62-76, 78-85, 87-89 can be obtained by the methods described above.

[1] 2-Cyclohexyl-2-(3-fluoro-4-(methylsulfonamido)phenyl)-N-((2-(4-methylpiperidin-1-yl)-6-(trifluoromethyl)pyridin-3-yl)methyl)acetamide; [M + H] 585
[2] 2-Cyclohexyl-N-((2-(cyclohexylthio)-6-(trifluoromethyl)pyridin-3-yl)methyl)-2-(3-fluoro-4-(methylsulfonamido)phenyl)acetamide; [M + H] 602
[3] 2-(3-Fluoro-4-(methylsulfonamido)phenyl)-N-((2-(4-methylpiperidin-1-yl)-6-(trifluoromethyl)pyridin-3-yl)methyl)-2-phenylacetamide; [M + H] 579
[4] N-((2-(Cyclohexylthio)-6-(trifluoromethyl)pyridin-3-yl)methyl)-2-(3-fluoro-4-(methylsulfonamido)phenyl)-2-phenylacetamide; [M + H] 596
[5] 2-(3-Fluoro-4-(methylsulfonamido)phenyl)-2-methyl-N-((2-(4-methylpiperidin-1-yl)-6-(trifluoromethyl)pyridin-3-yl)methyl)propanamide, [M + H] 531
[6] N-((2-(Cyclohexylthio)-6-(trifluoromethyl)pyridin-3-yl)methyl)-2-(3-fluoro-4-(methylsulfonamido)phenyl)-2-methylpropanamide, [M + H] 549
[7] 2-(3-Fluoro-4-(methylsulfonamido)phenyl)-2-methyl-N-((2-(4-methylpiperidin-1-yl)-6-(trifluoromethyl)pyridin-3-yl)methyl)butanamide, [M + H] 545
[8] N-((2-(Cyclohexylthio)-6-(trifluoromethyl)pyridin-3-yl)methyl)-2-(3-fluoro-4-(methylsulfonamido)phenyl)-2-methylbutanamide, [M + H] 562
[9] 1-(3-Fluoro-4-(methylsulfonamido)phenyl)-N-((2-(4-methylpiperidin-1-yl)-6-(trifluoromethyl)pyridin-3-yl)methyl)cyclopropanecarboxamide,
[10] N-((2-(Cyclohexylthio)-6-(trifluoromethyl)pyridin-3-yl)methyl)-1-(3-fluoro-4-(methylsulfonamido)phenyl)cyclopropanecarboxamide,
[11] 1-(3-Fluoro-4-(methylsulfonamido)phenyl)-N-((2-(4-methylpiperidin-1-yl)-6-(trifluoromethyl)pyridin-3-yl)methyl)cyclobutanecarboxamide,
[12] N-((2-(Cyclohexylthio)-6-(trifluoromethyl)pyridin-3-yl)methyl)-1-(3-fluoro-4-(methylsulfonamido)phenyl)cyclobutanecarboxamide,
[13] 1-(3-Fluoro-4-(methylsulfonamido)phenyl)-N-((2-(4-methylpiperidin-1-yl)-6-(trifluoromethyl)pyridin-3-yl)methyl)cyclopentanecarboxamide, [M + H] 557
[14] N-((2-(Cyclohexylthio)-6-(trifluoromethyl)pyridin-3-yl)methyl)-1-(3-fluoro-4-(methylsulfonamido)phenyl)cyclopentanecarboxamide, [M + H] 575
[15] 1-(3-Fluoro-4-(methylsulfonamido)phenyl)-N-((2-(4-methylpiperidin-1-yl)-6-(trifluoromethyl)pyridin-3-yl)methyl)cyclohexanecarboxamide, [M + H] 572
[16] N-((2-(Cyclohexylthio)-6-(trifluoromethyl)pyridin-3-yl)methyl)-1-(3-fluoro-4-(methylsulfonamido)phenyl)cyclohexanecarboxamide, [M + H] 588
[17] 2-Cyclopropyl-2-(3-fluoro-4-(methylsulfonamido)phenyl)-N-((2-(4-methylpiperidin-1-yl)-6-(trifluoromethyl)pyridin-3-yl)methyl)acetamide,
[18] N-((2-(Cyclohexylthio)-6-(trifluoromethyl)pyridin-3-yl)methyl)-2-cyclopropyl-2-(3-fluoro-4-(methylsulfonamido)phenyl)acetamide,
[19] 2-Cyclobutyl-2-(3-fluoro-4-(methylsulfonamido)phenyl)-N-((2-(4-methylpiperidin-1-yl)-6-(trifluoromethyl)pyridin-3-yl)methyl)acetamide,
[20] 2-Cyclobutyl-N-((2-(cyclohexylthio)-6-(trifluoromethyl)pyridin-3-yl)methyl)-2-(3-fluoro-4-(methylsulfonamido)phenyl)acetamide,
[21] 2-Cyclopentyl-2-(3-fluoro-4-(methylsulfonamido)phenyl)-N-((2-(4-methylpiperidin-1-yl)-6-(trifluoromethyl)pyridin-3-yl)methyl)acetamide, [M + H] 572
[22] N-((2-(Cyclohexylthio)-6-(trifluoromethyl)pyridin-3-yl)methyl)-2-cyclopentyl-2-(3-fluoro-4-(methylsulfonamido)phenyl)acetamide, [M + H] 589
[23] 2-(3-Fluoro-4-(methylsulfonamido)phenyl)-N-((2-(4-methylpiperidin-1-yl)-6-(trifluoromethyl)pyridin-3-yl)methyl)-2-morpholinoacetamide,
[24] N-((6-tert-Butyl-2-(4-methylpiperidin-1-yl)pyridin-3-yl)methyl)-2-(3-fluoro-4-(methylsulfonamido)phenyl)-2-phenylacetamide,
[25] 2-(3-Fluoro-4-(methylsulfonamido)phenyl)-N-(2-(4-methylpiperidin-1-yl)-4-(trifluoromethyl)benzyl)-2-phenylacetamide,
[26] N-(4-tert-Butyl-2-(4-methylpiperidin-1-yl)benzyl)-2-(3-fluoro-4-(methylsulfonamido)phenyl)-2-phenylacetamide,
[27] 2-(3-Fluoro-4-(methylsulfonamido)phenyl)-N-((2-(4-methylpiperidin-1-yl)-6-(trifluoromethyl)pyridin-3-yl)methyl)-2-(pyridin-2-yl)acetamide,
[28] 2-(3-Fluoro-4-(methylsulfonamido)phenyl)-N-((2-(4-methylpiperidin-1-yl)-6-(trifluoromethyl)pyridin-3-yl)methyl)-2-(pyridin-3-yl)acetamide,
[29] 2-(3-Fluoro-4-(methylsulfonamido)phenyl)-N-((2-(4-methylpiperidin-1-yl)-6-(trifluoromethyl)pyridin-3-yl)methyl)-2-(pyridin-4-yl)acetamide,
[30] N-((2-(Cyclohexylthio)-6-(trifluoromethyl)pyridin-3-yl)methyl)-2-(3-fluoro-4-(methylsulfonamido)phenyl-2-(pyridin-2-yl)acetamide,
[31] N-((2-(Cyclohexylthio)-6-(trifluoromethyl)pyridin-3-yl)methyl)-2-(3-fluoro-4-(methylsulfonamido)phenyl)-2-(pyridin-3-yl)acetamide,
[32] N-((2-(Cyclohexylthio)-6-(trifluoromethyl)pyridin-3-yl)methyl)-2-(3-fluoro-4-(methylsulfonamido)phenyl)-2-(pyridin-4-yl)acetamide,
[33] 2-(3-Fluoro-4-(methylsulfonamido)phenyl)-2-(2-fluorophenyl)-N-((2-(4-methylpiperidin-1-yl)-6-(trifluoromethyl)pyridin-3-yl)methyl)acetamide,
[34] 2-(3-Fluoro-4-(methylsulfonamido)phenyl)-2-(3-fluorophenyl)-N-((2-(4-methylpiperidin-1-yl)-6-(trifluoromethyl)pyridin-3-yl)methyl)acetamide, [M + H] 598
[35] 2-(3-Fluoro-4-(methylsulfonamido)phenyl)-2-(4-fluorophenyl)-N-((2-(4-methylpiperidin-1-yl)-6-(trifluoromethyl)pyridin-3-yl)methyl)acetamide, [M + H] 598
[36] 2-(3-Chlorphenyl)-2-(3-fluoro-4-(methylsulfonamido)phenyl)-N-((2-(4-methylpiperidin-1-yl)-6-(trifluoromethyl)pyridin-3-yl)methyl)acetamide,
[37] 2-(4-Chlorphenyl)-2-(3-fluoro-4-(methylsulfonamido)phenyl)-N-((2-(4-methylpiperidin-1-yl)-6-(trifluoromethyl)pyridin-3-yl)methyl)acetamide,
[38] 2-(3-Bromphenyl)-2-(3-fluoro-4-(methylsulfonamido)phenyl)-N-((2-(4-methylpiperidin-1-yl)-6-(trifluoromethyl)pyridin-3-yl)methyl)acetamide,
[39] 2-(4-Bromphenyl)-2-(3-fluoro-4-(methylsulfonamido)phenyl)-N-((2-(4-methylpiperidin-1-yl)-6-trifluoromethyl)pyridin-3-yl)methyl)acetamide,
[40] 2-(3-Fluoro-4-(methylsulfonamido)phenyl)-N-((2-(4-methylpiperidin-1-yl)-6-(trifluoromethyl)pyridin-3-yl)methyl)-2-o-tolylacetamide, [M + H] 594

-continued

[41] 2-(3-Fluoro-4-(methylsulfonamido)phenyl)-N-((2-(4-methylpiperidin-1-yl)-6-(trifluoromethyl)pyridin-3-yl)methyl)-2-m-tolylacetamide, [M + H] 594
[42] 2-(3-Fluoro-4-(methylsulfonamido)phenyl)-N-((2-(4-methylpiperidin-1-yl)-6-(trifluoromethyl)pyridin-3-yl)methyl)-2-p-tolylacetamide, [M + H] 594
[43] 2-(3-Fluoro-4-(methylsulfonamido)phenyl)-N-((2-(4-methylpiperidin-1-yl)-6-(trifluoromethyl)pyridin-3-yl)methyl)-2-(3-trifluoromethyl)phenyl)acetamide,
[44] 2-(3-Fluoro-4-(methylsulfonamido)phenyl)-N-((2-(4-methylpiperidin-1-yl)-6-(trifluoromethyl)pyridin-3-yl)methyl)-2-(4-(trifluoromethyl)phenyl)acetamide,
[45] 2-(3-Fluoro-4-(methylsulfonamido)phenyl)-2-(4-hydroxyphenyl)-N-((2-(4-methylpiperidin-1-yl)-6-(trifluoromethyl)pyridin-3-yl)methyl)acetamide,
[46] 2-(3-Fluoro-4-(methylsulfonamido)phenyl)-2-(4-methoxyphenyl)-N-((2-(4-methylpiperidin-1-yl)-6-(trifluoromethyl)pyridin-3-yl)methyl)acetamide,
[47] 2-(3-Fluoro-4-(methylsulfonamido)phenyl)-2-(3-hydroxy-4-methoxyphenyl)-N-((2-(4-methylpiperidin-1-yl)-6-(trifluoromethyl)pyridin-3-yl)methyl)acetamide,
[48] 2-(3-Fluoro-4-(methylsulfonamido)phenyl)-2-(4-hydroxy-3-methoxyphenyl)-N-((2-(4-methylpiperidin-1-yl)-6-(trifluoromethyl)pyridin-3-yl)methyl)acetamide,
[49] 2-(3-Fluoro-4-(methylsulfonamido)phenyl)-N-((2-(4-methylpiperidin-1-yl)-6-(trifluoromethyl)pyridin-3-yl)methyl)-2-(4-phenoxyphenyl)acetamide,
[50] 2-(3-Fluoro-4-(methylsulfonamido)phenyl)-N-((2-(4-methylpiperidin-1-yl)-6-(trifluoromethyl)pyridin-3-yl)methyl)-2-(thiophen-2-yl)acetamide,
[51] 2-(3-Fluoro-4-(methylsulfonamido)phenyl)-N-((2-(4-methylpiperidin-1-yl)-6-(trifluoromethyl)pyridin-3-yl)methyl)-2-(thiophen-3-yl)acetamide,
[52] N-((2-(Cyclohexylthio)-6-(trifluoromethyl)pyridin-3-yl)methyl)-2-(3-fluoro-4-(methylsulfonamido)phenyl)-2-(2-fluorophenyl)acetamide,
[53] N-((2-(Cyclohexylthio)-6-(trifluoromethyl)pyridin-3-yl)methyl)-2-(3-fluoro-4-(methylsulfonamido)phenyl)-2-(3-fluorophenyl)acetamide,
[54] N-((2-(Cyclohexylthio)-6-(trifluoromethyl)pyridin-3-yl)methyl)-2-(3-fluoro-4-(methylsulfonamido)phenyl)-2-(4-fluorophenyl)acetamide,
[55] 2-(3-Chlorphenyl)-N-((2-(Cyclohexylthio)-6-(trifluoromethyl)pyridin-3-yl)methyl)-2-(3-fluoro-4-(methylsulfonamido)phenyl)acetamide,
[56] 2-(4-Chlorphenyl)-N-((2-(cyclohexylthio)-6-(trifluoromethyl)pyridin-3-yl)methyl)-2-(3-fluoro-4-(methylsulfonamido)phenyl)acetamide,
[57] 2-(3-Bromphenyl)-N-((2-(Cyclohexylthio)-6-(trifluoromethyl)pyridin-3-yl)methyl)-2-(3-fluoro-4-(methylsulfonamido)phenyl)acetamide,
[58] 2-(4-Bromophenyl)-N-((2-(cyclohexylthio)-6-(trifluoromethyl)pyridin-3-yl)methyl)-2-(3-fluoro-4-(methylsulfonamido)phenyl)acetamide,
[59] N-((2-(Cyclohexylthio)-6-(trifluoromethyl)pyridin-3-yl)methyl)-2-(3-fluoro-4-(methylsulfonamido)phenyl)-2-o-tolylacetamide,
[60] N-((2-(Cyclohexylthio)-6-(trifluoromethyl)pyridin-3-yl)methyl)-2-(3-fluoro-4-(methylsulfonamido)phenyl)-2-m-tolylacetamide, [M + H] 611
[61] N-((2-(Cyclohexylthio)-6-(trifluoromethyl)pyridin-3-yl)methyl)-2-(3-fluoro-4-(methylsulfonamido)phenyl)-2-p-tolylacetamide, [M + H] 611
[62] N-((2-(Cyclohexylthio)-6-(trifluoromethyl)pyridin-3-yl)methyl)-2-(3-fluoro-4-(methylsulfonamido)phenyl)-2-(3-(trifluoromethyl)phenyl)acetamide,
[63] N-((2-(Cyclohexylthio)-6-(trifluoromethyl)pyridin-3-yl)methyl)-2-(3-fluoro-4-(methylsulfonamido)phenyl)-2-(4-(trifluoromethyl)phenyl)acetamide,
[64] N-((2-(Cyclohexylthio)-6-(trifluoromethyl)pyridin-3-yl)methyl)-2-(3-fluoro-4-(methylsulfonamido)phenyl)-2-(4-hydroxyphenyl)acetamide,
[65] N-((2-(Cyclohexylthio)-6-(trifluoromethyl)pyridin-3-yl)methyl)-2-(3-fluoro-4-(methylsulfonamido)phenyl)-2-(4-methoxyphenyl)acetamide,
[66] N-((2-(Cyclohexylthio)-6-(trifluoromethyl)pyridin-3-yl)methyl)-2-(3-fluoro-4-(methylsulfonamido)phenyl)-2-(3-hydroxy-4-methoxyphenyl)acetamide,
[67] N-((2-(Cyclohexylthio)-6-(trifluoromethyl)pyridin-3-yl)methyl)-2-(3-fluoro-4-(methylsulfonamido)phenyl)-2-(4-hydroxy-3-methoxyphenyl)acetamide,
[68] N-((2-(Cyclohexylthio)-6-(trifluoromethyl)pyridin-3-yl)methyl)-2-(3-fluoro-4-(methylsulfonamido)phenyl)-2-(4-phenoxyphenyl)acetamide,
[69] 2-(3-Fluoro-4-(methylsulfonamido)phenyl)-N-((2-(4-methylpiperidin-1-yl)-6-(trifluoromethyl)pyridin-3-yl)methyl)-2-(thiophen-2-yl)acetamide,
[70] 2-(3-Fluoro-4-(methylsulfonamido)phenyl)-N-((2-(4-methylpiperidin-1-yl)-6-(trifluoromethyl)pyridin-3-yl)methyl)-2-(thiophen-3-yl)acetamide,
[71] N-((2-(Cyclohexylthio)-6-(trifluoromethyl)pyridin-3-yl)methyl)-2-(3-fluoro-4-(methylsulfonamido)phenyl)-2-(thiophen-2-yl)acetamide,
[72] N-((2-(Cyclohexylthio)-6-(trifluoromethyl)pyridin-3-yl)methyl)-2-(3-fluoro-4-(methylsulfonamido)phenyl)-2-(thiophen-3-yl)acetamide,
[73] 2-(3-Fluoro-4-(methylsulfonamido)phenyl)-N-((2-(4-methylpiperidin-1-yl)-6-(trifluoromethyl)pyridin-3-yl)methyl)-3-phenylpropanamide,
[74] 2-(3-Fluoro-4-(methylsulfonamido)phenyl)-N-((2-(4-methylpiperidin-1-yl)-6-(trifluoromethyl)pyridin-3-yl)methyl)-3-phenylbutanamide,
[75] 2-(3-Fluoro-4-(methylsulfonamido)phenyl)-N-((2-(4-methylpiperidin-1-yl)-6-(trifluoromethyl)pyridin-3-yl)methyl)-3-o-tolylpropanamide,
[76] 2-(3-Fluoro-4-(methylsulfonamido)phenyl)-N-((2-(4-methylpiperidin-1-yl)-6-(trifluoromethyl)pyridin-3-yl)methyl)-3-m-tolylpropanamide,
[77] 2-(3-Fluoro-4-(methylsulfonamido)phenyl)-N-((2-(4-methylpiperidin-1-yl)-6-(trifluoromethyl)pyridin-3-yl)methyl)-3-p-tolylpropanamide, [M + H] 608
[78] 2-(3-Fluoro-4-(methylsulfonamido)phenyl)-3-(2-fluorophenyl)-N-((2-(4-methylpiperidin-1-yl)-6-(trifluoromethyl)pyridin-3-yl)methyl)propanamide,
[79] 2-(3-Fluoro-4-(methylsulfonamido)phenyl)-3-(3-fluorophenyl)-N-((2-(4-methylpiperidin-1-yl)-6-(trifluoromethyl)pyridin-3-yl)methyl)propanamide,
[80] 2-(3-Fluoro-4-(methylsulfonamido)phenyl)-3-(4-fluorophenyl)-N-((2-(4-methylpiperidin-1-yl)-6-(trifluoromethyl)pyridin-3-yl)methyl)propanamide, -continued

[81] 2-(3-Fluoro-4-(methylsulfonamido)phenyl)-N-((2-(4-methylpiperidin-1-yl)-6-(trifluoromethyl)pyridin-3-yl)methyl)-3-(3-(trifluoromethyl)phenyl)propanamide,
[82] 2-(3-Fluoro-4-(methylsulfonamido)phenyl)-N-((2-(4-methylpiperidin-1-yl)-6-(trifluoromethyl)pyridin-3-yl)methyl)-3-(4-(trifluoromethyl)phenyl)propanamide,
[83] 2-(3-Fluoro-4-(methylsulfonamido)phenyl)-3-(4-hydroxy-3-methoxyphenyl)-N-((2-(4-methylpiperidin-1-yl)-6-(trifluoromethyl)pyridin-3-yl)methyl)propanamide,
[84] N-((2-(Cyclohexylthio)-6-(trifluoromethyl)pyridin-3-yl)methyl)-2-(3-fluoro-4-(methylsulfonamido)phenyl)-3-(2-fluorophenyl)propanamide,
[85] N-((2-(Cyclohexylthio)-6-(trifluoromethyl)pyridin-3-yl)methyl)-2-(3-fluoro-4-(methylsulfonamido)phenyl)-3-(3-fluorophenyl)propanamide,
[86] N-((2-(Cyclohexylthio)-6-(trifluoromethyl)pyridin-3-yl)methyl)-2-(3-fluoro-4-(methylsulfonamido)phenyl)-3-(4-fluorophenyl)propanamide, [M + H] 629
[87] N-((2-(Cyclohexylthio)-6-(trifluoromethyl)pyridin-3-yl)methyl)-2-(3-fluoro-4-(methylsulfonamido)phenyl)-3-(3-(trifluoromethyl)phenyl)propanamide,
[88] N-((2-(Cyclohexylthio)-6-(trifluoromethyl)pyridin-3-yl)methyl)-2-(3-fluoro-4-(methylsulfonamido)phenyl)-3-(4-(trifluoromethyl)phenyl)propanamide und
[89] N-((2-(Cyclohexylthio)-6-(trifluoromethyl)pyridin-3-yl)methyl)-2-(3-fluoro-4-(methylsulfonamido)phenyl)-3-(4-hydroxy-3-methoxyphenyl)propanamide;

Pharmacological Data

The affinity of the compounds of the invention for the vanilloid receptor 1 (VR1/TRPV1-Receptor) was determined as described above (Pharmacological Methods I and II). The compounds of the invention corresponding to formula I were found to exhibit excellent affinity to the VR1/TRPV1 receptor (Table 2).

TABLE 2

| Compound of Example | $K_i$ (Rat) Capsaicin [nM] | $K_i$ (Human) Capsaicin [nM] | $IC_{50}$ (Human)[nM] following pH-stimulus |
|---|---|---|---|
| 1 |  | 31.1 | 118 |
| 2 | 98.7 | 31% @ 5 μM; 2% @ 1 μM | 1392 |
| 3 |  | 1.3 | 79 |
| 4 | 265 | 62.5 | 1586 |
| 5 | 45.5 | 49 | 886 |
| 6 | 34.9 | 65.7 | 54% @ 10 μM; 42% @ 5 μM; 20% @ 1 μM; 4% @ 0.1 μM |
| 7 | 37.8 | 124 | 18% @ 10 μM; 15% @ 5 μM; 0% @ 1 μM; |
| 8 | 99% @ 5 μM; 26% @ 1 μM; | 80% @ 5 μM 0% @ 1 μM; | 20% @ 10 μM; 0% @ 5 μM |
| 13 | 43% @ 5 μM 27% @ 1 μM; 0% @ 0.1 μM | 25% @ 5 μM 0% @ 1 μM; |  |
| 14 | 117 | 77% @ 5 μM 20% @ 1 μM; 0% @ 0.1 μM | 33% @ 10 μM; 4% @ 5 μM |
| 15 | 69% @ 5 μM 7% @ 1 μM; | 33% @ 5 μM 0% @ 1 μM; | 32% @ 10 μM 7% @ 5 μM; |
| 16 | 69% @ 5 μM 15% @ 1 μM; |  |  |
| 21 | 20.6 | 88.7 | 949 |
| 22 | 31.3 | 103 | 46% @ 10 μM 27% @ 5 μM; 0% @ 1 μM |
| 34 | 6.4 | 2.4 | 21.6 |
| 35 | 13.6 | 3.4 | 246 |
| 40 | 109 | 42.9 | 3138 |
| 41 | 1.8 | 0.1 | 86.7 |
| 42 | 6.3 | 1.1 | 31.6 |
| 77 | 158 | 17% @ 5 μM 0% @ 1 μM |  |

The value following the symbol "@" indicates the concentration at which the inhibition (in percent) was determined.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A compound corresponding to formula I:

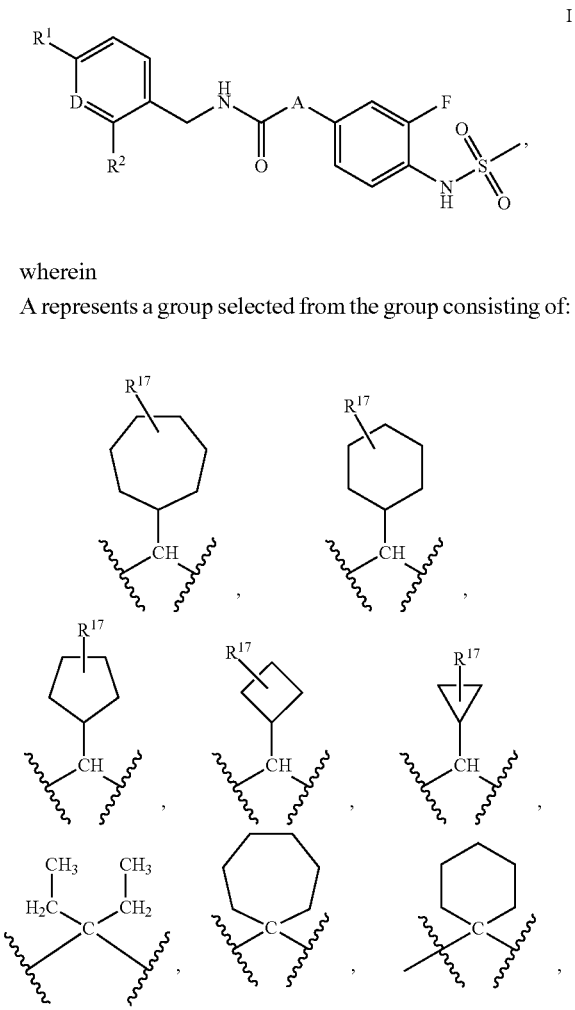

wherein

A represents a group selected from the group consisting of:

-continued

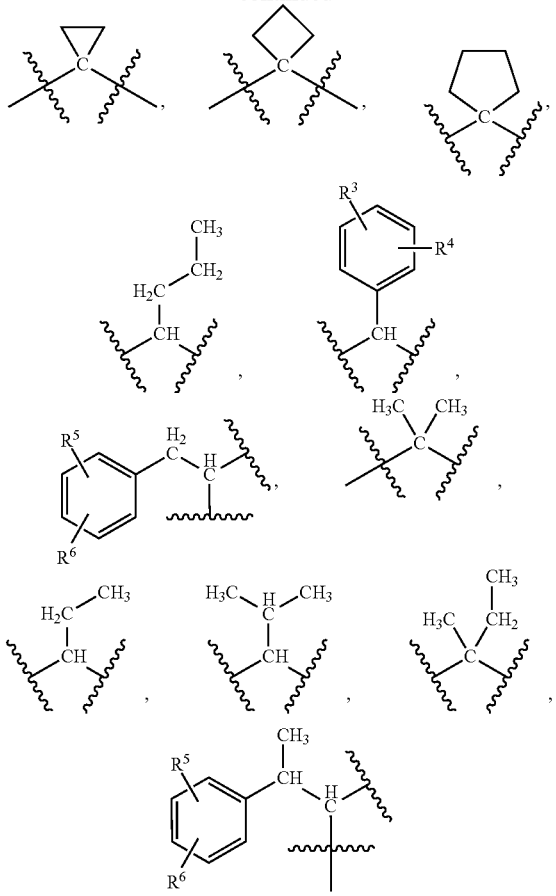

D represents N;
R[1] represents —SF$_5$, —OCF$_3$, —OCF$_2$H, —OCFH$_2$, —CFH$_2$, —CF$_2$H, —CF$_3$ or an unsubstituted, monosubstituted or polysubstituted tert-butyl group;
R[2] represents —NR[8]R[9] or —SR[11];
R[3] represents H; F; Cl; Br; I; —SF$_5$; —NO$_2$; —CF$_3$; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NH$_2$; —NH—CH$_3$; —NH—C$_2$H$_5$; —N(CH$_3$)$_2$; —N(C$_2$H$_5$)$_2$; methyl; ethyl; isopropyl; n-propyl; n-butyl; tert-butyl; sec-butyl; isobutyl; —O-phenyl; —O—CH$_3$; —O—C$_2$H$_5$; —O—C(CH$_3$)$_3$; —O—CH(CH$_3$)$_2$, or —O—CH$_2$—CH$_2$—CH$_2$—CH$_3$;
R[4] represents H, F or methyl;
R[5] and R[6] each independently represent H, F or methyl;
R[8] and R[9] together with the interconnecting nitrogen atom as ring member form an unsubstituted piperidinyl radical or form a piperidinyl radical which is substituted by one methyl substituent in the 4-position of the piperidinyl ring;
R[11] represents unsubstituted cyclohexyl; and
R[17] represents a linear or branched, saturated or unsaturated, unsubstituted, monosubstituted or polysubstituted aliphatic C$_{1-10}$ radical;
or a salt thereof.

2. A compound according to claim 1, wherein said compound is in the form of an isolated stereoisomer.

3. A compound according to claim 1, wherein said compound is in the form of a mixture of stereoismers in any mixing ratio.

4. A compound according to claim 1, wherein said compound is in the form of a racemic mixture.

5. A compound according to claim 1, wherein said compound corresponds to one of the formulas Ic and Ie:

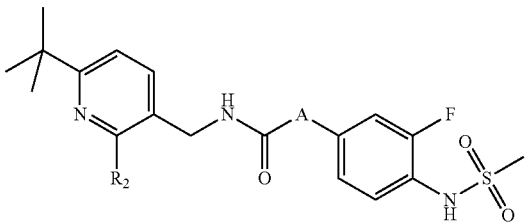

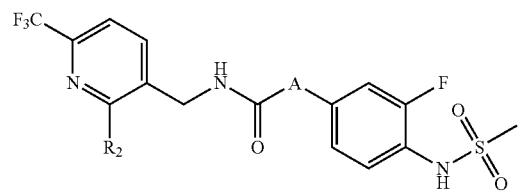

wherein R[2] and A each have the respective meanings given in claim 1;
or a salt thereof.

6. A compound according to claim 1, wherein said compound corresponds to formula Ia:

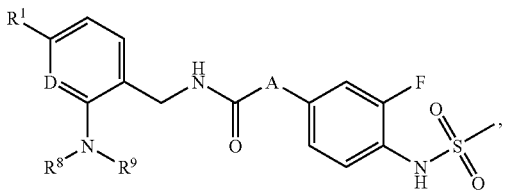

wherein D, R[1], R[8], R[9] and A each have the respective meanings given in claim 1;
or a salt thereof.

7. A compound according to claim 1, wherein said compound corresponds to formula Ib:

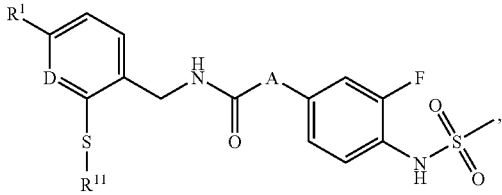

wherein D, R[1], R[11] and A each have the respective meanings given in claim 1;
or a salt thereof.

8. A compound according to claim 1, wherein said compound is selected from the group consisting of:

[1] 2-Cyclohexyl-2-(3-flouro-4-(methylsulfonamido)phenyl)-N-((2-(4-methylpiperidin-1-yl)-6-(triflouromethyl)pyridin-3-yl)methyl)-acetamide,
[2] 2-Cyclohexyl-N-((2-(cyclohexylthio)-6-(triflouromethyl)pyridin-3-yl)-methyl)-2-(3-flouro-4-(methylsulfonamido)phenyl)acetamide,
[3] 2-(3-Flouro-4-(methylsulfonamido)phenyl)-N-((2-(4-methylpiperidin-1-yl)-6-(triflouromethyl)pyridin-3-yl)methyl)-2-phenylacetamide,
[4] N-((2-(Cyclohexylthio)-6-(triflouromethyl)pyridin-3-yl)methyl)-2-(3-flouro-4-(methylsulfonamido)phenyl)-2-phenylacetamide,
[5] 2-(3-Flouro-4-(methylsulfonamido)phenyl)-2-methyl-N-((2-(4-methylpiperidin-1-yl)-6-(triflouromethyl)pyridin-3-yl)methyl)-propanamide,
[6] N-((2-(Cyclohexylthio)-6-(triflouromethyl)pyridin-3-yl)methyl)-2-(3-flouro-4-(methylsulfonamido)phenyl)-2-methylpropanamide,
[7] 2-(3-Flouro-4-(methylsulfonamido)phenyl)-2-methyl-N-((2-(4-methylpiperidin-1-yl)-6-(triflouromethyl)pyridin-3-yl)methyl)-butanamide,
[8] N-((2-(Cyclohexylthio)-6-(triflouromethyl)pyridin-3-yl)methyl)-2-(3-flouro-4-(methylsulfonamido)phenyl)-2-methylbutanamide,
[9] 1-(3-Flouro-4-(methylsulfonamido)phenyl)-N-((2-(4-methylpiperidin-1-yl)-6-(triflouromethyl)pyridin-3-yl)-methyl)cyclopropanecarboxamide,
[10] N-((2-(Cyclohexylthio)-6-(triflouromethyl)pyridin-3-yl)methyl)-1-(3-flouro-4-(methylsulfonamido)phenyl)-cyclopropanecarboxamide,
[11] 1-(3-Flouro-4-(methylsulfonamido)phenyl)-N-((2-(4-methylpiperidin-1-yl)-6-(triflouromethyl)pyridin-3-yl)-methyl)cyclobutanecarboxamide,
[12] N-((2-(Cyclohexylthio)-6-(triflouromethyl)pyridin-3-yl)methyl)-1-(3-flouro-4-(methylsulfonamido)phenyl)cyclobutanecarboxamide,
[13] 1-(3-Flouro-4-(methylsulfonamido)phenyl)-N-((2-(4-methylpiperidin-1-yl)-6-(triflouromethyl)(pyridin-3-yl)methyl)-cyclopentanecarboxamide,
[14] N-((2-(Cyclohexylthio)-6-(triflouromethyl)pyridin-3-yl)methyl)-1-(3-flouro-4-(methylsulfonamido)phenyl)cyclopentanecarboxamide,
[15] 1-(3-Flouro-4-(methylsulfonamido)phenyl)-N-((2-(4-methylpiperidin-1-yl)-6-(triflouromethyl)pyridin-3-yl)methyl)-cyclohexanecarboxamide,
[16] N-((2-(Cyclohexylthio)-6-(triflouromethyl)pyridin-3-yl)methyl)-1-(3-flouro-4-(methylsulfonamido)phenyl)cyclohexanecarboxamide,
[17] 2-Cyclopropyl-2-(3-flouro-4-(methylsulfonamido)phenyl)-N-((2-(4-methylpiperidin-1-yl)-6-(triflouromethyl)pyridin-3-yl)-methyl)acetamide,
[18] N-((2-(Cyclohexylthio)-6-(triflouromethyl)pyridin-3-yl)methyl)-2-cyclopropyl-2-(3-flouro-4-(methylsulfonamido)phenyl)acetamide,
[19] 2-Cyclobutyl-2-(3-flouro-4-(methylsulfonamido)phenyl)-N-((2-(4-methylpiperidin-1-yl)-6-(triflouromethyl)pyridin-3-yl)methyl)-acetamide,
[20] 2-Cyclobutyl-N-((2-(cyclohexylthio)-6-(triflouromethyl)pyridin-3-yl)methyl)-2-(3-flouro-4-(methylsulfonamido)phenyl)acetamide,
[21] 2-Cyclopentyl-2-(3-flouro-4-(methylsulfonamido)phenyl)-N-((2-(4-methylpiperidin-1-yl)-6-(triflouromethyl)pyridin-3-yl)methyl)-acetamide,
[22] N-((2-(Cyclohexylthio)-6-(triflouromethyl)pyridin-3-yl)methyl)-2-cyclopentyl-2-(3-flouro-4-(methylsulfonamido)phenyl)acetamide,
[24] N-((6-tert-Butyl-2-(4-methylpiperidin-1-yl)pyridin-3-yl)methyl)-2-(3-flouro-4-(methylsulfonamido)phenyl)-2-phenylacetamide,
[33] 2-(3-Flouro-4-(methylsulfonamido)phenyl)-2-(2-flourophenyl)-N-((2-(4-methylpiperidin-1-yl)-6-(triflouromethyl)pyridin-3-yl)methyl)acetamide,
[34] 2-(3-Flouro-4-(methylsulfonamido)phenyl)-2-(3-flourophenyl)-N-((2-(4-methylpiperidin-1-yl)-6-(triflouromethyl)pyridin-3-yl)methyl)acetamide,
[35] 2-(3-Flouro-4-(methylsulfonamido)phenyl)-2-(4-flourophenyl)-N-((2-(4-methylpiperidin-1-yl)-6-(triflouromethyl)pyridin-3-yl)methyl)acetamide,
[36] 2-(3-Chlorphenyl)-2-(3-flouro-4-(methylsulfonamido)phenyl)-N-((2-(4-methylpiperidin-1-yl)-6-(triflouromethyl)pyridin-3-yl)methyl)acetamide,
[37] 2-(4-Chlorphenyl)-2-(3-flouro-4-(methylsulfonamido)phenyl)-N-((2-(4-methylpiperidin-1-yl)-6-(triflouromethyl)pyridin-3-yl)methyl)acetamide,
[38] 2-(3-Bromophenyl)-2-(3-flouro-4-(methylsulfonamido)phenyl)-N-((2-(4-methylpiperidin-1-yl)-6-(triflouromethyl)pyridin-3-yl)methyl)acetamide,
[39] 2-(4-Bromophenyl)-2-(3-flouro-4-(methylsulfonamido)phenyl)-N-((2-(4-methylpiperidin-1-yl)-6-(triflouromethyl)pyridin-3-yl)methyl)acetamide,
[40] 2-(3-Flouro-4-(methylsulfonamido)phenyl)-N-((2-(4-methylpiperidin-1-yl)-6-(triflouromethyl)pyridin-3-yl)methyl)-2-o-tolylacetamide,
[41] 2-(3-Flouro-4-(methylsulfonamido)phenyl)-N-((2-(4-methylpiperidin-1-yl)-6-(triflouromethyl)pyridin-3-yl)methyl)-2-m-tolylacetamide,
[42] 2-(3-Flouro-4-(methylsulfonamido)phenyl)-N-((2-(4-methylpiperidin-1-yl)-6-(triflouromethyl)pyridin-3-yl)methyl)-2-p-tolylacetamide,
[43] 2-(3-Flouro-4-(methylsulfonamido)phenyl)-N-((2-(4-methylpiperidin-1-yl)-6-(triflouromethyl)pyridin-3-yl)methyl)-2-(3-(triflouromethyl)-phenyl)acetamide,
[44] 2-(3-Flouro-4-(methylsulfonamido)phenyl)-N-((2-(4-methylpiperidin-1-yl)-6-(triflouromethyl)pyridin-3-yl)methyl)-2-(4-(triflouromethyl)-phenyl)acetamide,
[45] 2-(3-Flouro-4-(methylsulfonamido)phenyl)-2-(4-hydroxyphenyl)-N-((2-(4-methylpiperidin-1-yl)-6-(triflouromethyl)pyridin-3-yl)methyl)acetamide,
[46] 2-(3-Flouro-4-(methylsulfonamido)phenyl)-2-(4-methoxyphenyl)-N-((2-(4-methylpiperidin-1-yl)-6-(triflouromethyl)pyridin-3-yl)methyl)acetamide,
[49] 2-(3-Flouro-4-(methylsulfonamido)phenyl)-N-((2-(4-methylpiperidin-1-yl)-6-(triflouromethyl)pyridin-3-yl)methyl)-2-(4-phenoxyphenyl)acetamide,
[52] N-((2-(Cyclohexylthio)-6-(triflouromethyl)pyridin-3-yl)methyl)-2-(3-flouro-4-(methylsulfonamido)phenyl)-2-(2-flourophenyl)-acetamide,
[53] N-((2-(Cyclohexylthio)-6-(triflouromethyl)pyridin-3-yl)methyl)-2-(3-flouro-4-(methylsulfonamido)phenyl)-2-(3-flourophenyl)-acetamide,
[54] N-((2-(Cyclohexylthio)-6-(triflouromethyl)pyridin-3-yl)methyl)-2-(3-flouro-4-(methylsulfonamido)phenyl)-2-(4-flourophenyl)-acetamide,
[55] 2-(3-Chlorphenyl)-N-((2-(cyclohexylthio)-6-(triflouromethyl)-pyridin-3-yl)methyl)-2-(3-flouro-4-(methylsulfonamido)phenyl)-acetamide,
[56] 2-(4-Chlorphenyl)-N-((2-(cyclohexylthio)-6-(triflouromethyl)-pyridin-3-yl)methyl)-2-(3-flouro-4-(methylsulfonamido)phenyl)-acetamide,
[57] 2-(3-Bromophenyl)-N-((2-(cyclohexylthio)-6-(triflouromethyl)-pyridin-3-yl)methyl)-2-(3-flouro-4-(methylsulfonamido)phenyl)-acetamide,
[58] 2-(4-Bromophenyl)-N-((2-(cyclohexylthio)-6-(triflouromethyl)-pyridin-3-yl)methyl)-2-(3-flouro-4-(methylsulfonamido)-phenyl)acetamide,
[59] N-((2-(Cyclohexylthio)-6-(triflouromethyl)pyridin-3-yl)methyl)-2-(3-flouro-4-(methylsulfonamido)phenyl)-2-o-tolylacetamide,
[60] N-((2-(Cyclohexylthio)-6-(triflouromethyl)pyridin-3-yl)methyl)-2-(3-flouro-4-(methylsulfonamido)phenyl)-2-m-tolylacetamide,
[61] N-((2-(Cyclohexylthio)-6-(triflouromethyl)pyridin-3-yl)methyl)-2-(3-flouro-4-(methylsulfonamido)phenyl)-2-p-tolylacetamide,
[62] N-((2-(Cyclohexylthio)-6-(triflouromethyl)pyridin-3-yl)methyl)-2-(3-flouro-4-(methylsulfonamido)phenyl)-2-(3-(triflouromethyl)-phenyl)acetamide,
[63] N-((2-(Cyclohexylthio)-6-(triflouromethyl)pyridin-3-yl)methyl)-2-(3-flouro-4-(methylsulfonamido)phenyl)-2-(4-(triflouromethyl)-phenyl)acetamide,
[64] N-((2-(Cyclohexylthio)-6-(triflouromethyl)pyridin-3-yl)methyl)-2-(3-flouro-4-(methylsulfonamido)phenyl)-2-(4-hydroxyphenyl)-acetamide,
[65] N-((2-(Cyclohexylthio)-6-(triflouromethyl)pyridin-3-yl)methyl)-2-(3-flouro-4-(methylsulfonamido)phenyl)-2-(4-methoxyphenyl)-acetamide,
[68] N-((2-(Cyclohexylthio)-6-(triflouromethyl)pyridin-3-yl)methyl)-2-(3-flouro-4-(methylsulfonamido)phenyl)-2-(4-phenoxyphenyl)-acetamide,
[73] 2-(3-Flouro-4-(methylsulfonamido)phenyl)-N-((2-(4-methylpiperidin-1-yl)-6-(triflouromethyl)pyridin-3-yl)methyl)-3-phenylpropanamide,
[74] 2-(3-Flouro-4-(methylsulfonamido)phenyl)-N-((2-(4-methylpiperidin-1-yl)-6-(triflouromethyl)pyridin-3-yl)methyl)-3-phenylbutanamide,
[75] 2-(3-Flouro-4-(methylsulfonamido)phenyl)-N-((2-(4-methylpiperidin-1-yl)-6-(triflouromethyl)pyridin-3-yl)methyl-3-o-tolylpropanamide,
[76] 2-(3-Flouro-4-(methylsulfonamido)phenyl)-N-((2-(4-methylpiperidin-1-yl)-6-(triflouromethyl)pyridin-3-yl)methyl)-3-m-tolylpropanamide,

[77] 2-(3-Flouro-4-(methylsulfonamido)phenyl)-N-((2-(4-methylpiperidin-1-yl)-6-(triflouromethyl)pyridin-3-yl)methyl)-3-p-tolylpropanamide,
[78] 2-(3-Flouro-4-(methylsulfonamido)phenyl)-3-(2-flourophenyl)-N-((2-(4-methylpiperidin-1-yl)-6-(triflouromethyl)pyridin-3-yl)methyl)propanamide,
[79] 2-(3-Flouro-4-(methylsulfonamido)phenyl)-3-(3-flourophenyl)-N-((2-(4-methylpiperidin-1-yl)-6-(triflouromethyl)pyridin-3-yl)methyl)propanamide,
[80] 2-(3-Flouro-4-(methylsulfonamido)phenyl)-3-(4-flourophenyl)-N-((2-(4-methylpiperidin-1-yl)-6-(triflouromethyl)pyridin-3-yl)methyl)propanamide,
[84] N-((2-(Cyclohexylthio)-6-(triflouromethyl)pyridin-3-yl)methyl)-2-(3-flouro-4-(methylsulfonamido)phenyl)-3-(2-flourophenyl)propanamide,
[85] N-((2-(Cyclohexylthio)-6-(triflouromethyl)pyridin-3-yl)methyl)-2-(3-flouro-4-(methylsulfonamido)phenyl)-3-(3-flourophenyl)propanamide, and
[86] N-((2-(Cyclohexylthio)-6-(triflouromethyl)pyridin-3-yl)methyl)-2-(3-flouro-4-(methylsulfonamido)phenyl)-3-(4-flourophenyl)propanamide.

9. A compound according to claim 1, wherein said compound present in a concentration below 2000 nM causes a 50% displacement of capsaicin present in a concentration of 100 nM, in the FLIPR assay using CHO-K1 cells transfected with the human VR1 gene.

10. A compound according to claim 1, wherein said compound present in a concentration below 300 nM causes a 50% displacement of capsaicin present in a concentration of 100 nM, in the FLIPR assay using CHO-K1 cells transfected with the human VR1 gene.

11. A compound according to claim 1, wherein said compound present in a concentration below 75 nM causes a 50% displacement of capsaicin present in a concentration of 100 nM, in the FLIPR assay using CHO-K1 cells transfected with the human VR1 gene.

12. A compound according to claim 1, wherein said compound present in a concentration below 10 nM causes a 50% displacement of capsaicin present in a concentration of 100 nM, in the FLIPR assay using CHO-K1 cells transfected with the human VR1 gene.

13. A pharmaceutical composition comprising a compound according to claim 1, and at least one physiologically acceptable carrier or adjuvant.

14. A method of treating or inhibiting pain in a subject, said method comprising administering to said subject a pharmacologically effective amount of a compound according to claim 1.

15. A method according to claim 14, wherein said pain is selected from the group consisting of acute pain, chronic pain, neuropathic pain, visceral pain; arthralgia; hyperalgesia; allodynia; causalgia and migraine.

16. A process for preparing a compound according to claim 1, said process comprising:
converting a compound corresponding to formula II:

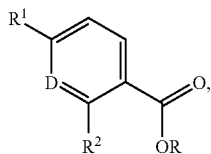

wherein
$R^1$, $R^2$ and D each have the respective meanings given in claim 1, and
R represents hydrogen or a linear or branched $C_{1-6}$-alkyl group,
in a reaction medium, in the presence of at least one reducing agent, into a compound corresponding to formula III:

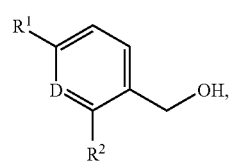

wherein $R^1$, $R^2$ and D each have the meanings given above, and optionally isolating or purifying the compound of formula III, and converting the compound of formula III in a reaction medium in the presence of diphenylphosphorylazide or of $HN_3$, to a compound corresponding to formula IV:

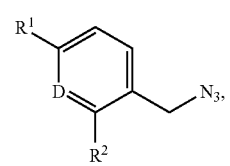

wherein $R^1$, $R^2$ and D have the meanings given above, and optionally isolating or purifying the compound of formula IV, and converting the compound corresponding to formula IV:

in a reaction medium in the presence of a reducing agent, or in a reaction medium in the presence of a catalyst and of hydrogen or hydrazine, or in a reaction medium in the presence of triphenylphosphine to a compound corresponding to formula V:

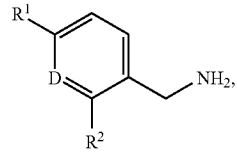

wherein $R^1$, $R^2$ and D each have the meanings given above, and optionally isolating or purifying the compound of formula V;

or to a compound corresponding to formula VI:

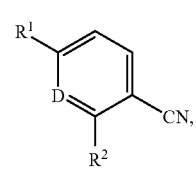

wherein $R^1$, $R^2$ and D each have the meanings given above, in a reaction medium and in the presence of a catalyst, under a blanket of hydrogen, optionally in the presence of at least one acid, or to a compound corresponding to formula V; and optionally isolating or purifying the compound of formula V; and reacting the compound of formula V with a compound of formula VII:

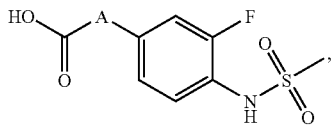

VII wherein A has the meaning given in claim 1,
in a reaction medium, optionally in the presence of at least one base,
or with a compound corresponding to formula VIII:

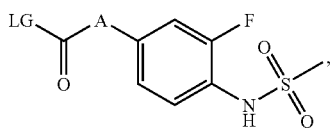

VIII wherein A has the meaning given above, and LG represents a leaving group,
in a reaction medium, optionally in the presence of at least one base,
to form a compound corresponding to formula I:

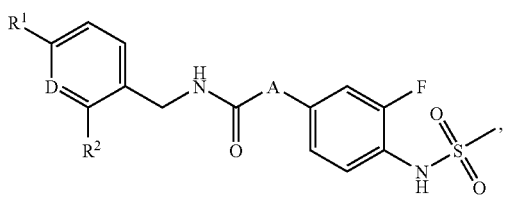

I wherein $R^1$, $R^2$, D and A each have the meanings stated above, and
optionally purifying or isolating the resulting compound.

17. A process according to claim 16, wherein the conversion of the compound of formula II to a compound of formula III is effected in the presence of a reducing agent selected from the group consisting of sodium hydride, sodium, potassium hydride, lithium aluminum hydride, sodium tetrahydridoborate, and di(isobutyl)aluminum hydride; or wherein the compound corresponding to formula IV is converted to a compound of formula V in the presence of a reducing agent selected from the group consisting of sodium hydride, potassium hydride, lithium aluminum hydride, sodium tetrahydridoborate, and di(isobutyl)aluminum hydride; or wherein the compound of formula IV is converted to a compound of formula V in the presence of a platinum- or palladium-based catalyst; or wherein the compound of formula V is obtained in the form of a hydrochloride salt; or wherein the compound of formula V is converted to a compound of formula VI in the presence of at least one reducing agent selected from the group consisting of $BH_3 \cdot S(C_{1-13})_2$, lithium aluminum hydride, and sodium tetrahydridoborate, optionally in the presence of $NiCl_2$, wherein a compound of formula V is converted to a compound of formula VI in the presence of a catalyst palladium- or platinum-based catalyst and in the presence of hydrochloric acid; or wherein the reaction of the compound of formula V with the compound of formula VII is carried out in the presence of a coupling agent; or wherein LG represents a chlorine atom or bromine atom.

* * * * *